(12) United States Patent
Keasling et al.

(10) Patent No.: US 8,178,338 B2
(45) Date of Patent: May 15, 2012

(54) INDUCIBLE EXPRESSION VECTORS AND METHODS OF USE THEREOF

(75) Inventors: Jay D. Keasling, Berkeley, CA (US); Sung Kuk Lee, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 833 days.

(21) Appl. No.: 11/993,419

(22) PCT Filed: Jun. 29, 2006

(86) PCT No.: PCT/US2006/025995
§ 371 (c)(1),
(2), (4) Date: Nov. 25, 2008

(87) PCT Pub. No.: WO2007/005837
PCT Pub. Date: Jan. 11, 2007

(65) Prior Publication Data
US 2009/0203081 A1    Aug. 13, 2009

Related U.S. Application Data

(60) Provisional application No. 60/695,940, filed on Jul. 1, 2005.

(51) Int. Cl.
*C12N 15/00* (2006.01)
(52) U.S. Cl. ............... 435/252.33; 435/320.1; 536/24.1
(58) Field of Classification Search .................. None
See application file for complete search history.

(56) References Cited

OTHER PUBLICATIONS

Horswill et al., Journal of Bacteriology, vol. 179 (1997) pp. 928-940.*
Bartolome et al. (Abstract), Gene, vol. 102 (1991) pp. 75-78.*
Srinivasan, et al. AppaDB: an AcedB database for the nematode satellite organism *Pristionchus pacificus*. Nucleic Acids Res. Jan. 1, 2004;32(Database issue):D421-2.
Amann, E., J. Brosius, and M. Ptashne. Vectors bearing a hybrid trp-lac promoter useful for regulated expression of cloned genes in *Escherichia coli*. Gene, 1983, 25:167-178.
Baneyx, F. Recombinant protein expression in *Escherichia coli*. Curr. Opin. Biotechnol., 1999, 10:411-421.
Figge, J., et al. Stringent regulation of stably integrated chloramphenicol acetyl transferase genes by *E. coli* lac repressor in monkey cells. Cell, 1988, 52:713-722.
Guzman, L. M., et al. Tight regulation, modulation, and high-level expression by vectors containing the arabinose PBAD promoter. J. Bacteriol., 1995, 177: 4121-4130.
Haller, T., et al. Discovering new enzymes and metabolic pathways: conversion of succinate to propionate by *Escherichia coli*. Biochemistry, 2000, 39:4622-4629.
Jensen, P. R., et al. The use of lac-type promoters in control analysis. Eur. J. Biochem., 1993, 211:181-191.
Khlebnikov, A., and J. D. Keasling. Effect of lacY expression on homogeneity of induction from the Ptac and Ptrc promoters by natural and synthetic inducers. Biotechnol. Prog., 2002, 18:672-674.
Khlebnikov, A., et al. Regulatable arabinose-inducible gene expression system with consistent control in all cells of a culture. J. Bacteriol., 2000, 182:7029-7034.
Lee, S. K., J. D. Newman, and J. D. Keasling. Catabolite repression of the propionate catabolic genes in *Escherichia coli* and *Salmonella enterica*: evidence for involvement of the cyclic AMP receptor protein. J. Bacteriol., 2005, 187:2973-2800.
Novick, A., and M. Weiner. Enzyme induction as an all-or-none phenomenon. Proc. Natl. Acad. Sci. USA, 1957, 43:553-566.
Palacios, S., and J. C. Escalante-Semerena. prpR, ntrA, and ihf functions are required for expression of the prpBCDE operon, encoding enzymes that catabolize propionate in *Samonella enterica* serovar typhimurium LT2. J. Bacteriol., 2000, 182:905-910.
Palacios, S., and J. C. Escalante-Semerena. 2-Methylcitrate-dependent activation of the propionate catabolic operon (prpBCDE) of *Salmonella enterica* by the PrpR protein. Microbiology, 2004, 150:3877-3887.
Siegele, D. A., and J. C. Hu. Gene expression from plasmids containing the araBAD promoter at subsaturating inducer concentrations represents mixed populations. Proc. Natl. Acad. Sci. USA, 1997, 94:8168-8172.
Su, T. Z., H. Schweizer, and D. L. Oxender. A novel phosphate-regulated expression vector in *Escherichia coli*. Gene, 1990, 90:129-133.
Sung Kuk Lee, and Jay D. Keasling. Heterologous protein production in *Escherichia coli* using the propionate-inducible pPro system. Protein Expression & Purification., 2008, 61:197-203.
Sung Kuk Lee, and Jay D. Keasling. Effect of glucose or glycerol as the sole carbon on gene expression from the Salmonella prpBCDE promoter in *Escherichia coli*. Biotechnology Progress, 2006, 22 (6): 1547-1551.
Sung Kuk Lee, and Jay D. Keasling. A *Salmonella*-based, propionate-inducible, expression system for *Salmonella enterica*. Gene, 2006, 377: 6-11.
Sung Kuk Lee, and Jay D. Keasling. Propionate-regulated high-yield protein production in *Escherichia coli*. Biotechnology and Bioengineering, 2006, 93 (5):912-918.
Sung Kuk Lee, and Jay D. Keasling. A propionate-inducible expression system for enteric bacteria. Applied and Environmental Microbiology, 2005, 71:6856-6862.
Corcoran, Colin P., "H-NS. Silences *gfp*, the Green Fluorescent Protein Gene: *gfp*$^{TCD}$ Is a Genetically Remastered *gfp* with Reduced Susceptibility to H-NS-Mediated Transcription Silencing and with Enhanced Translation", Journal of Bacteriology, 2010, vol. 192, No. 18: 4790-4793.
Corcoran, Colin P., Supplemental Materials, Sep. 2010.
Lee, Sung Kuk, A Propionate-Inducible Expression System for Enteric Bacteria:, Applied and Environmental Microbiology, 2005, vol. 71, No. 11: 6856-6862.
Lee, Sung Kuk, "Heterologous Protein Production in *Escherichia coli* Using the Propionate-Inducible pPro System by Conventional and Auto-induction Methods", *Protein Expr Purif.*, 2008, vol. 61, No. 2: 197-203.

* cited by examiner

*Primary Examiner* — Jim Ketter
(74) *Attorney, Agent, or Firm* — Paula A. Borden; Bozicevic, Field & Francis LLP.

(57) ABSTRACT

The present invention provides nucleic acids that include a promoter that is inducible by a transcriptional activator protein; and a nucleotide sequence that encodes the transcriptional activator protein. The present invention provides expression vectors that provide for inducible production of gene products in a host cell. The present invention further provides host cells genetically modified with a subject expression vector. The present invention further provides methods for producing a gene product in a host cell.

6 Claims, 23 Drawing Sheets

FIG. 1A

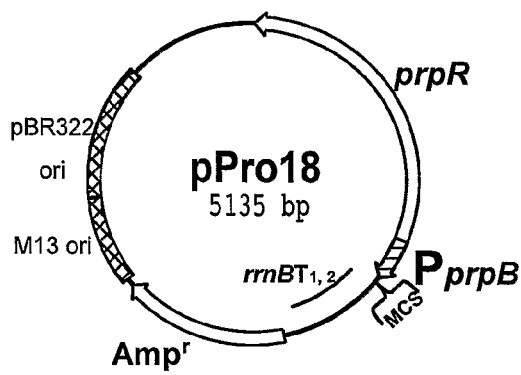

FIG. 1B

```
        Nhel         EcoRI   Sacl    Kpnl        BamHI           Sall            Sphl
MCS1    GCTAGC-----GAATTCGAGCTCGGTACCCGGGGATCCTCTAGAGTCGACCTGCAGGCATGC
MCS2    GCTAGCAGGAGGAATTCACCAT-GGTACCCGGGGATCCTCTAGAGTCGACCTGCAGGCATGC
        S.D.                Ncol    Smal        Xbal            Pstl
                                    Xmal
```

FIG. 1C

```
prp operon  TGGCACACCCCTTGCTTTGTCTTTATCAACGCAAATAACAAGTTGATAACAAAGGATGGGCTATG
pPro24      TGGCACACCCCTTGCTTTGTCTTTATCAACGCAAATAACAAGTTGATAACAAGCTAGCAGGAGGAATTCACCATG
            -24         -12                                         Nhel
```

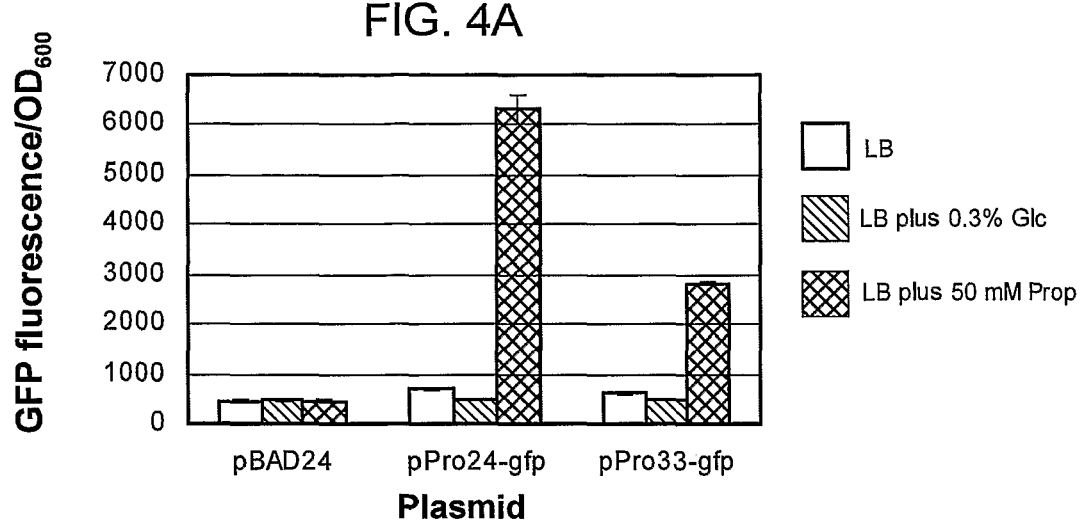
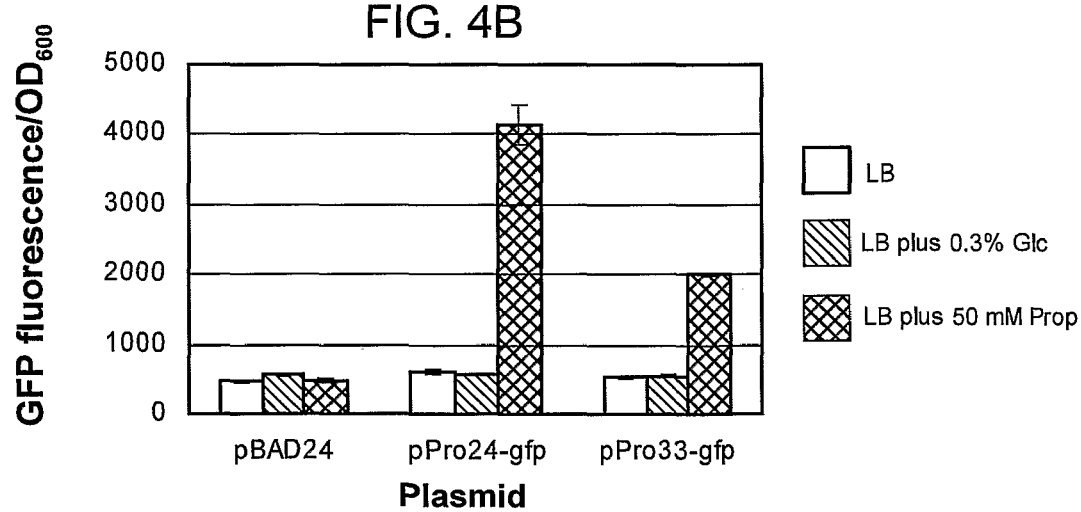

E. coli prp operon [Escherichia coli K-12 MG1655 complete genome (U00096)]

prp operon
7980 bp

FIG. 10B ccaggaaggcacgcagaaaagcgtcatcgacaccatgcagaeccgcaacgagctgtacgaaagcatcaactactaccagtac
gaagagaagctcgacaacctgtttgcccgtagccaggtgaaataaaaaacgcccgttgattgtattcgacagccgatgcctgatg — Stop codon for *prpB* gene
cgtcgctgacgcgacttatcaggcctacgaggtgcactgaactgtaggtcggataagacggatggcgtcgcatccgacaaccg
atgcctgatgcgccgctgacgtgacttatcaggcctacggggtgcactgaactgtaggtcggataagacgcatagcgtcgcatc
cgacaaccgatgcctgatgcgccgctgacgcgacttatcaggcctacggggtgcactgaactgtaggtcggataagacgcata
gcgtcgcatccgacaaccgatgcctgatgcgccgctgacgcgacttatcaggcctacggggtgaactgaactgtaggtcggat
aagacgcatagcgtcgcatccgacaacaatctcgaccctacaaatgataacaatgacgaggacaacatgagcgacacaacgat — Start codon for *prpC* gene
cctgcaaaacagtacccatgtcattaaaccgaaaaaatctgtggcactttctggcgttccggcgggcaatacggcgctctgcacc
gtgggtaaaagtggcaatgacctgcattaccgcggctacgatattcttgatctggcgaaacattgcgaatttgaagaagtggcgc
atctgctgatccacggcaaactgccgacccgtgacgaactcgccgcttacaaaacgaaactgaaagccctgcgcggtttaccg
gctaacgtgcgtaccgtgctggaagccttaccggcggcgtcgcaccgatggatgttatgcgcaccggtgtttccgcgctcggc
tgcacgctgccagaaaaagagggggcataccgtctctggcgcgcgggatattgccgacaaactgctggcgtcgcttagctcgatt
ctcctttattggtatcactacagccacaacggcgaacgcatccaaccggaaaccgatgacgactccatcggcggtcacttcctgc
atctgctgcacggcgaaaagccatcgcaaagctgggaaaaggcgatgcatatctcgctggtgctgtacgccgaacacgagttta
acgcctccacctttaccagtcgggtgattgcgggcaccggctctgatatgtattccgcgattattggcgcgattggcgcactgcgc
gggccaaaacacggcggggcgaatgaagtgtcgctggagatccagcaacgctacgaaacgccggacgaagccgaagcag
atatccgcaagcgcgtggaaaacaaagaagtggtcattggttttggtcatccggtttacaccatcgctgacccgcgccaccaggt
gattaaacgtgtggcgaagcagctctcgcaggaaggcggctcgctgaagatgtacaacatcgccgatcgcctggaaacggtg
atgtgggagagcaaaaagatgttccccaatctcgactggttctctgctgtttcctacaacatgatgggcgttcccaccgagatgttc
acaccactgtttgttatcgcccgcgtcaccggctgggcggcgcacattatcgaacaacgtcaggacaacaaaattatccgtccttc
ccgccaattatgttggaccggaagaccgcccgtttgtcgcgctggataagcgccagtaaacctctacgaataacaataaggaaa — Stop codon for *prpC* gene
cgtacccaatgtcagctcaaatcaacaacatccgcccggaatttgatcgtgaaatcgttgatatcgtcgattacgtcatgaactacg — Start codon for *prpD* gene
aaatcagctctaaagtggcctacgacaccgcacattactgcctgctcgacacgctcggctgcggtctggaagctctcgaataccc
ggcctgtaaaaaactgctggggccaattgttcccggcaccgtcgtacccaacggcgtgcgcgtccccggaactcagttccagct
cgaccccgtccaggcggcatttaacatcggcgcgatgatccgctggctcgatttcaacgatacctggctggcggcggagtggg
gccatccttccgacaacctcggcggcattctggcaacggcggactggcttcgcgcaacgcggtcgccagcggcaaagcgcc
gttgaccatgaaacaggtgctgaccgcaatgatcaaagcccatgaaattcaggctgcatcgcgctggaaaactccttaaccg
cgtcggcctcgaccacgttctgttagtgaaagtggcttccaccgccgtggtcgccgaaatgctcggcctgacccgcgaggaaat
tctcaacgccgtttcgctggcgtggtggacggtcagtcgctgcgcacctatcgccatgcgccgaacaccggcacgcgtaaat
cctgggcggcgggcgatgccacttcccgcgcggtacgtctggcactgatggcgaaaacgggcgaaatggttaccgtcagc
cctgactgcgccggtgtggggcttctacgacgtctcctttaaaggtgaatcgttccgcttccagcgcccgtacggttcctacgttat
ggaaaatgtgctgttcaaaatctccttcccggcggagttccactcccagacggcagttgaagcagcgatgacgctctatgaacag
atgcaggcagcaggcaaaacggcggcggatatcgaaaaagtgaccattcgcacccacgaagcctgtattcgcatcatcgaca
aaaaagggccgctcaataacccggcagaccgcgatcactgcattcagtacatggtggcgatcccgctgctattcgggcgcttaa
cggcggcagattacgaggacaacgttgcgcaagataaacgcattgacgccctgcgcgagaagatcaattgctttgaagatccg
gcatttaccgctgactaccacgacccggaaaaacgcgccatcgccaatgccattacccttgagttcaccgacggcacacgattt
gaagaagtggtggtggagtacccccattggtcatgctcgccgccgtcaggatggtattccgaaactggtcgataaattcaaaatca
atctcgcgcgccagttcccgactcgccaacagcagcgcattctggaggtttctctcgacagagctcgcctggaacagatgccgg — Start codon for *prpE* gene
tcaatgagtatctcgacctgtacgtcatttaagtaaacggcggtaaggcgtaagttcaacaggagagcattatgtcttttagcgaatt
ttatcagcgttcgattaacgaaccggagcagttctgggccgagcaggcccggcgtattgactggcagacgcccttacgcaaac — Stop codon for *prpD* gene
gctcgatcacagcaatccgccgtttgcccgttggttttgtgaaggccgaaccaacttgtgccacaacgccatcgaccgctggctg
gagaaacagccagaggcgctggcgctgattgccgtctcttcggaaacagaagaagagcgcacctttaccttcgtcagctgcat
gacgaagtgaacgcggtggcctcaatgttgcgttcattgggtgtgcagcgcggcgatcggtgctggtgtatatgccgatgattg

FIG. 10C ccgaagcgcatattactctgctggcctgcgcgcgcattggcgctattcactcggtggtgtttggtggatttgcctcgcacagcgtg
gcggcgcgaattgatgacgctaaaccggtgctgattgtctcggctgatgccggagcgcgcggtggcaaaatcattccctataaa
aaattgctcgacgatgcgataagtcaggcgcagcaccagccacgccatgttttgctggtggatcgcgggctggcgaaaatggc
gcgcgtcagcgggcgggatgtcgatttcgcgtcgttgcgccatcaacacatcggcgcgcgggtaccggtggcgtggctggaa
tccaacgaaacctcctgcattctctacacttccggcacgaccggcaaacctaaaggcgtgcagcgtgacgtcggcggatatgcg
gtggcgctggcgacctcgatggacaccatttttggcggcaaagcgggcagcgtgttcttttgcgcatcggatatcggctgggtg
gtggggcattcgtatatcgtttacgcgccgctgctggcggggatggcgactatcgtttacgaaggattgccgacctggccggact
gcggcgtgtggtggacaatcgtcgagaaatatcaggttagccggatgttctcagcgccgaccgccattcgcgtgctgaaaaaat
tccctaccgctgaaattcgcaaacacgatctctcgtcgctggaagtgctctatctggctggagaaccgctggacgagccgaccg
ccagttgggtgagcaatacgctggatgtgccggtcatcgacaactactggcagaccgaatccggctggccgattatggcgattg
ctcgcggtctggacgacaggccgacgcgtctgggaagccccggtgtgccgatgtatggctataacgtgcagttgcttaatgaag
tcaccggcgaaccgtgtggcgtcaacgagaaagggatgctggtggtggaagggccgctgccgccggggtgtattcagaccat
ctggggcgacgacggccgctttgtgaagacttactggtcgctgttttcccgcccggtgtacgccacctttgactggggcatccgt
gacgctgacggttatcactttattctcgggcgcactgacgatgtaattaacgttgccgggcatcggctggggacgcgcgagattg
aagagagtatctccagccatccgggcgttgccgaagtggcggtggttggggtgaaagatgcgctgaaagggcaggtggcggt
ggcgtttgtcattccgaaagagagcgacagtctggaagatcgtgatgtggcgcactcgcaagagaaggcgattatggcgctggt
ggacagccagattggcaactttggccgcccggcgcacgtctggtttgtctcgcaattgccaaaaacgcgatccggaaaaatgct
gcgccgcacgatccaggcgatttgcgaaggacgcgatcctggagatctgacgaccattgatgatcctgcgtcgttggatcagat
ccgccaggcgatggaaga<u>gtag</u>gttattgtcggatgcgtcgcgcggtgcatccggcactgtgtgccgatgcctgatgcgacgc ── Stop codon for *prpE* gene
tgacgcgttttatcatgcctacggacctgaaccgtaggtcggataaggcgctcgcgtcgcatccgacaccatgctcagatgcctg
atgcgacgctgacgcgtcttatcaggcctacccactgt

FIG. 10D

*Salmonella prp* operon [*Salmonella typhimurium* LT2, section 20 of 220 of the complete genome (AE008712)]

NONAME

7870 bp gccatcaggcattcaggacgctgtcatttgtcttaattatccgactggtctttggcaccagcttttaaacgacgccacagagtggtg — Stop codon for *prpR* gene
cggctaatcccagataacgcgccgcggcggtcttatcgcccttaaagcgcgccagtacatcctgtaacgcgttcgcatccacg
gttgaaggcgtcagttctgctgtgttcaccataagctcaggtaataactgccgcataaattgcctgtccagcgttggcgcgggatc
gacgcttaaaaaaagcgccaggcgctccatcatattacgcagttcgcgaatattaccgggccagcgccaggccagcaaaagc
ggctgacactgtgtcaatccatgacgtatcgattcggtaaacggaatttccatcgccgccagcgactgttttaaaaagctttccgcc
agcggcaaaatatcagcctgccgctcgcgcaaaggaggaagcgtcagacgcagaatactcaggcgataaaagagatcgggg
cgaaaacgtccttgcattatctcccgatccagatcgcaatgcgtagcgctgatcacccggacatccaccgggatcggctggtgtc
cgccgacgcgagtgacggcttttcctccagtacgcgcaaaagtcgggttttgtaacggcaagggcatttcgccgatttcatccag
aaacagcgtgccgccgtgtgcgatttcaaacagccccgcccggcctcctcgtcgtgaaccggtaaacgcgccctcttcataacc
aaacagttccgcttccagcaacgactcggtaatcgcgccgcaattgacggcgacaaagggaggggatggcttattctgacggt
gaggctggcggtgaaagaacgtctggtgaatcgcctgcgccgccagctcttttccggtccctgtttcccctgaatcagcactgc
cgcacgggagcgggcatagagcgtaatcgtctggcggagctgctccatttgcggcgactggccgcgtatatcgcccagttcat
accgggtttgtaatccttgccggatgggtaatccacgcgctggcgccgtgtcagacgggtcatatccagcgcatcatgaaaag
cctgacgaacgtgccgcgcgaataaataaagatggcggtcattcctgcctcttccgccagatcggtaattaatcccgcgccga
cgacggcctcaataccgttggccttaagttcgttaatttgcccgcgcgcgtcctcttcggtgacatagcttcgctgttcaagacgga
ggtgaaacgttttctgaaaggcaagtaaagccggaatggtctcctgataggtcacgataccgatagacgaggtgagctttcccgc
tttcgccagcgcctgtaatacatcgaatccgctgggcttgatgaggatcaccggtattgacaggcggcttttaaataggccccatt
cgaacccgccgcgataatcgcgtcgcagcgctcggtcgccagttttttgcgaatgtaggtcaccgccttttcaaagccgagttga
ataggcgtgatggtcgccagatgatcgaattccaggctgatatcccgaaacagttcgaacagacgcgttacggagaccgtccag — Start codon for *prpR* gene
atcaccggtttatcgctattatcgcgcggagcgctgtgggcagtcgtcatcgcagtagattcatctttaaggggcgatttttttgtttta
aacgtgtttcataaatgttgcaatgaaacagggtgattcgtttcatgaaacgttagctgacacgtttttttttccccttaatcgcgcttattc — PprpB promoter sequence
ataacagaaatgactgtaattacctgtttttaaatctcattgtatttaatttctcgctgcctctttgcctggcatagcctttgctttggtga
atacatcttgaataacaatttactaacatgaggacgagatatgtctttacattcgccggggcaggcatttcgcgccgcgctcgctaa — Start codon for *prpB* gene
agagaatccattacaaattgtcggcgctatcaatgccaaccatgctctgttggcccaacgggccgggtatcaggctatctatctttc
tggcggcggcgtagcggcgggctcgctcggactgccggatctggggatttctacgctggatgatgtgttaaccgatatccggcg
catcacggatgtttgcccgctgccgctgttggtggatgcggatattggctttggctcctccgccttttaatgtcgcgcggacggtaaa
gtccatagccaaagcgggcgccgccgcgctgcatattgaagaccaggttggcgctaagcgctgtggacaccgtccaaacaaa
gcgatcgtctcgaaagaggagatggtagaccgaattcgggcggcagtggatgcgcgcaccgatccgaactttgtgatcatggc
gcgtaccgatgcgctggcggtggaagggctggaggcggctctcgatcgtgcgcaggcttacgtggacgcggggggctgacat
gctgttcccggaggcgatcaccgaactgtcgatgtaccgccggttcgccgacgtggcgcaggtgccaatcctcgccaacatca

FIG. 10E ctgagtttggcgcgacgccgctgtttacgaccgacgagttgcgcagcgcacacgtggcgatggcgctctatccgctgtcggcgt
ttcgcgccatgaaccgcgccgcagaaaaagtctataccgtgctgcgccaggaagggacgcaaaagaacgtgatcgacatcat
gcagacccgcaacgagctgtacgaaagcatcaattactaccagttcgaagagaagctggacgcgctgtacaggaataaaaaat
cgtagcctgtaggcctgataaggcgaagccgccatcaggcaatgccggatggcactacgtttaaccccgcctacggtacggcct — Stop codon for *prpB* gene
acacgcctcaataccctacacattacaataatgacgaggacaatatgacagacacgacgatcctgcaaaacaacacgcatgtca — Start codon for *prpC* gene
ttaagcctaaaaaatcggtcgcgctttccggcgtacctgccggaaataccgctctgtgtaccgtgggaaaaagcggtaacgatct
gcactatcgcggttacgacattctcgatctggcggagcactgcgaatttgaagaagtcgcgcatttactgatccacggaaaattac
cgaccgcgacgagctgaacgcgtataaaagcaagttaaaagcgctgcgcggattacccgccaatgtccgtaccgttctggaa
gcgttaccggcggcctcgcacccgatggacgtgatgcgtaccggcgtctccgcgctgggctgcaccctgccggaaaaagag
ggacataccgtctccggcgcgcgcgatattgccgataagctgttggcctcgctcagctctatccttcttttactggtatcactacagc
cacaacggcgaacgtattcagccggaaaccgacgatgattccatcggcggccatttcctgcatctgctgcacggtgaaaagcca
acccaaagctggggaaaaggcgatgcatatttcgctggtgctgtatgccgagcatgagttcaacgcctcgacgtttaccagccgg
gtgattgccgggactggctcggatgtctactccgcgattatcggcgcgattggcgcgctgcgcggcccgaaacacggcgggg
cgaatgaggtgtcgctggaaattcaacagcgttatgaaacgccggacgaggcagaggcggatatccgtaaacgcgtggaaaa
caaagaggtggtgattggctttggacatccggtttacaccatcgccgacccgcgccatcaggtgatcaaacgggtggcgaaac
agctttcagaagaaggcggctcgctgaagatgtaccacatcgccgaccgtctggaaacggtgatgtgggagaccaaaaagatg
ttcccgaatctcgactggttttcggcggtctcctacaacatgatgggcgtccctaccgaaatgttcaccccgctgtttgtcatcgccc
gcgttaccggctgggcggcgcacattattgaacagcgtcaggacaacaaaattattcgccctctgccaactataccgggccgg
aagatcgtccgtttgtctcgatagacgatcgttgctaactcactcttattaaaaataaaacgcaggaaacgtaccctatgtctaccca — Start codon for *prpD* gene / Stop codon for *prpC* gene
agaactgaacatccgcccagactttgaccgtgaaatcgttgatatcgttgattacgttatgaattacgagatcacctcaaaggtggc
gtacgacaccgcgcattattgcctgctcgacacgctcggttgtggtctggaagcgctggaataccggcctgtaaaaaattgctt
gggccaatcgtgccaggcacggtggtgcccaacggcgcacgcgtgccgggcacccagttccagctcgatccggtacaggca
gcttttaacattggcgcgatgatccgctggcttgattttaacgataccctggcttgccgccgagtggggccatccttctgataacctc
ggcggtattctggcgacggctgactggctgtcacgcaacgccgtcgccgccggcaaagcgccgctgaccatgaaacaggtat
tgagcgggatgatcaaagcccatgaaattcaggcgctgcatcgcgctggaaaacgccttcaaccgtgtcggacttgaccatgtgtt
gctggtgaaagtggcctcgactgcggtggtcgctgaaatgctgggggctgacgcgcgatgagatcctcaacgcggtatcgctgg
cgtgggtggatgggcagtcgctgcgtacctatcgtcatgcgccgaataccggtacgcgcaaatcctgggcggcgggcgatgc
gacttcgcgcgcggtacgtctggcgctgatggcgaaaaccggcgagatgggctatccctcggcgctcaccgccaaaacctgg
ggcttctacgacgtttcattcaaaggtgaaacgttccgtttccagcgtccttacggctcctacgtgatggaaaacgtgctattcaaaa
tttctttcccggcagaattccactcgcaaaccgccgtcgaagcggcgatgacgctgtatgagcagatgcaggccgcgggtaaaa
cggcagcggatatcgagaaagtgaccatccgcacccacgaagcctgtctccgcattatcgataaaaaaaggcccgctcaataac
ccggcggaccgcgatcactgtatccagtatatggtcgccgtgccgctgctgttcggacggttaaccgcggcggattatgaagac
gaggtggcgcaggacaagcgtattgacgccctgcgcgagaagatcgtgtgttatgaggacccggcttttaccgccgactatcac
gacccggaaaaacgagctatcggcaatgcgatcaccgtggagtttactgatggatcacgctttggcgaggttgtcgtggagtatc
cgattggtcatgcgcgtcgccgcgccgacggtattccgaagcttatcgaaaaatttaaaattaacctggcgcgtcagttcccgact
cgccagcagcaacgccattctggatgtctccctggacagagccccgcctggagcagatgccgcttaacgaatacctcgatttatatg
tcatctgagccagccagcagtaaggcgtaagttcaacaggagagcgtatgtcttttagcgaattttatcagcgttccattaacgaa — Start codon for *prpE* gene
ccggaggcgttctgggccgagcaggcccggcgttcgactggcgacagccgtttacgcagacgctggatcatagccgtccac
cgtttgcccgctggttttgcggcggcaccactaacttatgtcataacgccgtcgaccgctggcgggataaacagccggaggcgc
tggcgctgattgccgtctcatcagagaccgatgaagagcgcacatttaccttcagccagttgcatgatgaagtcaacattgtggcc — Stop codon for *prpD* gene
gccatgttgctgtcgctgggcgtgcagcgtggcgatcgcgtattggtctatatgccgatgattgccgaagcgcagataaccctgc
tggcctgcgcgcgcattggcgcgatccattcggtggtctttggcggttttgcctcgcacagcgtggcggcgcgcattgacgatgc
cagaccggcgctgattgtctcggcggatgccggagcgcggggcggtaaaatcctgccgtataaaagctgctcgatgacgcta

FIG. 10F ttgcgcaggcgcagcatcagccgaaacacgttctgctggtggacagagggctggcgaaaatggcatgggtggatgggcgcg
atctggattttgccacgttgcgccagcagcatctcggcgcgagcgtgccggtggcgtggctggaatccaacgaaacctcgtgca
ttctttacacctccggcactaccggcaaaccgaaaggcgtccagcgcgacgtcggcggttatgcggtggcgctggcaacctcg
atggacaccatttttggcggcaaggcgggcggcgtattcttttgcgcatcggatatcggctgggtcgtcggccactcctatatcgtt
tacgcgccgttgctggcaggcatggcgactattgtttacgaaggactgccgacgtacccggactgcggggtctggtggaaaatt
gtcgagaaataccaggttaaccggatgttttccgccccgaccgcgattcgcgtgctgaaaaaattcccgacggcgcaaatccgc
aatcacgatctctcctcgctggaggcgctttatctggccggtgagccgctggacgagccgacggccagttgggtaacggagac
gctgggcgtaccggtcatcgacaattattggcagacggagtccggctggccgatcatggcgctggcccgcgcgctggacgac
aggccgtcgcgtctgggaagtcccggcgtgccgatgtacggttataacgtccagctactcaatgaagtcaccggcgaaccttgc
ggcataaatgaaaaggggatgctggtgatcgaagggccgctgccgccgggctgtattcagactatttggggcgacgatgcgcg
ttttgtgaagacttactggtcgctgtttaaccgtcaggtttatgccactttcgactggggaatccgcgacgccgaggggtattacttt
attctgggccgtaccgatgatgtgattaatattgcgggtcatcggctggggacgcgagaaatagaagaaagtatctccagctacc
cgaacgtagcggaagtggcggtagtggggataaaagacgctctgaaagggcaggtagcggtggcgtttgtcattccgaagca
gagcgatacgctggcggatcgcgaggcggcgcgcgacgaggaaaacgcgattatggcgctggtggacaaccagatcggtc
actttggtcgtccggcgcatgtctggtttgtttcgcagctccccaaaacgcgttccggaaagatgcttcgccgcacgatccaggc
gatctgcgaaggccgcgatccgggcgatctgacaaccattgacgatcccgcgtcgttgcagcaaattcgccaggcgatcgaag
aatagccgtaagccggataagccgcgttcggcaacgggttagactcagcgactgaatagtggggtgtaaagtcgggaaaggg
cggcagcgcgccgccctgtaacagaattaa Stop codon for *prpE* gene

FIG. 11 prpR transcriptional activator protein (*E. coli*)

MAHPPRLNDDKPVIWTVSVTRLFELFRDISLEFDHLANITPIQL

GFEKAVTYIRKKLANERCDAIIAAGSNGAYLKSRLSVPVILIKPSGYDVLQALAKAGK

LTSSIGVVTYQETIPALVAFQKTFNLRLDQRSYITEEDARGQINELKANGTEAVVGAG

LITDLAEEAGMTGIFIYSAATVRQAFSDALDMTRMSLRHNTHDATRNALRTRYVLGDM

LGQSPQMEQVRQTILLYARSSAAVLIEGETGTGKELAAQAIHREYFARHDARQGKKSH

PFVAVNCGAIAESLLEAELFGYEEGAFTGSRRGGRAGLFEIAHGGTLFLDEIGEMPLP

LQTRLLRVLEEKEVTRVGGHQPVPVDVRVISATHCNLEEDMQQGRFRRDLFYRLSILR

LQLPPLRERVADILPLAESFLKVSLAALSAPFSAALRQGLQASETVLLHYDWPGNIRE

LRNMMERLALFLSVEPTPDLTPQFMQLLLPELARESAKTPAPRLLTPQQALEKFNGDK

TAAANYLGISRTTFWRRLKS (SEQ ID NO:3)

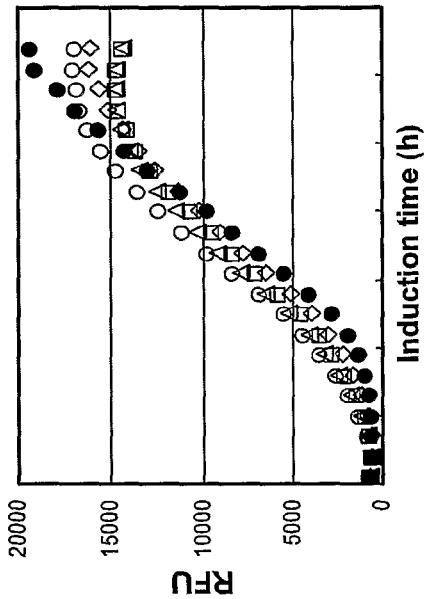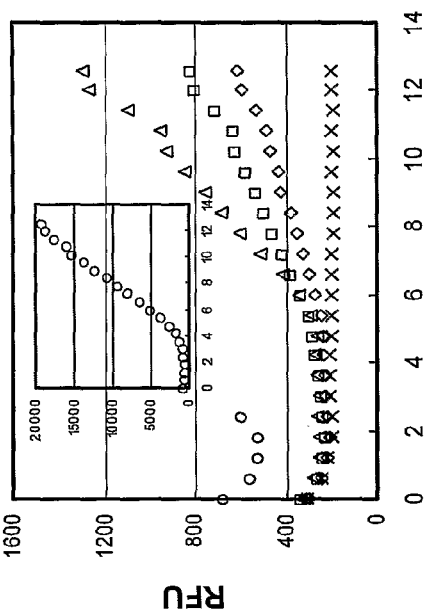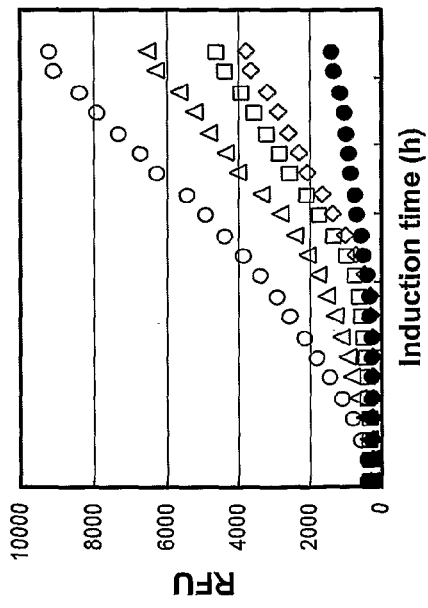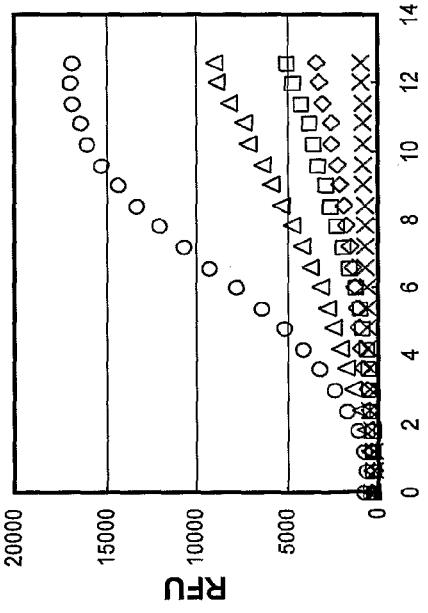

FIG. 16A
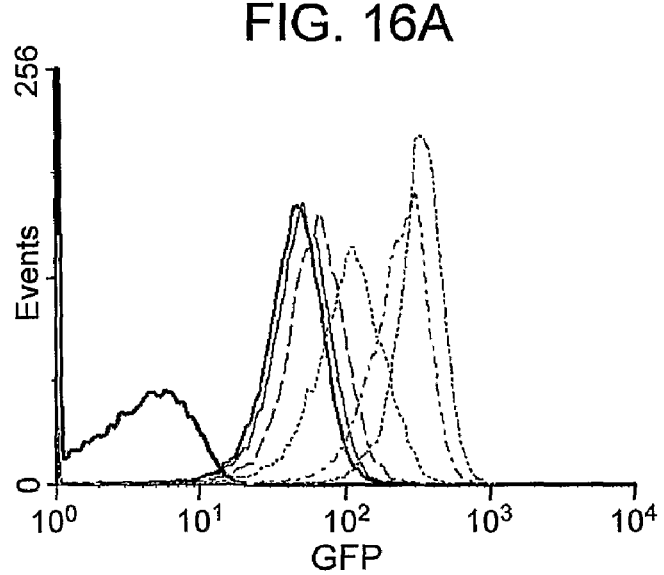
FIG. 16B
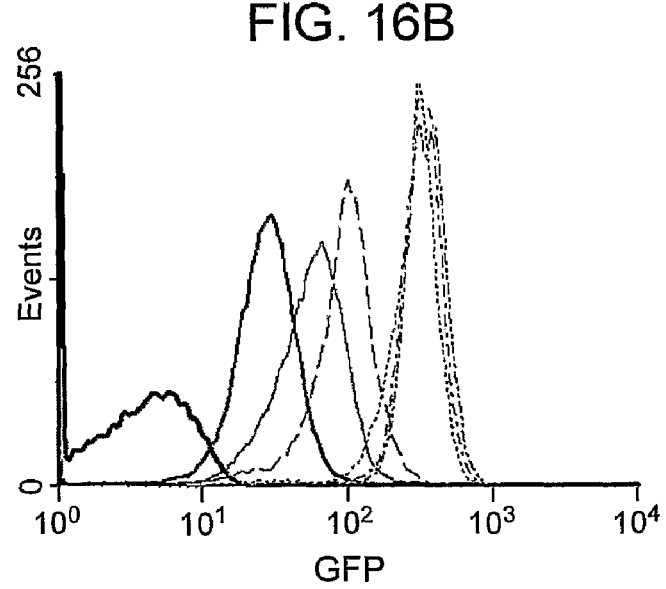
FIG. 16C
| Prop (mM) | C | 0 | 0.02 | 0.08 | 0.32 | 1.25 | 5.0 |
|---|---|---|---|---|---|---|---|
| 0.5% Glc | 90 | 722 | 739 | 949 | 1536 | 3048 | 4266 |
| 0.5% Gly | 90 | 377 | 780 | 1289 | 3465 | 4083 | 4384 |

SEQUENCE LISTING

<160> NUMBER OF SEQ ID NOS: 10

<210> SEQ ID NO 1
<211> LENGTH: 244
<212> TYPE: DNA

```
<213> ORGANISM: Escherichia coli

<400> SEQUENCE: 1
catagcgcac cgcaaagtta agaaaccgaa tattgggttt agtcttgttt cataattgtt      60
gcaatgaaac gcggtgaaac attgcctgaa acgttaactg aaacgcatat ttgcggatta     120
gttcatgact ttatctctaa caaattgaaa ttaaacattt aattttatta aggcaattgt     180
ggcacacccc ttgctttgtc tttatcaacg caaataacaa gttgataaca aggatgggc     240
tatg                                                                  244

<210> SEQ ID NO 2
<211> LENGTH: 271
<212> TYPE: DNA
<213> ORGANISM: Salmonella enterica

<400> SEQUENCE: 2
catcgcagta ggttcatctt taaggggcga ttttttgttt taaacgtgtt tcataaatgt      60
tgcaatgaaa cggagcgatt cgtttcatga aacgttagct gacacgtttt tcttttccct     120
taatcgcgct tattcataac aggaatgact gtaattacct gttttttaaat ctcattgtat   180
ttaattttct cgctgcctct tgcctggca tagcctttgc tttggtgaat acatcttgaa     240
taacaattta ctaacatgag gacgaattat g                                    271

<210> SEQ ID NO 3
<211> LENGTH: 528
<212> TYPE: PRT
<213> ORGANISM: Escherichia coli

<400> SEQUENCE: 3

Met Ala His Pro Pro Arg Leu Asn Asp Asp Lys Pro Val Ile Trp Thr
  1               5                  10                  15

Val Ser Val Thr Arg Leu Phe Glu Leu Phe Arg Asp Ile Ser Leu Glu
                 20                  25                  30

Phe Asp His Leu Ala Asn Ile Thr Pro Ile Gln Leu Gly Phe Glu Lys
             35                  40                  45

Ala Val Thr Tyr Ile Arg Lys Lys Leu Ala Asn Glu Arg Cys Asp Ala
         50                  55                  60

Ile Ile Ala Ala Gly Ser Asn Gly Ala Tyr Leu Lys Ser Arg Leu Ser
 65                  70                  75                  80

Val Pro Val Ile Leu Ile Lys Pro Ser Gly Tyr Asp Val Leu Gln Ala
                 85                  90                  95

Leu Ala Lys Ala Gly Lys Leu Thr Ser Ser Ile Gly Val Val Thr Tyr
            100                 105                 110

Gln Glu Thr Ile Pro Ala Leu Val Ala Phe Gln Lys Thr Phe Asn Leu
        115                 120                 125

Arg Leu Asp Gln Arg Ser Tyr Ile Thr Glu Glu Asp Ala Arg Gly Gln
    130                 135                 140

Ile Asn Glu Leu Lys Ala Asn Gly Thr Glu Ala Val Val Gly Ala Gly
145                 150                 155                 160

Leu Ile Thr Asp Leu Ala Glu Glu Ala Gly Met Thr Gly Ile Phe Ile
                165                 170                 175

Tyr Ser Ala Ala Thr Val Arg Gln Ala Phe Ser Asp Ala Leu Asp Met
            180                 185                 190

Thr Arg Met Ser Leu Arg His Asn Thr His Asp Ala Thr Arg Asn Ala
        195                 200                 205

Leu Arg Thr Arg Tyr Val Leu Gly Asp Met Leu Gly Gln Ser Pro Gln
```

```
              210                 215                 220
Met Glu Gln Val Arg Gln Thr Ile Leu Leu Tyr Ala Arg Ser Ser Ala
225                 230                 235                 240

Ala Val Leu Ile Glu Gly Glu Thr Gly Thr Gly Lys Glu Leu Ala Ala
                245                 250                 255

Gln Ala Ile His Arg Glu Tyr Phe Ala Arg His Asp Ala Arg Gln Gly
                    260                 265                 270

Lys Lys Ser His Pro Phe Val Ala Val Asn Cys Gly Ala Ile Ala Glu
                275                 280                 285

Ser Leu Leu Glu Ala Glu Leu Phe Gly Tyr Glu Glu Gly Ala Phe Thr
290                 295                 300

Gly Ser Arg Arg Gly Gly Arg Ala Gly Leu Phe Glu Ile Ala His Gly
305                 310                 315                 320

Gly Thr Leu Phe Leu Asp Glu Ile Gly Glu Met Pro Leu Pro Leu Gln
                325                 330                 335

Thr Arg Leu Leu Arg Val Leu Glu Glu Lys Glu Val Thr Arg Val Gly
                340                 345                 350

Gly His Gln Pro Val Pro Val Asp Val Arg Val Ile Ser Ala Thr His
                355                 360                 365

Cys Asn Leu Glu Glu Asp Met Gln Gln Gly Arg Phe Arg Arg Asp Leu
370                 375                 380

Phe Tyr Arg Leu Ser Ile Arg Leu Gln Leu Pro Pro Leu Arg Glu
385                 390                 395                 400

Arg Val Ala Asp Ile Leu Pro Leu Ala Glu Ser Phe Leu Lys Val Ser
                405                 410                 415

Leu Ala Ala Leu Ser Ala Pro Phe Ser Ala Ala Leu Arg Gln Gly Leu
                420                 425                 430

Gln Ala Ser Glu Thr Val Leu Leu His Tyr Asp Trp Pro Gly Asn Ile
                435                 440                 445

Arg Glu Leu Arg Asn Met Met Glu Arg Leu Ala Leu Phe Leu Ser Val
                450                 455                 460

Glu Pro Thr Pro Asp Leu Thr Pro Gln Phe Met Gln Leu Leu Leu Pro
465                 470                 475                 480

Glu Leu Ala Arg Glu Ser Ala Lys Thr Pro Ala Pro Arg Leu Leu Thr
                485                 490                 495

Pro Gln Gln Ala Leu Glu Lys Phe Asn Gly Asp Lys Thr Ala Ala Ala
                500                 505                 510

Asn Tyr Leu Gly Ile Ser Arg Thr Thr Phe Trp Arg Arg Leu Lys Ser
                515                 520                 525

<210> SEQ ID NO 4
<211> LENGTH: 1170
<212> TYPE: DNA
<213> ORGANISM: Salmonella typhimurium

<400> SEQUENCE: 4
atgacagaca cgacgatcct gcaaaacaac acgcatgtca ttaagcctaa aaaatcggtc      60
gcgctttccg gcgtacctgc cggaaatacc gctctgtgta ccgtgggaaa aagcggtaac     120
gatctgcact atcgcggtta cgacattctc gatctggcgg agcactgcga atttgaagaa     180
gtcgcgcatt tactgatcca cggaaaatta ccgacccgcg acgagctgaa cgcgtataaa     240
agcaagttaa aagcgctgcg cggattaccc gccaatgtcc gtaccgttct ggaagcgtta     300
ccggcggcct cgcacccgat ggacgtgatg cgtaccggcg tctccgcgct gggctgcacc     360
ctgccggaaa agagggaca taccgtctcc ggcgcgcgcg atattgccga taagctgttg     420
```

| | | | | |
|---|---|---|---|---|
| gcctcgctca | gctctatcct | tctttactgg | tatcactaca | gccacaacgg cgaacgtatt | 480 |
| cagccggaaa | ccgacgatga | ttccatcggc | ggccatttcc | tgcatctgct gcacggtgaa | 540 |
| aagccaaccc | aaagctggga | aaaggcgatg | catatttcgc | tggtgctgta tgccgagcat | 600 |
| gagttcaacg | cctcgacgtt | taccagccgg | gtgattgccg | ggactggctc ggatgtctac | 660 |
| tccgcgatta | tcggcgcgat | tggcgcgctg | cgcggcccga | acacggcgg ggcgaatgag | 720 |
| gtgtcgctgg | aaattcaaca | gcgttatgaa | acgccggacg | aggcagaggc ggatatccgt | 780 |
| aaacgcgtgg | aaaacaaaga | ggtggtgatt | ggctttggac | atccggttta caccatcgcc | 840 |
| gacccgcgcc | atcaggtgat | caaacgggtg | gcgaaacagc | tttcagaaga aggcggctcg | 900 |
| ctgaagatgt | accacatcgc | cgaccgtctg | gaaacggtga | tgtgggagac caaaaagatg | 960 |
| ttcccgaatc | tcgactggtt | ttcggcggtc | tcctacaaca | tgatgggcgt ccctaccgaa | 1020 |
| atgttcaccc | cgctgtttgt | catcgcccgc | gttaccggct | gggcggcgca cattattgaa | 1080 |
| cagcgtcagg | acaacaaaat | tattcgcccc | tctgccaact | ataccgggcc ggaagatcgt | 1140 |
| ccgtttgtct | cgatagacga | tcgttgctaa | | | 1170 |

<210> SEQ ID NO 5
<211> LENGTH: 7606
<212> TYPE: DNA
<213> ORGANISM: Escherichia coli

<400> SEQUENCE: 5

| | | | | |
|---|---|---|---|---|
| tatcggtgat | catctattga | aatttatgcc | ggataaagcg | ttcgcgctgc attcggcagt | 60 |
| tcagcttttc | agccgccgcc | agaacgtcgt | ccggctgatg | cctaaataat tcgccgctgc | 120 |
| tgttttatcg | ccattaaatt | tctccagtgc | ctgttgtggt | gtcagtaagc gtggagcggg | 180 |
| agttttcgcc | gactcgcgcg | ccagttccgg | cagtagcagt | tgcataaact gcggcgttaa | 240 |
| atccggcgtc | ggttccacac | ttaaaaacag | cgccagtcgt | tccatcatat tgcgcagttc | 300 |
| acgaatattg | cctggccagt | cgtagtgcag | cagcacagtt | tcacttgcct gtaaccctg | 360 |
| gcgtaatgca | gcagaaaatg | gggcggagag | cgccgccaga | gacactttca aaaagctttc | 420 |
| cgccagcgga | agaatatccg | ccacccgctc | gcgcagtggt | ggcaattgca gacgcaaaat | 480 |
| actcagccga | taaaacagat | cacggcgaaa | acgtccttgc | tgcatatctt cttccagatt | 540 |
| gcagtgagtg | gcgctaatga | cccgtacatc | taccggaaca | ggctgatgcc cgccgacgcg | 600 |
| ggtgacctct | ttttcttcca | gcacccgcag | cagcccgggtc | tgcaaaggta gcggcatttc | 660 |
| gccaatctca | tccagaaaca | gcgtaccgcc | gtgggcaatt | tcgaacagcc cggcgcgacc | 720 |
| tccgcgtcgc | gagccggtaa | acgccccttc | ctcatagcca | aacagttctg cttccagcag | 780 |
| cgattcggca | atcgccccgc | agttgacggc | aacaaacgga | tgcgactttt tgccctgtcg | 840 |
| cgcatcgtgg | cgggcaaaat | attcccgatg | aatcgcctgg | gccgccagct ctttgcccgt | 900 |
| ccccgttttcc | ccctcaatca | acaccgccgc | actggagcgg | gcatacagca aaatagtctg | 960 |
| ccgtacttgt | tccatctgtg | gtgattgacc | gagcatatcg | cccagcacgt aacgagtacg | 1020 |
| cagggcgttg | cgggtggcat | cgtgagtgtt | atggcgtaac | gacatgcgcg tcatatccag | 1080 |
| cgcatcgctg | aacgcctggc | gcacggtggc | ggcggaatag | ataaaaattc cggtcattcc | 1140 |
| ggcttcttct | gccaaatcgg | taatcagccc | tgcgccgacc | accgcttcgg tgccgttagc | 1200 |
| ttttagctcg | ttaatctgcc | cgcgtgcgtc | ttcctcggta | atgtagctac gttggtcgag | 1260 |
| gcgcaaatta | aaggtttttt | gaaacgccac | cagcgctgga | atggtttcct gataggtgac | 1320 |
| aacgccgata | gaagaggtga | gttttccggc | ttttgccagt | gcctgtaaca catcgtagcc | 1380 |

```
gctcggttta atcaaaataa ctggcactga caggcggctt ttcaggtacg cgccgttaga   1440
gccagccgcg atgatggcgt cacagcgttc gtttgccagt ttcttgcgga tgtaggtcac   1500
tgcttttta  aagccaagct gaatagggt  aatgttcgcc aggtgatcaa actcgaggct   1560
gatatcgcga aacagctcga acaggcgcgt tacagatacc gtccagataa ccggtttgtc   1620
gtcattaagc cgtggtggat gtgccatagc gcaccgcaaa gttaagaaac cgaatattgg   1680
gtttagtctt gtttcataat tgttgcaatg aaacgcggtg aaacattgcc tgaaacgtta   1740
actgaaacgc atatttgcgg attagttcat gactttatct ctaacaaatt gaaattaaac   1800
atttaattt  attaaggcaa ttgtggcaca ccccttgctt tgtctttatc aacgcaaata   1860
acaagttgat aacaaaggat gggctatgtc tctacactct ccaggtaaag cgtttcgcgc   1920
tgcactgact aaagaaaatc cattgcagat tgttggcacc atcaacgcta atcatgcgct   1980
gttggcgcag cgtgccggat atcaggcaat ttatctttct ggcggtggcg tggcggcagg   2040
ttcgctgggg ctgcccgatc tcggtatttc taccccttgat gatgtgctga ccgacattcg   2100
ccgtatcacc gacgtttgtt cgctgccgct gctggtggat gcggatatcg gttttggttc   2160
ttcggccttt aacgtggcgc gcaccgtgaa atcgatgatt aaagccggtg cggcaggatt   2220
gcatattgaa gatcaggttg gtgcgaaacg ctgcggtcat cgtccgaata aagcgatcgt   2280
ctcgaaagaa gagatggtgg atcggatccg cgcggcggtg gatgcgaaaa ccgatcctga   2340
ttttgtgatc atggcgcgca ccgatgctct ggcggtagag gggctggatg cggcgatcga   2400
gcgtgcgcag gcctatgttg aagcgggtgc cgagatgttg ttcccggagg cgattaccga   2460
actcgccatg taccgccagt ttgccgatgc ggtgcaggtg ccgatcctcg ccaacatcac   2520
cgaatttggt gccacgccgc tgtttaccac cgacgaatta cgcagcgccc atgtcgcaat   2580
ggcgctgtac ccactttcag cgttccgcgc catgaaccgc gccgctgaac atgtctacaa   2640
cgtcctgcgc caggaaggca cgcagaaaag cgtcatcgac accatgcaga cccgcaacga   2700
gctgtacgaa agcatcaact actaccagta cgaagagaag ctcgacaacc tgtttgcccg   2760
tagccaggta aaataaaaaa cgcccgttga ttgtattcga cagccgatgc ctgatgcgtc   2820
gctgacgcga cttatcaggc ctacgaggtg cactgaactg taggtcggat aagacggatg   2880
gcgtcgcatc cgacaaccga tgcctgatgc gccgctgacg tgacttatca ggcctacggg   2940
gtgcactgaa ctgtaggtcg gataagacgc atagcgtcgc atccgacaac cgatgcctga   3000
tgcgccgctg acgcgactta tcaggcctac ggggtgcact gaactgtagg tcggataaga   3060
cgcatagcgt cgcatccgac aaccgatgcc tgatgcgccg ctgacgcgac ttatcaggcc   3120
tacggggtga actgaactgt aggtcggata agacgcatag cgtcgcatcc gacaacaatc   3180
tcgaccctac aaatgataac aatgacgagg acaacatgag cgacacaacg atcctgcaaa   3240
acagtaccca tgtcattaaa ccgaaaaaat ctgtggcact ttctggcgtt ccggcgggca   3300
atacggcgct ctgcaccgtg gtaaaagtg  gcaatgacct gcattaccgc ggctacgata   3360
ttcttgatct ggcgaaacat tgcgaatttg aagaagtggc gcatctgctg atccacggca   3420
aactgccgac ccgtgacgaa ctcgccgctt acaaaacgaa actgaaagcc ctgcgcggtt   3480
taccggctaa cgtgcgtacc gtgctggaag ccttaccggc ggcgtcgcac ccgatggatg   3540
ttatgcgcac cggtgtttcc gcgctcggct gcacgctgcc agaaaaagag gggcataccg   3600
tctctgcgcg cgcgggatat tgccgacaaac tgctggcgtc gcttagctcg attctccttt   3660
attggtatca ctacagccac aacgcgcgaac gcatccaacc ggaaaccgat gacgactcca   3720
tcggcggtca cttcctgcat ctgctgcacg gcgaaaagcc atcgcaaagc tgggaaaagg   3780
```

```
cgatgcatat ctcgctggtg ctgtacgccg aacacgagtt taacgcctcc acctttacca   3840
gtcgggtgat tgcgggcacc ggctctgata tgtattccgc gattattggc gcgattggcg   3900
cactgcgcgg gccaaaacac ggcggggcga atgaagtgtc gctggagatc cagcaacgct   3960
acgaaacgcc ggacgaagcc gaagcagata tccgcaagcg cgtggaaaac aaagaagtgg   4020
tcattggttt tggtcatccg gtttacacca tcgctgaccc gcgccaccag gtgattaaac   4080
gtgtggcgaa gcagctctcg caggaaggcg gctcgctgaa gatgtacaac atcgccgatc   4140
gcctggaaac ggtgatgtgg gagagcaaaa agatgttccc caatctcgac tggttctctg   4200
ctgtttccta caacatgatg ggcgttccca ccgagatgtt cacaccactg tttgttatcg   4260
cccgcgtcac cggctgggcg cgcacatta tcgaacaacg tcaggacaac aaaattatcc   4320
gtccttccgc caattatgtt ggaccggaag accgcccgtt tgtcgcgctg ataagcgcc   4380
agtaaacctc tacgaataac aataaggaaa cgtacccaat gtcagctcaa atcaacaaca   4440
tccgcccgga atttgatcgt gaaatcgttg atatcgtcga ttacgtcatg aactacgaaa   4500
tcagctctaa agtggcctac gacaccgcac attactgcct gctcgacacg ctcggctgcg   4560
gtctggaagc tctcgaatac ccggcctgta aaaaactgct ggggccaatt gttcccggca   4620
ccgtcgtacc caacggcgtg cgcgtccccg gaactcagtt ccagctcgac cccgtccagg   4680
cggcatttaa catcggcgcg atgatccgct ggctcgattt caacgatacc tggctggcgg   4740
cggagtgggg ccatccttcc gacaacctcg gcggcattct ggcaacggcg gactggcttt   4800
cgcgcaacgc ggtcgccagc ggcaaagcgc cgttgaccat gaaacaggtg ctgaccgcaa   4860
tgatcaaagc ccatgaaatt cagggctgca tcgcgctgga aaactccttt aaccgcgtcg   4920
gcctcgacca cgttctgtta gtgaaagtgg cttccaccgc cgtggtcgcc gaaatgctcg   4980
gcctgacccg cgaggaaatt ctcaacgccg tttcgctggc gtgggtggac ggtcagtcgc   5040
tgcgcaccta tcgccatgcg ccgaacaccg gcacgcgtaa atcctgggcg cgggcgatg   5100
ccacttcccg cgcggtacgt ctggcactga tggcgaaaac gggcgaaatg ggttacccgt   5160
cagccctgac tgcgccggtg tggggcttct acgacgtctc ctttaaaggt gaatcgttcc   5220
gcttccagcg cccgtacggt tcctacgtta tggaaaatgt gctgttcaaa atctccttcc   5280
cggcggagtt ccactcccag acggcagttg aagcagcgat gacgctctat gaacagatgc   5340
aggcagcagg caaaacggcg gcggatatcg aaaaagtgac cattcgcacc cacgaagcct   5400
gtattcgcat catcgacaaa aaagggccgc tcaataaccc ggcagaccgc gatcactgca   5460
ttcagtacat ggtggcgatc ccgctgctat tcgggcgctt aacggcggca gattacgagg   5520
acaacgttgc gcaagataaa cgcattgacg ccctgcgcga agatcaat tgctttgaag   5580
atccggcatt taccgctgac taccacgacc cggaaaaacg cgccatcgcc aatgccatta   5640
cccttgagtt caccgacggc acacgatttg aagaagtggt ggtggagtac cccattggtc   5700
atgctcgccg ccgtcaggat ggtattccga aactggtcga taaattcaaa atcaatctcg   5760
cgcgccagtt cccgactcgc caacagcagc gcattctgga ggtttctctc gacagagctc   5820
gcctggaaca gatgccggtc aatgagtatc tcgacctgta cgtcatttaa gtaaacggcg   5880
gtaaggcgta agttcaacag gagagcatta tgtcttttag cgaattttat cagcgttcga   5940
ttaacgaacc ggagcagttc tgggccgagc aggcccggcg tattgactgg cagacgcgcct   6000
ttacgcaaac gctcgatcac agcaatccgc cgtttgcccg ttggttttgt gaaggccgaa   6060
ccaacttgtg ccacaacgcc atcgaccgct ggctggagaa acagccagag gcgctggcgc   6120
tgattgccgt ctcttcggaa acagaagaag agcgcacctt tacctttcgt cagctgcatg   6180
```

```
acgaagtgaa cgcggtggcc tcaatgttgc gttcattggg tgtgcagcgc ggcgatcggg    6240
tgctggtgta tatgccgatg attgccgaag cgcatattac tctgctggcc tgcgcgcgca    6300
ttggcgctat tcactcggtg gtgtttggtg gatttgcctc gcacagcgtg gcggcgcgaa    6360
ttgatgacgc taaaccggtg ctgattgtct cggctgatgc cggagcgcgc ggtggcaaaa    6420
tcattcccta taaaaaattg ctcgacgatg cgataagtca ggcgcagcac cagccacgcc    6480
atgttttgct ggtggatcgc gggctggcga aaatggcgcg cgtcagcggg cgggatgtcg    6540
atttcgcgtc gttgcgccat caacacatcg gcgcgcgggt accggtggcg tggctggaat    6600
ccaacgaaac ctcctgcatt tctctacactt ccggcacgac cggcaaacct aaaggcgtgc    6660
agcgtgacgt cggcggatat gcggtggcgc tggcgacctc gatggacacc attttttggcg    6720 gcaaagcggg cagcgtgttc ttttgcgcat cggatatcgg ctgggtggtg gggcattcgt    6780
atatcgttta cgcgccgctg ctggcgggga tggcgactat cgtttacgaa ggattgccga    6840
cctggccgga ctgcggcgtg tggtggacaa tcgtcgagaa atatcaggtt agccggatgt    6900
tctcagcgcc gaccgccatt cgcgtgctga aaaaattccc taccgctgaa attcgcaaac    6960
acgatctctc gtcgctggaa gtgctctatc tggctggaga accgctggac gagccgaccg    7020
ccagttgggt gagcaatacg ctggatgtgc cggtcatcga caactactgg cagaccgaat    7080
ccggctggcc gattatggcg attgctcgcg gtctggacga caggccgacg cgtctgggaa    7140
gccccggtgt gccgatgtat ggctataacg tgcagttgct taatgaagtc accggcgaac    7200
cgtgtggcgt caacgagaaa gggatgctgg tggtggaagg gccgctgccg ccggggtgta    7260
ttcagaccat ctggggcgac gacggccgct tgtgaagac ttactggtcg ctgttttccc    7320
gcccggtgta cgccacccttt gactggggca tccgtgacgc tgacggttat cactttattc    7380
tcgggcgcac tgacgatgta attaacgttg ccgggcatcg gctggggacg cgcgagattg    7440
aagagagtat ctccagccat ccggggcgttg ccgaagtggc ggtggttggg gtgaaagatg    7500
cgctgaaagg gcaggtggcg gtggcgtttg tcattccgaa agagagcgac agtctggaag    7560
atcgtgatgt ggcgcactcg caagagaagg cgattatggc gctggt               7606
```

<210> SEQ ID NO 6
<211> LENGTH: 7627
<212> TYPE: DNA
<213> ORGANISM: Salmonella typhimurium

<400> SEQUENCE: 6

```
gccatcaggc attcaggacg ctgtcatttg tcttaattat ccgactggtc tttggcacca      60
gcttttaaac gacgccacag agtggtgcgg ctaatcccca gataacgcgc cgcggcggtc     120
ttatcgccct taaagcgcgc cagtacatcc tgtaacgcgt tcgcatccac ggttgaaggc     180
gtcagttctg ctgtgttcac cataagctca ggtaataact gccgcataaa ttgcctgtcc     240
agcgttggcg cgggatcgac gcttaaaaaa agcgccaggc gctccatcat attacgcagt     300
tcgcgaatat taccgggcca gcgccaggcc agcaaaagcg gctgacactg tgtcaatcca     360
tgacgtatcg attcggtaaa cggaatttcc atcgccgcca gcgactgttt taaaaagctt     420
tccgccagcg gcaaaatatc agcctgccgc tcgcgcaaag gaggaagcgt cagacgcaga     480
atactcaggc gataaaagag atcggggcga aacgtccctt gcattatctc ccgatccaga     540 tgcaatgcg tagcgctgat cacccggaca tccaccggga tcggctggtg tccgccgacg     600
cgagtgacgc cttttttcctc cagtacgcgc aaaagtcggg tttgtaacgg caagggcatt     660
tcgccgattt catccagaaa cagcgtgccg ccgtgtgcga tttcaaacag ccccgcccgg     720
```

```
cctcctcgtc gtgaaccggt aaacgcgccc tcttcataac caaacagttc cgcttccagc    780
aacgactcgg taatcgcgcc gcaattgacg gcgacaaagg gaggggatgg cttattctga    840
cggtgaggct ggcggtgaaa gaacgtctgg tgaatcgcct gcgccgccag ctcttttccg    900
gtccctgttt ccccctgaat cagcactgcc gcacgggagc gggcatagag cgtaatcgtc    960
tggcggagct gctccatttg cggcgactgg ccgcgtatat cgcccagttc ataccgggtt   1020
tgtaatccct tgccggatgg gtaatccacg cgctggcgcc gtgtcagacg ggtcatatcc   1080
agcgcatcat gaaaagcctg acgaacggtc gccgcggaat aaataaagat ggcggtcatt   1140
cctgcctctt ccgccagatc ggtaattaat cccgcgccga cgacggcctc aataccgttg   1200
gccttaagtt cgttaatttg cccgcgcgcg tcctcttcgg tgacatagct tcgctgttca   1260
agacggaggt gaaacgtttt ctgaaaggca agtaaagccg gaatggtctc ctgataggtc   1320
acgataccga tagacgaggt gagctttccc gctttcgcca gcgcctgtaa tacatcgaat   1380
ccgctgggct tgatgaggat caccggtatt gacaggcggc ttttttaaata ggccccattc   1440
gaacccgccg cgataatcgc gtcgcagcgc tcggtcgcca gttttttgcg aatgtaggtc   1500
accgcctttt caaagccgag ttgaataggc gtgatggtcg ccagatgatc gaattccagg   1560
ctgatatccc gaaacagttc gaacagacgc gttacggaga ccgtccagat caccggttta   1620
tcgctattat cgcgcggagc gctgtgggca gtcgtcatcg cagtagattc atctttaagg   1680
ggcgattttt tgttttaaac gtgtttcata aatgttgcaa tgaaacaggg tgattcgttt   1740
catgaaacgt tagctgacac gttttttttt cccttaatcg cgcttattca taacagaaat   1800
gactgtaatt acctgttttt aaatctcatt gtatttaatt ttctcgctgc ctctttgcct   1860
ggcatagcct ttgctttggt gaatacatct tgaataacaa tttactaaca tgaggacgag   1920
atatgtcttt acattcgccg gggcaggcat ttcgcgccgc gctcgctaaa gagaatccat   1980
tacaaattgt cggcgctatc aatgccaacc atgctctgtt ggcccaacgg gccgggtatc   2040
aggctatcta tcttttctggc ggcggcgtag cggcgggctc gctcggactg ccggatctgg   2100
ggatttctac gctggatgat gtgttaaccg atatccggcg catcacggat gtttgccccgc   2160
tgccgctgtt ggtggatgcg gatattggct ttggctcctc cgcctttaat gtcgcgcgga   2220
cggtaaagtc catagccaaa gcgggcgccg ccgcgctgca tattgaagac caggttggcg   2280
ctaagcgctg tggacaccgt ccaaacaaag cgatcgtctc gaaagaggag atggtagacc   2340
gaattcgggc ggcagtggat gcgcgcaccg atccgaactt tgtgatcatg gcgcgtaccg   2400
atgcgctggc ggtggaaggg ctggaggcgg ctctcgatcg tgcgcaggct tacgtggacg   2460
cgggggctga catgctgttc ccggaggcga tcaccgaact gtcgatgtac cgccggttcg   2520
ccgacgtggc gcaggtgcca atcctcgcca acatcactga gtttggcgcg acgccgctgt   2580
ttacgaccga cgagttgcgc agcgcacacg tggcgatggc gctctatccg ctgtcggcgt   2640
ttcgcgccat gaaccgcgcc gcagaaaaag tctataccgt gctgcgccag gaagggacgc   2700
aaaagaacgt gatcgacatc atgcagaccc gcaacgagct gtacgaaagc atcaattact   2760
accagttcga agagaagctg gacgcgctgt acaggaataa aaaatcgtag cctgtaggcc   2820
tgataaggcg aagccgccat caggcaatgc cggatggcac tacgtttaac ccgcctacgg   2880
tacgcctac acgcctcaat accctacaca ttacaataat gacgaggaca atatgacaga   2940
cacgacgatc ctgcaaaaca acacgcatgt cattaagcct aaaaaatcgg tcgcgctttc   3000
cggcgtacct gccggaaata ccgctctgtg taccgtggga aaaagcggta acgatctgca   3060
ctatcgcggt tacgacattc tcgatctggc ggagcactgc gaatttgaag aagtcgcgca   3120
```

```
tttactgatc cacggaaaat taccgacccg cgacgagctg aacgcgtata aaagcaagtt   3180
aaaagcgctg cgcggattac ccgccaatgt ccgtaccgtt ctggaagcgt taccggcggc   3240
ctcgcacccg atggacgtga tgcgtaccgg cgtctccgcg ctgggctgca ccctgccgga   3300
aaaagaggga cataccgtct ccggcgcgcg cgatattgcc gataagctgt tggcctcgct   3360
cagctctatc cttctttact ggtatcacta cagccacaac ggcgaacgta ttcagccgga   3420
aaccgacgat gattccatcg gcggccattt cctgcatctg ctgcacggtg aaaagccaac   3480
ccaaagctgg gaaaaggcga tgcatatttc gctggtgctg tatgccgagc atgagttcaa   3540
cgcctcgacg tttaccagcc gggtgattgc cgggactggc tcggatgtct actccgcgat   3600
tatcggcgcg attggcgcgc tgcgcggccc gaaacacggc ggggcgaatg aggtgtcgct   3660
ggaaattcaa cagcgttatg aaacgccgga cgaggcagag gcgatatcc gtaaacgcgt   3720 ggaaaacaaa gaggtggtga ttggctttgg acatccggtt tacaccatcg ccgacccgcg   3780
ccatcaggtg atcaaacggg tggcgaaaca gctttcagaa gaaggcggct cgctgaagat   3840
gtaccacatc gccgaccgtc tggaaacggt gatgtgggag accaaaaaga tgttcccgaa   3900
tctcgactgg ttttcggcgg tctcctacaa catgatgggc gtccctaccg aaatgttcac   3960
cccgctgttt gtcatcgccc gcgttaccgg ctgggcggcg cacattattg aacagcgtca   4020
ggacaacaaa attattcgcc cctctgccaa ctataccggg ccggaagatc gtccgtttgt   4080
ctcgatagac gatcgttgct aactcactct tattaaaaat aaaacgcagg aaacgtaccc   4140
tatgtctacc caagaactga acatccgccc agactttgac cgtgaaatcg ttgatatcgt   4200
tgattacgtt atgaattacg agatcaccctc aaaggtggcg tacgacaccg cgcattattg   4260
cctgctcgac acgctcggtt gtggtctgga agcgctggaa tacccggcct gtaaaaaatt   4320
gcttgggcca atcgtgccag gcacggtggt gcccaacggc gcacgcgtgc cgggcaccca   4380
gttccagctc gatccggtac aggcagcttt taacattggc gcgatgatcc gctggcttga   4440
ttttaacgat acctggcttg ccgccgagtg gggccatcct tctgataacc tcggcggtat   4500
tctggcgacg gctgactggc tgtcacgcaa cgccgtcgcc gccggcaaag cgccgctgac   4560
catgaaacag gtattgagcg ggatgatcaa agcccatgaa attcagggct gcatcgcgct   4620
ggaaaacgcc ttcaaccgtg tcggacttga ccatgtgttg ctggtgaaag tggcctcgac   4680
tgcggtggtc gctgaaatgc tggggctgac gcgcgatgag atcctcaacg cggtatcgct   4740
ggcgtgggtg gatgggcagt cgctgcgtac ctatcgtcat gcgccgaata ccggtacgcg   4800
caaatcctgg gcggcgggcg atgcgacttc gcgcgcggta cgtctggcgc tgatggcgaa   4860
aaccggcgag atgggctatc cctcggcgct caccgccaaa acctgggget tctacgacgt   4920 ttcattcaaa ggtgaaacgt tccgtttcca gcgtccttac ggctcctacg tgatggaaaa   4980
cgtgctattc aaaatttctt tcccggcaga attccactcg caaaccgccg tcgaagcggc   5040
gatgacgctg tatgagcaga tgcaggccgc gggtaaaacg gcagcggata tcgagaaagt   5100
gaccatccgc acccacgaag cctgtctccg cattatcgat aaaaaaggcc cgctcaataa   5160
cccggcggac cgcgatcact gtatccagta tatggtcgcc gtgccgctgc tgttcggacg   5220
gttaaccgcg gcggattatg aagacgaggt ggcgcaggac aagcgtattg acgccctgcg   5280
cgagaagatc gtgtgttatg aggacccggc ttttaccgcc gactatcacg cccggaaaa   5340 acgagctatc ggcaatgcga tcaccgtgga gtttactgat ggatcacgct ttggcgaggt   5400
tgtcgtggag tatccgattg gtcatgcgcg tcgccgcgcc gacggtattc cgaagcttat   5460
cgaaaaattt aaaattaacc tggcgcgtca gttcccgact cgccagcagc aacgcattct   5520
```

```
ggatgtctcc ctggacagag cccgcctgga gcagatgccg gttaacgaat acctcgattt    5580
atatgtcatc tgagccagcc agcagtaagg cgtaagttca acaggagagc gtgatgtctt    5640
ttagcgaatt ttatcagcgt tccattaacg aaccggaggc gttctgggcc gagcaggccc    5700
ggcgtatcga ctggcgacag ccgtttacgc agacgctgga tcatagccgt ccaccgtttg    5760
cccgctggtt ttgcggcggc accactaact tatgtcataa cgccgtcgac cgctggcggg    5820
ataaacagcc ggaggcgctg gcgctgattg ccgtctcatc agagaccgat gaagagcgca    5880
catttacctt cagccagttg catgatgaag tcaacattgt ggccgccatg ttgctgtcgc    5940
tgggcgtgca gcgtggcgat cgcgtattgg tctatatgcc gatgattgcc gaagcgcaga    6000
taaccctgct ggcctgcgcg cgcattggcg cgatccattc ggtggtcttt ggcggttttg    6060
cctcgcacag cgtggcggcg cgcattgacg atgccagacc ggcgctgatt gtgtcggcgg    6120
atgccggagc gcggggcggt aaaatcctgc cgtataaaaa gctgctcgat gacgctattg    6180
cgcaggcgca gcatcagccg aaacacgttc tgctggtgga cagagggctg gcgaaaatgg    6240
catgggtgga tgggcgcgat ctggattttg ccacgttgcg ccagcagcat ctcggcgcga    6300
gcgtgccggt ggcgtggctg gaatccaacg aaacctcgtg cattctttac acctccggca    6360
ctaccggcaa accgaaaggc gtccagcgcg acgtcggcgg ttatgcggtg gcgctggcaa    6420
cctcgatgga caccatttttt ggcggcaagg cgggcggcgt attctttttgc gcatcggata    6480 tcggctgggt cgtcggccac tcctatatcg tttacgcgcc gttgctggca ggcatggcga    6540
ctattgttta cgaaggactg ccgacgtacc cggactgcgg ggtctggtgg aaaattgtcg    6600
agaaatacca ggttaaccgg atgttttccg ccccgaccgc gattcgcgtg ctgaaaaaat    6660
tcccgacggc gcaaatccgc aatcacgatc tctcctcgct ggaggcgctt tatctggccg    6720
gtgagccgct ggacgagccg acggccagtt gggtaacgga gacgctgggc gtaccggtca    6780
tcgacaatta ttggcagacg gagtccggct ggccgatcat ggcgctggcc cgcgcgctgg    6840
acgacaggcc gtcgcgtctg ggaagtcccg gcgtgccgat gtacggttat aacgtccagc    6900
tactcaatga agtcaccggc gaaccttgcg gcataaatga aaaggggatg ctggtgatcg    6960
aagggccgct gccgccgggc tgtattcaga ctatttgggg cgacgatgcg cgttttgtga    7020
agacttactg gtcgctgttt aaccgtcagg tttatgccac tttcgactgg ggaatccgcg    7080
acgccgaggg gtattacttt attctgggcc gtaccgatga tgtgattaat attgcgggtc    7140
atcggctggg gacgcgagaa atagaagaaa gtatctccag ctacccgaac gtagcggaag    7200
tggcggtagt ggggataaaa gacgctctga aagggcaggt agcggtggcg tttgtcattc    7260
cgaagcagag cgatacgctg gcggatcgcg aggcggcgcg cgacgaggaa acgcgcgatta    7320 tggcgctggt ggacaaccag atcggtcact ttggtcgtcc ggcgcatgtc tggtttgttt    7380
cgcagctccc caaaacgcgt tccggaaaga tgcttcgccg cacgatccag gcgatctgcg    7440
aaggccgcga tccgggcgat ctgacaacca ttgacgatcc cgcgtcgttg cagcaaattc    7500
gccaggcgat cgaagaatag ccgtaagccg gataagccgc gttcggcaac gggttagact    7560
cagcgactga atagtggggt gtaaagtcgg gaaagggcgg cagcgcgccg ccctgtaaca    7620
gaattaa                                                              7627
```

<210> SEQ ID NO 7
<211> LENGTH: 57
<212> TYPE: DNA
<213> ORGANISM: Artificial Sequence
<220> FEATURE:
<223> OTHER INFORMATION: multiple cloning site

```
<400> SEQUENCE: 7
gctagcgaat tcgagctcgg tacccgggga tcctctagag tcgacctgca ggcatgc      57

<210> SEQ ID NO 8
<211> LENGTH: 61
<212> TYPE: DNA
<213> ORGANISM: Artificial Sequence
<220> FEATURE:
<223> OTHER INFORMATION: multiple cloning site

<400> SEQUENCE: 8
gctagcagga ggaattcacc atggtacccg gggatcctct agagtcgacc tgcaggcatg   60
c                                                                   61

<210> SEQ ID NO 9
<211> LENGTH: 65
<212> TYPE: DNA
<213> ORGANISM: Artificial Sequence
<220> FEATURE:
<223> OTHER INFORMATION: promoter

<400> SEQUENCE: 9
tggcacaccc cttgctttgt ctttatcaac gcaaataaca agttgataac aaaggatggg   60
ctatg                                                               65

<210> SEQ ID NO 10
<211> LENGTH: 75
<212> TYPE: DNA
<213> ORGANISM: Artificial Sequence
<220> FEATURE:
<223> OTHER INFORMATION: promoter

<400> SEQUENCE: 10
tggcacaccc cttgctttgt ctttatcaac gcaaataaca agttgataac aagctagcag   60
gaggaattca ccatg                                                    75
```

INDUCIBLE EXPRESSION VECTORS AND METHODS OF USE THEREOF

CROSS-REFERENCE

This application claims the benefit of U.S. Provisional Patent Application No. 60/695,940, filed Jul. 1, 2005, which application is incorporated herein by reference in its entirety.

STATEMENT REGARDING FEDERALLY SPONSORED RESEARCH

This invention was made with Government support under grant no. GM070763 awarded by the National Institutes of Health. The Government has certain rights in this invention.

FIELD OF THE INVENTION

The present invention is in the field of expression vectors for production of RNAs and proteins in host cells, and in particular in the field of inducible expression vectors.

BACKGROUND OF THE INVENTION

There is a general need for readily regulatable promoters to control the amount and the timing of gene expression in a variety of experimental and commercial applications. In particular, homogeneous expression of a recombinant gene in all cells of the population is an important factor for successful protein production to perform metabolic optimization rather than massive overexpression. However, the available repertoire of *Escherichia coli* expression systems (lactose-inducible $P_{lac}$ and arabinose-inducible $P_{BAD}$) are subject to all-or-none gene expression, in which intermediate inducer concentrations produce an inhomogeneous culture with a subpopulation of cells that is fully induced and a subpopulation that is uninduced (Novick 1957, Siegele 1997).

Recently, homogenous expression from $P_{BAD}$ was achieved (Khlebnikov 2000) by placing arabinose transporter gene under control of a promoter that was not regulated by arabinose. However, this system uses the inexpensive sugar (L-arabinose) as an inducer and is somewhat weaker than the $P_{lac}$ promoter (Baneyx 1999). In a similar vein, the all-or-none induction of lactose-inducible promoters can be eliminated through the use of a gratuitous inducer, IPTG, that readily diffuses across the cell wall (Khlebnikov 2002) and a lacY deletion mutant because the uptake of IPTG is largely mediated by the proton symport lac permease (Jensen 1993). Despite many merits and wide usage, the lactose-inducible promoter systems, together with T7-based expression system that is based on lactose promoters, require the expensive inducer IPTG as an inducer. For large-scale or repeat experiments such methods may become rather unattractive options (Su 1990). Also, IPTG could easily contaminate the protein products due to its indigestibility by the cells (Figge 1988). Moreover, the use of IPTG for production of human therapeutic proteins is undesirable because of its toxicity (Figge 1988).

T7-based expression systems (Studier 1990) are widely used for large scale over-expression of recombinant proteins in both bacterial (Tabor 1985, Studier 1986) and eukaryotic cells (Fuerst 1986, Dunn 1988). The system comprises T7 gene 1 encoding T7 RNA polymerase, which specifically interacts with the T7 promoter (Tabor 1985). In particular, T7 RNA polymerase exhibits superior processability as compared to *E. coli* housekeeping RNA polymerase (Studier 1986). Despite great successes in using the T7 expression system for protein production, it has considerable problems. To be used in *E. coli*, a bacterial strain was engineered to carry a chromosomal copy of T7 gene 1 under the control of lacUV5 promoter, and an expression vector containing the T7 promoter was constructed. The most commonly encountered problems of the T7 system are inconsistency in levels of expression, formation of inclusion bodies (Hoang 1999, Jeong 1999) and instability of clones (Hattman 1985). Inconsistency in levels of expression of target genes has been attributed to the leaky expression of T7 RNA polymerase, although the gene is placed under control of strong inducible promoters. Gene products that severely affect the host cell's growth rate at low concentrations are considered to be toxic and can make it difficult to stably maintain plasmids (Hattman 1985).

More recently, the thermoregulatable T7 expression system was reported for a simple and inexpensive way to operate (Chao 2002, Wang 2004). Also, cold-shock expression vectors were developed to substitute the widely used pET vectors (Qing 2004). However, these two systems have a disadvantage in that the gene fused to the T7 promoter on the plasmid can only be actively expressed at higher or lower temperature rather than optimal growth temperature.

There is a need in the art for expression vectors that avoid the above-mentioned drawbacks. The present invention addresses this need.

SUMMARY OF THE INVENTION

The present invention provides nucleic acids that include a promoter that is inducible by a transcriptional activator protein; and a nucleotide sequence that encodes the transcriptional activator protein. The present invention provides expression vectors that provide for inducible production of gene products in a host cell. The present invention further provides host cells genetically modified with a subject expression vector. The present invention further provides methods for producing a gene product in a host cell.

BRIEF DESCRIPTION OF THE DRAWINGS

FIG. 1A depicts a map of pPro18 as a representative of the pPro vectors. FIG. 1B provides the nucleotide sequences of multiple cloning site-1 (MCS1; SEQ ID NO:7); multiple cloning site-2 (MCS2; SEQ ID NO:8). FIG. 1C depicts prpBCDE promoter ($P_{prpB}$) sequences ("prp operon" (SEQ ID NO:9); and pPro24 (SEQ ID NO: 10)).

FIGS. 4A and 4B depict a comparison of $P_{prpB}$-gfp expression in BL21(DE3) (FIG. 4A) and JSB (FIG. 4B).

FIGS. 10A-C and FIGS. 10D-F depict the nucleotide sequence of a coding sequence for prpR, a prpBCDE promoter, and prpBCDE coding sequences from *E. coli* (SEQ ID NO:5) and from *S. typhimurium* (SEQ ID NO:6), respectively.

FIG. 11 depicts an amino acid sequence [SEQ ID NO:3] of a transcriptional activator protein.

FIGS. 12A-D depict induced and un-induced expression in the *Salmonella*-based $P_{prpB}$-gfp and $P_{T7}$-gfp in *E. coli* BL21 (DE3).

FIGS. 16A-C depict histograms showing the number of *E. coli* BL21 cells harboring pPro7(S)-gfp with a given fluorescence (A,B); and culture-averaged fluorescence (C) when grown in M9 glucose (A) or glycerol (B) (5 g/L) minimal medium containing different concentrations of propionate.

DEFINITIONS

Figure 2A:
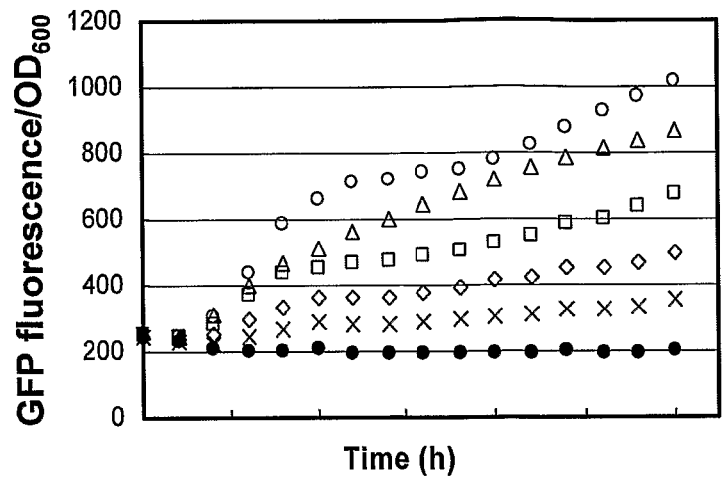
FIGS. 2A-C depict a comparison of culture-average fluorescence (fluorescence per $OD_{600}$ unit) of *E. coli* harboring the pBAD24-gfp (FIG. 2A), pPro24(E)-gfp (FIG. 2B), or pTrc99A-gfp (FIG. 2C).

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "peptide," "polypeptide," and "protein" are used interchangeably herein, and refer to a polymeric form of amino acids of any length, which can include coded and non-coded amino acids, chemically of biochemically modified or derivatized amino acids, and polypeptides having modified peptide backbones.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell); however, in the context of a heterologous nucleic acid, the same nucleotide sequence as found endogenously is produced in an unnatural (e.g., greater than expected or greater than naturally found) amount in the cell, or a nucleic acid comprising a nucleotide sequence that differs in sequence from the endogenous nucleotide sequence but encodes the same protein (having the same or substantially the same amino acid sequence) as found endogenously is produced in an unnatural (e.g., greater than expected or greater than naturally found) amount in the cell; (c) the nucleic acid comprises two or more nucleotide sequences that are not found in the same relationship to each other in nature, e.g., the nucleic acid is recombinant.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate, production of a desired product by various mechanisms (see "DNA regulatory sequences", below).

Thus, e.g., the term "recombinant" polynucleotide or nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal, elements such as plasmids and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

A nucleic aid is hybridizable to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis, (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an expression vector" includes a plurality of such vectors and reference to "the host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides nucleic acids that include a promoter that is inducible by a transcriptional activator protein; and a nucleotide sequence that encodes the transcriptional activator protein. The present invention provides expression vectors that provide for inducible production of gene products in a host cell. The present invention further provides host cells genetically modified with a subject expression vector. The present invention further provides methods for producing a gene product in a host cell.

Nucleic Acids, Vectors, and Host Cells

The present invention provides an isolated nucleic acid comprising a $P_{prpB}$ promoter that is inducible by a prpR transcription activating protein; and a nucleotide sequence that encodes the prpR transcriptional activator protein.

Figure 9:
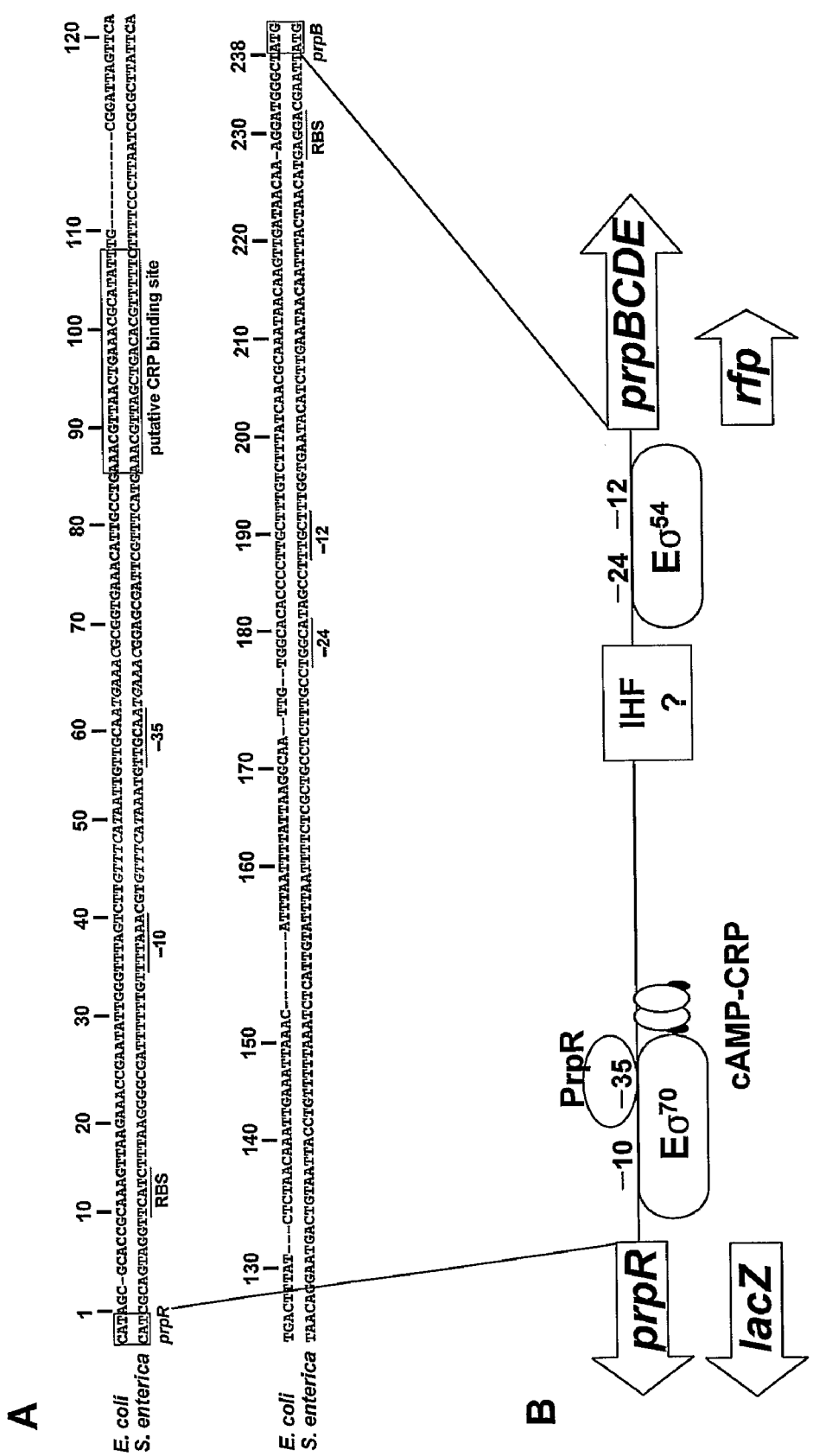
FIG. 9 depicts nucleotide sequences of a $P_{prpB}$ from *E. coli* (SEQ ID NO:1) and a $P_{prpB}$ from *Salmonella enterica* (SEQ ID NO:2).
Figure 10A:
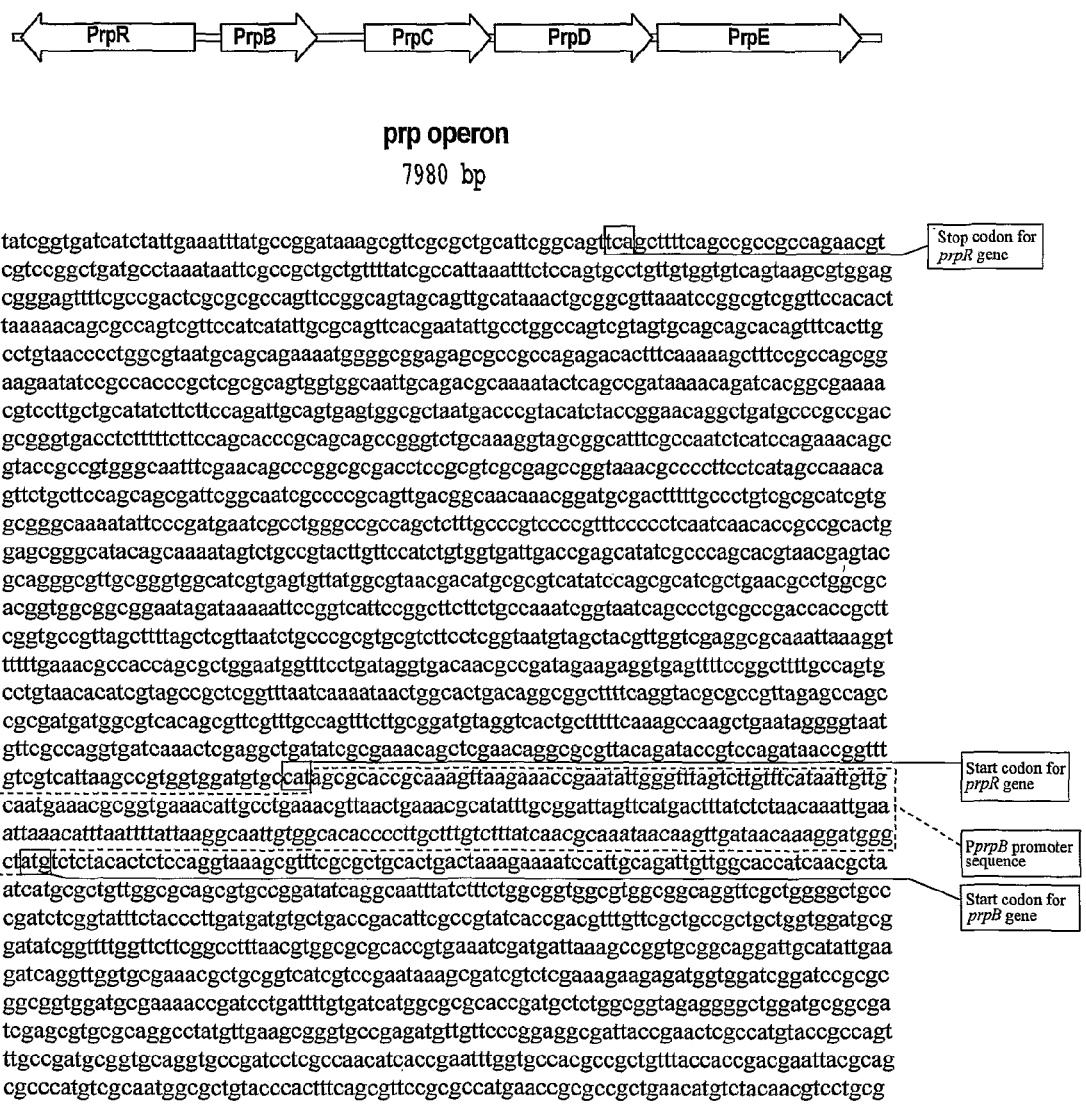

In some embodiments, the $P_{prpB}$ promoter comprises a nucleotide sequence that has at least about 50%, at least about 60%, at least about 70%, at least about 75%, at least about 80%, at least about 85%, at least about 90%, at least about 95%, at least about 98%, or at least about 99% nucleotide sequence identity with one of the nucleotide sequences depicted in FIG. 9 (i.e., one of SEQ ID NOs:1 and 2). In some embodiments, the P$_{prpB}$ promoter comprises a nucleotide sequence that hybridizes under stringent hybridization conditions with one of the nucleotide sequences depicted in FIG. 9 (i.e., one of SEQ ID NOs:1 and 2). In other embodiments, the P$_{prpB}$ promoter comprises a nucleotide sequence that has at least about 50%, at least about 60%, at least about 70%, at least about 75%, at least about 80%, at least about 85%, at least about 90%, at least about 95%, at least about 98%, or at least about 99% nucleotide sequence identity with a stretch of from about 20 to about 50, from about 50 to about 75, from about 75 to about 100, from about 100 to about 125, from about 125 to about 150, from about 150 to about 200, or from about 200 to about 225 contiguous nucleotides of one of the nucleotide sequences depicted in FIG. 9 (i.e., one of SEQ ID NOs:1 and 2).

In some embodiments, the nucleic acid comprises a nucleotide sequence that encodes a transcriptional activator protein having at least about 50%, at least about 60%, at least about 70%, at least about 75%, at least about 80%, at least about 90%, at least about 95%, at least about 98%, or at least about 99%, amino acid sequence identity to the amino acid sequence depicted in FIG. 11 (SEQ ID NO:3).

In some embodiments, the nucleotide sequence encoding the transcriptional activator protein has at least about 50%, at least about 60%, at least about 70%, at least about 75%, at least about 80%, at least about 85%, at least about 90%, at least about 95%, at least about 98%, or at least about 99% nucleotide sequence identity with a nucleotide sequence encoding prpC, as set forth in FIGS. 10A-C or FIGS. 10D-F (e.g., SEQ ID NO:5 or SEQ ID NO:6).

In many embodiments, the nucleotide sequence encoding the transcriptional activator protein is operably linked to a promoter, e.g., a prpC promoter comprising a nucleotide sequence having at least about 50%, at least about 60%, at least about 70%, at least about 75%, at least about 80%, at least about 85%, at least about 90%, at least about 95%, at least about 98%, or at least about 99% nucleotide sequence identity with a prpC promoter as depicted in FIGS. 10A-C or FIGS. 10D-F (e.g., SEQ ID NO:5 or SEQ ID NO:6).

In some embodiments, the nucleic acid comprises a multiple cloning site (MCS) positioned adjacent to the promoter, e.g., positioned 3' of the promoter. Suitable MCS are well known in the art and include recognition sequences for two or more restriction endonucleases, e.g., EcoRI, HindIII, NcoI, SalI, PstI, XbaI, and the like. Exemplary MCS are depicted in FIG. 1B (SEQ ID NOs:7 and 8). The MCS allows insertion of a nucleic acid comprising a nucleotide sequence encoding a gene product of interest into the nucleic acid. When inserted into an expression vector, a subject nucleic acid comprising a nucleotide sequence encoding a gene product of interest provides for propionate-inducible expression of the gene product in a host cell, e.g., a prokaryotic host cell.

The present invention further provides expression vectors comprising a P$_{prpB}$ promoter that is inducible by a prpR transcription activating protein; and a nucleotide sequence that encodes the prpR transcriptional activator protein, as described above. In many embodiments, the expression vector further comprises a MCS positioned adjacent to the promoter, e.g., positioned 3' of the promoter, as described above. The MCS allows insertion of a nucleic acid comprising a nucleotide sequence encoding a gene product of interest into a subject expression vector. A subject expression vector provides for propionate-inducible expression of a selected gene product in a host cell.

The expression vector can be based on any of a variety of known vectors. For example, a subject expression vector can use any known plasmid vector, e.g., a pBR322-based plasmid, as a "backbone."

In some embodiments, a subject expression vector further comprises a nucleotide sequence encoding a gene product of interest, where the nucleotide sequence encoding the gene product of interest is operably linked to the prpB promoter. Gene products include RNA and polypeptides. Polypeptide gene products of interest include detectable proteins (e.g., fluorescent proteins, luminescent proteins, chromogenic proteins); proteins having enzymatic activity; receptor proteins; transcription factors; cytokines; antibodies and antibody fragments; and the like. RNA gene products of interest include short interfering RNA; mRNA; and the like. In some embodiments, the gene product is heterologous to the host cell. In other embodiments, the gene product is not heterologous to the host cell.

The present invention further provides compositions comprising a subject nucleic acid. The present invention further provides compositions comprising a subject recombinant vector. Compositions comprising a subject nucleic acid or a subject expression vector will in many embodiments include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a nuclease inhibitor; and the like. In some embodiments, a subject nucleic acid or a subject recombinant vector is lyophilized.

The present invention further provides host cells, e.g., in vitro host cells and in vivo host cells, comprising a subject nucleic acid or a subject expression vector.

Host cells are in many embodiments unicellular organisms, or are grown in culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveroinyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a eukaryotic cell other than a plant cell.

In other embodiments, the host cell is a prokaryotic cell. Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270: 299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

In many embodiments, the host cell comprises a prpBCDE gene, e.g., a nucleic acid comprising nucleotide sequences encoding prpBCDE gene products, e.g., as set forth in FIGS. 10A-C or FIGS. 10D-F (e.g., SEQ ID NO:5 or SEQ ID NO:6).

Methods of Producing a Gene Product

The present invention provides a method for producing a gene product (e.g., an RNA, or a polypeptide) in a host cell. The method generally involves culturing a host cell genetically modified with an expression vector that comprises: a) a promoter that is inducible by a transcriptional activator protein, where the promoter comprises a nucleotide sequence having at least about 75% nucleotide sequence identity to any of the nucleotide sequences depicted in FIG. 9 (i.e., one of SEQ ID NOs:1 and 2); b) a nucleotide sequence encoding a gene product of interest operably linked to the transcription activator protein-inducible promoter; and c) a nucleotide sequence that encodes the transcriptional activator protein, where the transcriptional activator protein comprises an amino acid sequence having at least about 75% amino acid sequence identity to the amino acid sequence depicted in FIG. 11 (SEQ ID NO:3). Culturing of the host cell is carried out in medium comprising propionate. Culturing of the host cell in medium comprising propionate provides for induction of the transcriptional activator protein-inducible promoter and production of the gene product of interest. In some embodiments, the method further comprises isolating and purifying the gene product.

Induction of the promoter results in at least a 2-fold increase in the amount of the gene product produced in the host cell, compared with the amount of the gene product produced in the host cell in the absence of propionate. For example, induction results in at least a 2-fold, at least a 2.5-fold, at least a 5-fold, at least a 10-fold, at least a 20-fold, at least a 50-fold, at least a 100-fold, or greater, increase in the in the amount of the gene product produced in the host cell, compared with the amount of the gene product produced in the host cell in the absence of propionate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Propionate-Inducible Expression Vectors

Materials and Methods

Bacterial strains and media. The bacterial strains used in this study are listed in Table 1.

TABLE 1

*E. coli* strains and plasmids used in this study.

| Strains or plasmids | Description | Reference or source |
|---|---|---|
| Strains | | |
| DH10B | F$^-$mcrA Δ(mrr-hsdRMS mcrBC) φ80dlacZΔM15 Δ lacX74 deoR recA1 araΔ139 Δ(ara leu)7697 galU galKλ$^-$rpsL endA1 nupG Str$^r$ | Life Technologies |
| BL21 | F$^-$ ompT[lon] hsdS$_B$(r$_B$ m$_B$) gal dcm | Novagen |
| BL21(DE3) | F$^-$ ompT[lon] hsdS$_B$(r$_B$ m$_B$) gal dcm λDE3 | Novagen |
| JSB | BL21(DE3)/Δ(sbm-ygfDGHI) | This work |
| *S. enterica* TR6583 | metE205 ara-9 | Reference |
| Plasmids | | |
| P70GL | pBAD24 carrying gfpuv and lacZ, Ap$^r$ | 37 |
| pTrc99A-gfp | pTrc99A carrying gfpuv, Ap$^r$ | This work |
| pTrc99A | trc promoter, lacI$^q$, pBR322 ori, Ap$^r$ | Amersham Pharmacia Biotech |
| pPro18 | 2-MC inducible, pBR322 ori, Ap$^r$ | This work |
| pPro18-Cm | 2-MC inducible, pBR322 ori, Cm$^r$ | This work |
| pPro18-Kan | 2-MC inducible, pBR322 ori, Km$^r$ | This work |
| pPro24 | 2-MC inducible, pBR322 ori, Ap$^r$ | This work |
| pPro30 | 2-MC inducible, p15A ori, Ap$^r$ | This work |
| pPro33 | 2-MC inducible, p15A ori, Cm$^r$ | This work |
| pPro24-gfp | pPro24 carrying gfpuv, Ap$^r$ | This work |
| pPro33-gfp | pPro33 carrying gfpuv, Cm$^r$ | This work |
| pBAD18 | arabinose inducible, pBR322 ori, Ap$^r$ | 12 |
| pBAD24 | arabinose inducible, pBR322 ori, Ap$^r$ | 12 |
| pBAD18-Cm | arabinose inducible, pBR322 ori, Cm$^r$ | 12 |
| pBAD18-Kan | arabinose inducible, pBR322 ori, Km$^r$ | 12 |
| pBAD30 | arabinose inducible, p15A ori, Ap$^r$ | 12 |

TABLE 1-continued

E. coli strains and plasmids used in this study.

| Strains or plasmids | Description | Reference or source |
|---|---|---|
| pBAD33 | arabinose inducible, p15A ori, Cm$^r$ | 12 |
| pBAD24-gfp | pBAD24 carrying gfpuv, Ap$^r$ | This work |
| pET16b-gfp | pET16b carrying gfpuv, pBR322 ori, Ap$^r$ | |
| pET31b-gfp | pET31b carrying gfpuv, pBR322 ori, Ap$^r$ | |
| pPro18(S) | pPro18 containing Salmonella P$_{prpB}$ and prpR | |
| pPro24(S) | pPro24 containing Salmonella p$_{prpB}$ and prpR | |
| pPro24(S)-gfp | pPro24(S) carrying gfpuv, pBR322 ori, Apr | |
| pPro7(S)-gfp | pPro24(S)-gfp with AAGAAGG RBS | |

Ap$^r$, ampicillin resistance; Cm$^r$, chloramphenicol resistance; Km$^r$, kanamycin resistance; ori, replication origin.

All DNA manipulations were performed in *E. coli* DH10B using established protocols (31). Strain JSB, a sbm-ygfD-ygfG-ygfH-ygfI deletion mutant of *E. coli* BL21 (DE3), was constructed by a PCR-mediated gene disruption method (9). Cultures were grown in Luria-Bertani (LB) broth at 37° C. Cell growth was monitored as the optical density at a wavelength of 600 nm (OD$_{600}$). Media were amended with arabinose, IPTG, or sodium propionate (pH 8.0) as indicated. The following antibiotics were used at the concentrations indicated: ampicillin, 100 µg/ml; chloramphenicol, 30 µg/ml; kanamycin, 50 µg/ml.

Construction of pPro vectors. Constructed vectors differ in multicloning sites, antibiotic resistance gene, and copy number. The DNA containing P$_{prpB}$ and prpR was amplified from *E. coli* BL21 (DE3) or *S. enterica* genomic DNA. To construct pPro vectors, araC and P$_{BAD}$ on the pBAD series of expression vectors were replaced with prpR and P$_{prpB}$ (FIG. 1).

(i) pPro18 (E). The PCR product containing prpR and P$_{prpB}$ of *E. coli* BL21 (DE3) was digested with ClaI and NheI and ligated to the large fragments of pBAD18 resulting from digestion with the same enzymes, creating pPro18 (FIG. 1A).

(ii) pPro18-Cm. The ClaI-NheI prpR-P$_{prpB}$ region from pPro18 (E) was ligated to the large fragments of pBAD18-Cm resulting from digestion with the same enzymes, creating pPro18-Cm.

(iii) pPro18-Kan. The Bst1107I-NheI prpR-P$_{prpB}$ region from pPro18 was ligated to the large fragments of pBAD18-Kan resulting from digestion with the same enzymes, creating pPro18-Kan.

(iv) pPro24 (E). The ClaI-NheI prpR-P$_{prpB}$ region from pPro18 was ligated to the large fragments of pBAD24 resulting from digestion with the same enzymes, creating pPro24 (FIG. 1C).

(v) pPro30. After deletion of the NheI site in the front of pACYC origin region of pBAD30 by partial digestion with NheI, T4 DNA polymerase treatment, and self-ligation, the ClaI-NheI prpR-P$_{prpB}$ region from pPro 18 was ligated to the large fragments of pBAD30 resulting from digestion with the same enzymes, creating pPro30.

(vi) pPro33. After deletion of the NheI site in the front of pACYC origin region of pBAD33 by partial digestion with NheI, T4 DNA polymerase treatment, and self-ligation, the ClaI-NheI prpR-P$_{prpB}$ region from pPro 18 was ligated to the large fragments of pBAD33 resulting from digestion with the same enzymes, creating pPro33.

(vii) pPro18(S). The PCR product containing prpR and P$_{prpB}$ of *S. enterica* was digested with ClaI and NheI and ligated to the large fragments of pBAD18 resulting from digestion with the same enzymes, creating pPro18(S).

(viii) pPro24(S). The ClaI-NheI prpR-P$_{prpB}$ region from pPro18(S) was ligated to the large fragments of pBAD24 resulting from digestion with the same enzymes, creating pPro24(S).

Plasmid construction. The reporter plasmids were made to test the utility of the pPro vectors for the regulated expression of genes. The promoter-reporter plasmids pBAD24-gfp, pPro24-gfp, and pTrc99A-gfp were constructed by subcloning the PCR-amplified gfpuv gene encoding the UV-excitable green fluorescent protein (GFP) from p70GL into the MCS of pBAD24, pPro24, and pTrc99A, respectively. GFP was used to provide an indirect, quantitative measurement of the transcriptional properties of the cloned gene (10, 40). Plasmids pPro7(E)-gfp and pPro7(S)-gfp were constructed by PCR-amplifying gfp using a 5' primer containing the strong ribosome binding site (RBS) sequence AAGAAGG that originated from the pET vector and by ligating the PCR products into the NheI/SalI-digested pPro24(E) and pPro24(S), respectively.

Transcriptional fusion studies of P$_{BAD}$, P$_{prpB}$, or P$_{trc}$ promoters linked to the gfp reporter gene. A seed culture was made by inoculating cells into LB medium containing ampicillin (100 µg/ml) and growing the cells overnight at 37° C. Fifty µl each of the seed cultures were inoculated into 5 ml of fresh LB medium supplemented with ampicillin (100 µg/ml). The cells were grown at 37° C. and when the OD$_{600}$ reached 0.5, the cells harboring pBAD24-gfp, pPro24(E)-gfp, and pTrc99A-gfp were induced with arabinose, propionate, or IPTG, respectively.

GFP fluorescence in batch cultures of *E. coli* containing the reporter plasmids expressing gfp was measured in a Tecan SpectraFluor Plus plate reader (Tecan-US, Durham, N.C.) using an excitation wavelength of 405 nm and an emission wavelength of 535 µm. GFP fluorescence was normalized for cell density (GFP fluorescence per OD$_{600}$ unit). The GFP content of individual cells was determined as described previously (21) using a Beckman-Coulter EPICS XL flow cytometer (Beckman Instruments) equipped with an argon laser (emission at 488 nm/15 mV) and a 525 nm band pass filter.

Results

Characteristics and construction of vectors. A prpBCDE promoter expression system (prpR-P$_{prpB}$) has been developed that can be induced using 2-methyl citrate (2-MC). The system is composed of the prpBCDE promoter, P$_{prpB}$, and a transcriptional activator gene, prpR, that activates the expression of cloned genes under the control of P$_{prpB}$ in the presence of 2-MC. The 2-MC is made from propionate via propionyl-CoA using the chromosomally-encoded prpCE gene products (14, 29, 30). Thus, the promoter was inactive in *E. coli* DH10B, which lacks the prp operon (23). In addition to 2-MC and PrpR, expression of the prpBCDE operon of enteric bacteria—which codes for 2-methylcitrate (2-MC) synthase, 2-methylcitrate dehydratase, 2-methylcitrate lyase (three key enzymes in the methylcitrate cycle), and propionyl-CoA synthetase—is dependent on the cAMP-CRP complex, IHF, NtrA, and sigma-54-dependent RNA polymerase (5, 16, 23, 29, 30, 39). Although seemingly complex, these regulatory arrangements allow bacteria to produce enzymes for propionate catabolism only when they are needed, suggesting that $P_{prpB}$ must be inducible.

The pPro vectors contain prpR and $P_{prpB}$ followed by an MCS and rrnB transcription terminators derived from the arabinose-inducible pBAD expression vectors (FIG. 1A). They also carry a pBR322 origin of replication (pPro 18/18-Cm/18-Kan/24) or a p15A origin replication (pPro30/33), an M13 intragenic region for phage packaging and production of single stranded DNA, and an antibiotic resistance gene (FIG. 1A). Only pPro24, which carries MCS2, contains an optimized Shine-Dalgarno site (SD) (34) and a translational start codon (ATG) at the NcoI site in order to easily clone genes that lack sequences for initiation of translation (FIGS. 1B and C). The pPro30/33 vectors, which harbor the p15A origin of replication from pACYC184, can be used to reduce gene expression (due to lower copy number), and are compatible with pBR322-derived plasmids (pPro18/18-Cm/18-Kan/24) to stably co-express different genes on separate plasmids in a single host. Since the pBAD30/33 vectors have two NheI sites, the NheI site located in front of the p15A origin of pPro30/33 was removed by partial digestion, T4 polymerase treatment, and self-ligation so that the NheI site in MCS1 would be available for cloning purposes.

Figure 2B:
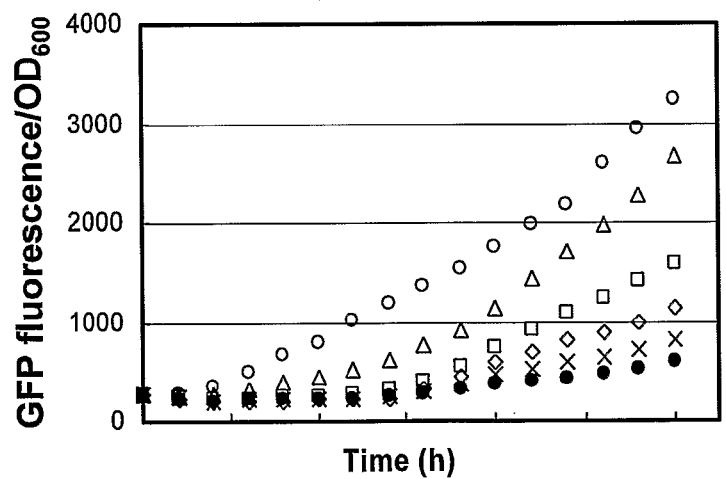
Figure 2C:
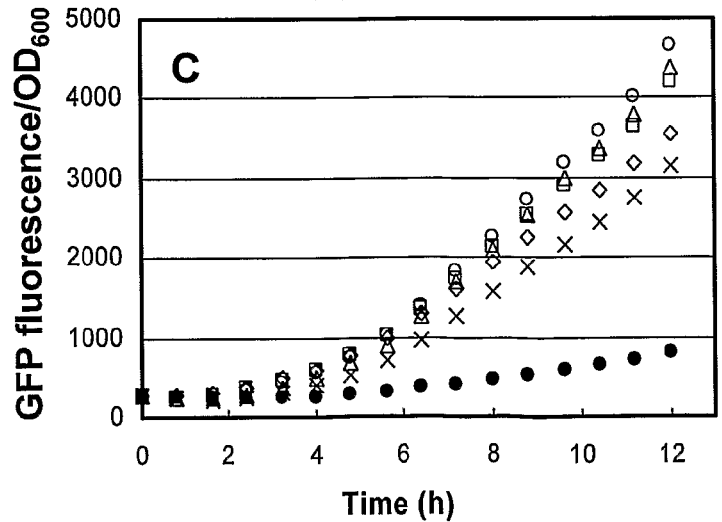

Regulated expression of the $P_{prpB}$-gfp gene. A useful property of a controllable expression system is that the expression level of a recombinant product is proportional to the amount of inducer added to the cell culture. To determine the range of inducibility, the gene encoding GFP (gfp) was placed under the control of $P_{prpB}$ and used as a reporter for promoter activity. We compared the expression levels of $P_{prpB}$-gfp to those of $P_{BAD}$-gfp and $P_{trc}$-gfp in E. coli BL21(DE3)(FIG. 2). The prpR-$P_{prpB}$ system was regulated over a wide range of inducer concentrations, and production of GFP varied directly and linearly with the extracellular propionate concentration (FIG. 2B). In a similar manner, the expression of gfp under the control of $P_{BAD}$ was regulatable with arabinose concentration in the medium (FIG. 2A). However, as described above, it has been reported that the variation in expression level with inducer concentration is due a variation in the percentage of induced cells in the population rather than a variation in the expression level in individual cells (22 and discussed below). Although it does not suffer from all-or-none gene expression, the $P_{trc}$ system did not show high dose-dependent inducibility with the addition of IPTG (FIG. 2C). The reason for this highly cooperative induction is that IPTG induces its own carrier (24). It has been reported that this problem is alleviated by deletion of the lac permease (19).

In terms of the dynamic response to inducer addition, the $P_{BAD}$ system has been reported to have a very fast rate of induction (12). In contrast, the $P_{trc}$ system exhibited a time delay before expression of GFP. Like the $P_{BAD}$ system the prpR-$P_{prpB}$ expression system showed significant GFP fluorescence after about 90 min of induction upon addition of 50 mM propionate.

In the absence of inducer, $P_{BAD}$ showed much lower basal expression throughout the induction period than $P_{prpB}$ and $P_{trc}$, with $P_{prpB}$ having slightly less background expression than $P_{trc}$. However, the expression levels between $P_{trc}$ and $P_{BAD}$ or $P_{prpB}$ cannot be compared directly because they have different sequences at the ribosome-binding site (RBS). Compared to the $P_{BAD}$-based vectors having the same RBS sequences, $P_{prpB}$ had much higher levels of induced expression. The amount of background expression of all three promoters seems to be correlated with the maximal expression level.

Modulation of $P_{prpB}$-gfp expression in individual cells. The ability to obtain different levels of expression by partial induction of the promoter is an important feature of a controllable expression system. Flow cytometry was used to examine modulation of $P_{prpB}$-gfp by measuring the extent of induction from $P_{prpB}$ in single cells at different concentrations of propionate. The results indicate that all cultures were uniformly induced across the population at all propionate concentrations tested, and the level of gene expression in individual cells varied with the propionate concentration (FIG. 3). These results, taken together with the above data, suggest that the variation in population-average expression from $P_{prpB}$ as a function of propionate concentration resulted from partial induction of the $P_{prpB}$ promoter rather than an all-or-none response.

Figure 3A:
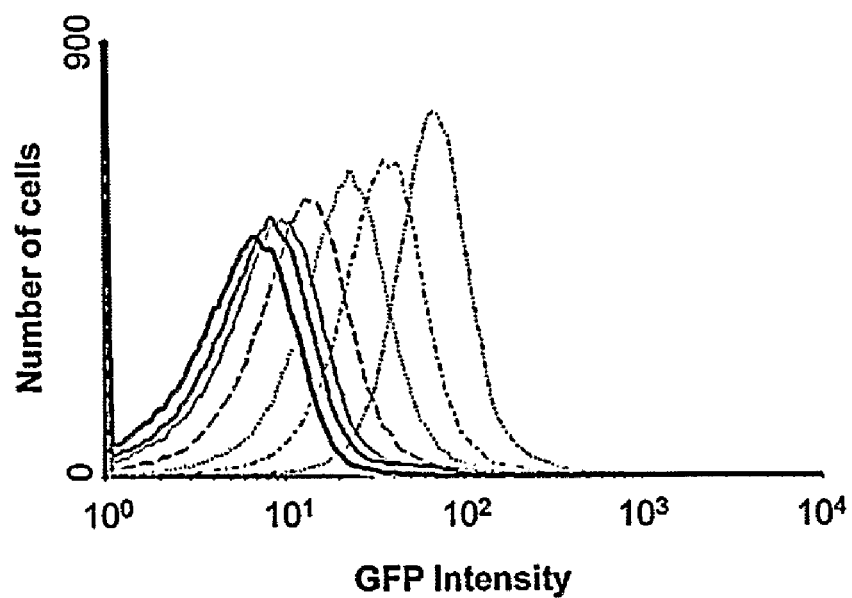
FIGS. 3A and 3B depict histograms showing the number of cells with a given fluorescence in *E. coli* BL21 (DE3) cultures harboring pPro24(E)-gfp induced with the different concentrations of propionate.
Figure 3B:
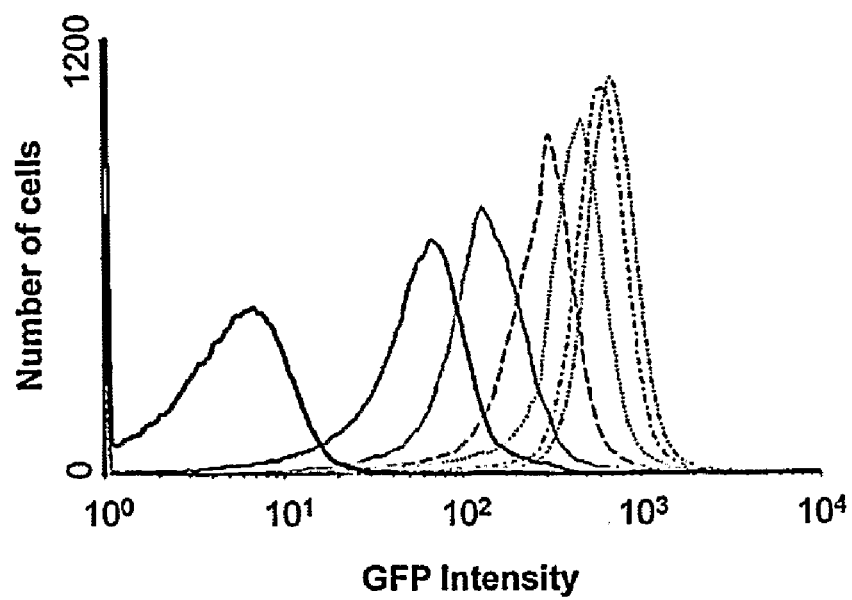

Basal expression of prpR-$P_{prpB}$. In general, a tightly regulated system is desirable because many recombinant products can be toxic to the expression host. This propionate-inducible expression system was found to be slightly "leaky"; background expression of gfp was detected in the absence of exogenous inducer (FIGS. 2B and 3B). The basal expression levels depended on the carbon source (acetate, citrate, lactate, galactose, glutamate, and succinate) in minimal medium (data not shown) suggesting that propionate, propionyl-CoA, or 2-MC can be produced from endogenous metabolic pathways. One such pathway, encoded by the E. coli operon sbm-ygfD-ygfG-ygfH, converts succinate/succinyl-CoA to propionate/propionyl-CoA (13). To test the possibility that this pathway produced propionate/propionyl-CoA and increased background expression in the absence of exogenous inducer, a sbm-ygfD-ygfG-ygfH-ygfI deletion was introduced into E. coli BL21(DE3) creating strain JSB. Basal expression of $P_{prpB}$-gfp in JSB was significantly lower than that obtained using BL21 (DE3); however, the induced expression level decreased as well (FIG. 4). Based on this finding, it is not clear whether propionate/propionyl-CoA produced from succinate/succinyl-CoA by the sbm-ygfD-ygfG-ygfH-ygfI gene products contributed to the background. Like $P_{BAD}$ (12), $P_{prpB}$ showed higher background and higher induced expression in minimal medium than in rich medium (data not shown), possibly due to the presence of effector molecules that could induce catabolite repression or that could inhibit expression in some other ways (12).

Basal expression from plasmid pPro33-gfp was generally lower than that from plasmid pPro24(E)-gfp (FIG. 4). This lower basal expression should be a reflection of the decreased plasmid copy number. In E. coli JSB carrying pPro33-gfp, basal expression was similar to background levels observed in JSB harboring the pBAD24 empty vector. $P_{prpB}$ exhibited low basal expression level in the absence of inducer and similar expression level in the presence of inducer, compared with trc system (FIGS. 2B and C). Since the prpR and prpBCDE promoters are subject to catabolite repression (23), glucose can be used to reduce the background expression to negligible level (FIG. 4).

Example 2

The DNA regions that contain the $P_{prpB}$ promoter and the prpR gene were amplified from E. coli BL21 (DE3) and S. enterica genomic DNA. The araC gene and $P_{BAD}$ promoter of the pBAD24 and pBAD18 vectors were replaced with the PCR-amplified prpR gene and the $P_{prpB}$ promoter of E. coli (E) or *S. enterica* (S) strains, creating pPro24(E)/pPro24(S) and pPro18(E)/pPro18(S), respectively. The pPro18 vector is represented in FIG. 1A-C.

Reporter Plasmid Construction

The promoter-reporter gene plasmids were made to test the utility of the pPro vectors for the regulated expression of genes. The constructs, pBAD24-gfp, pET31b-gfp, pPro24 (E)-gfp, pPro24(S)-g, and pTrc99A-gfp were constructed by subcloning the PCR-amplified gfpuv gene encoding the UV-excitable green fluorescent protein (GFP) from the p70GL plasmid into the MCS of the vector pBAD24, pET31b, pPro24(E), pPro24(S), and pTrc99A, respectively. Plasmid pPro7(S)-gfp was constructed by subcloning the PCR-amplified gfpuv plus the AAGAAG RBS into the MCS of the pPro18(S) vector. The expression of the target gene was tested by using GFP, as expression of this protein can be monitored using a Spectrafluor Fluorimeter as well as by flow-cytometry.

Construction of JSB Strain

The sbm-ygfD-ygfG-ygfH-ygfI gene cluster was deleted from *E. coli* BL21 (DE3) by a PCR-mediated gene disruption method (Datsenko 2000) thereby creating *E. coli* JSB.

Regulated Expression of the $P_{prpB}$-gfp Gene.

A useful property of a controllable expression system is that the expression level of a recombinant product is proportional to the amount of inducing agent added into the cell culture by partial induction of the promoter. The GFP reporter gene was expressed as a recombinant product under the transcriptional control of $P_{prpB}$.

Overnight grown cells carrying pPro24(E)-gfp and pPro24 (S)-gfp in LB at 37° C. were subcultured (1:100) into fresh LB medium (5 ml) with ampicillin (100 μg/ml), grown at 37° C. in a shaking incubator until the $OD_{600}$ reached 0.5, and then exposed to different concentrations of propionate in 96-well plates at 37° C. with shaking in a microplate reader. Time-course expression of GFP (GFP fluorescence per $OD_{600}$ unit) after addition of propionate was determined using a Tecan SpectraFluor Plus plate reader. Both plasmids have the AGGAG RBS from the pBAD24 vector.

Figure 6A:
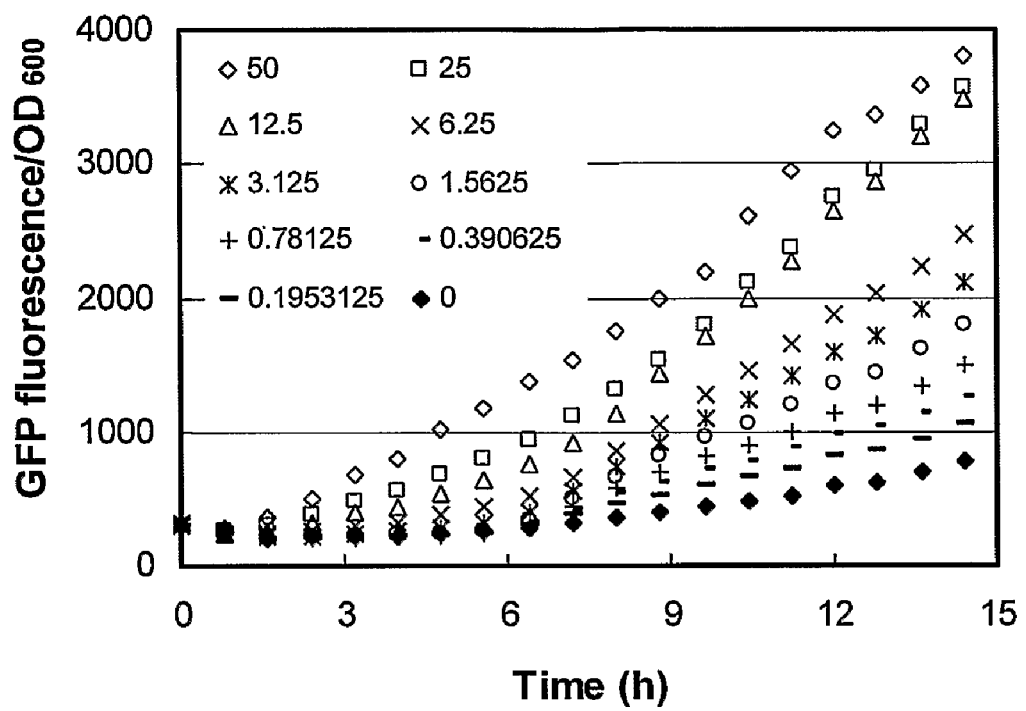
FIGS. 6A and 6B depict culture-average fluorescence (fluorescence per $OD_{600}$ unit) of *E. coli* BL21 (DE3) harboring the pPro24(E)-gfp carrying *E. coli* $P_{prpB}$ and prpR (A) and the pPro24(S)-gfp carrying *S. enterica* $P_{prpB}$ and prpR (B) after induction in broth cultures.
Figure 6B:
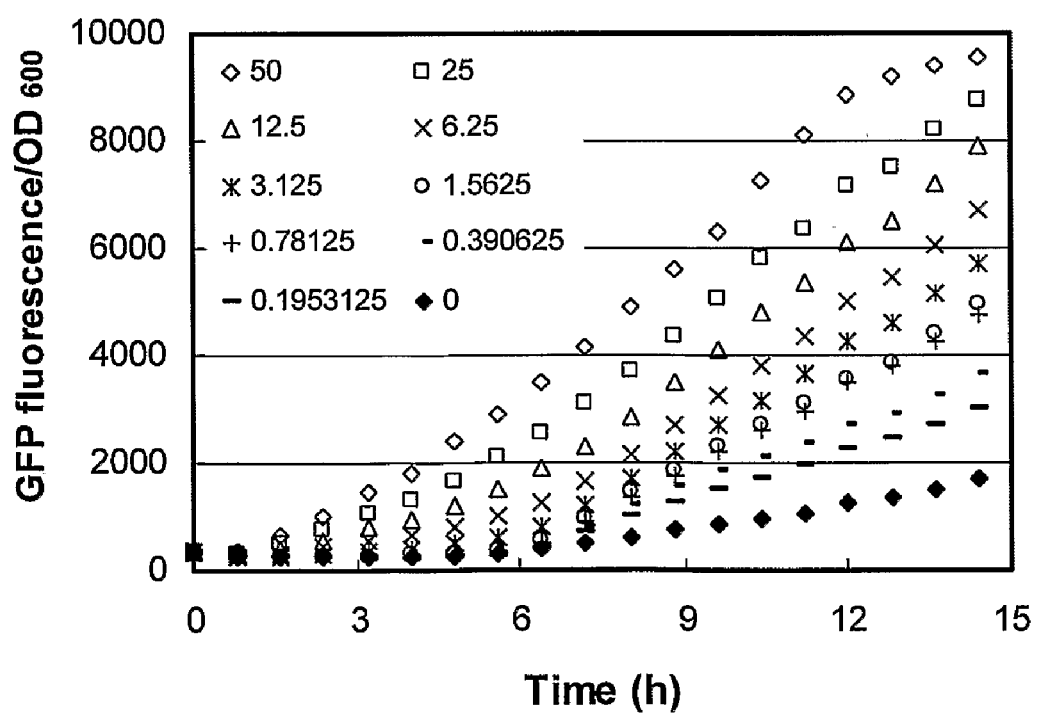

FIGS. 6A and 6B show a plot of amount of GFP produced by cultures of strain BL21 (DE3) as a function of induction at different levels of propionate. The induction experiments showed that $P_{prpB}$ was modulated over a wide range of inducer concentrations in bacterial cell cultures, in which GFP is expressed differently in response to different levels of propionate. Interestingly, higher expression levels were obtained in BL21(DE3) carrying pPro24(S)-gfp than BL21 (DE3) carrying pPro24(E)-gfp (FIGS. 6A and 6B).

Analysis of $P_{prpB}$-gfp Expression in Individual Cells.

To demonstrate that the population-average variation resulted from partial induction of the $P_{prpB}$ promoter (FIGS. 6A and 6B), flow cytometry experiments were conducted to examine the susceptibility to modulation of $P_{prpB}$-gfp by measuring the extent of induction from $P_{prpB}$ promoter at different concentrations of inducer.

Overnight grown cells in LB at 37° C. were subcultured (1:100) in fresh LB medium (5 ml) with ampicillin (100 μg/ml), grown at 37° C. in a shaking incubator, and then induced with different concentrations of propionate when $OD_{600}$ reached 0.5. *E. coli* BL21 (DE3) harboring pBAD24 was used as a control. Two (FIG. 3A) and six (FIG. 3B) hours after addition of propionate, the GFP content of individual cells was determined by flow cytometry analysis of expressed GFP as described previously (Khlebnikov 2001) using a Beckman-Coulter EPICS XL flow cytometer (Beckman Instruments) equipped with an argon laser (emission at 488 nm/15 mV) and a 525 nm band pass filter.

All cultures containing pPro24(E)-gfp showed homogenous levels of $P_{prpB}$-gfp activity among cell populations grown in the presence of different levels of propionate after 2 and 6 hrs. These results demonstrate that individual cells were uniformly induced across the population at all inducer concentrations and that the level of gene expression in individual cells varied with propionate concentration (FIGS. 3A and 3B).

Maximal and Basal Expression of prpR-$P_{prpB}$ System

Figure 7A:
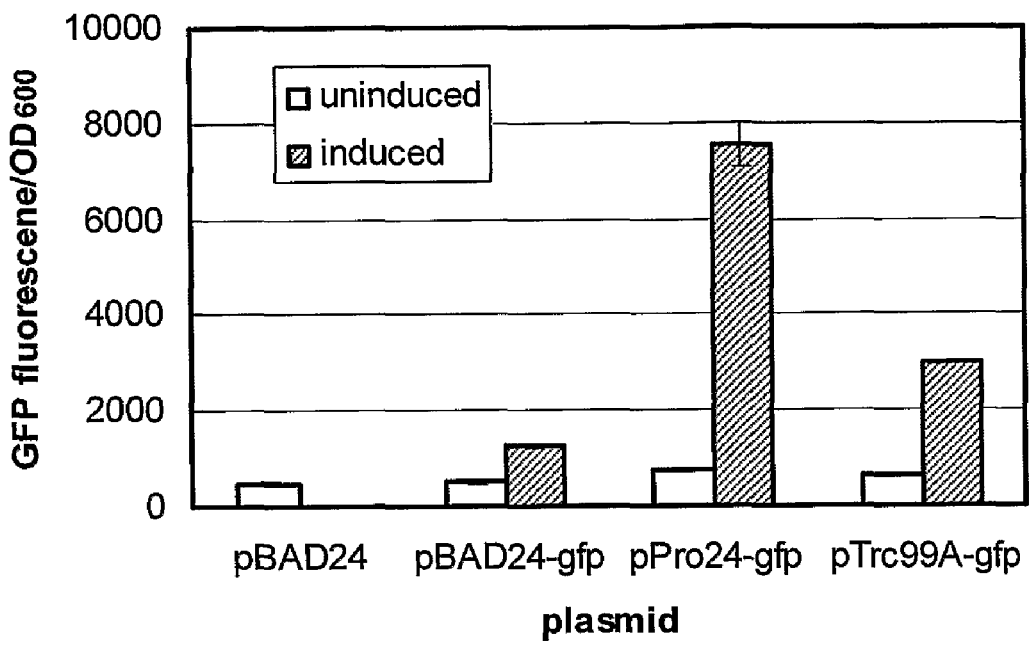
FIGS. 7A and 7B depict levels of maximal and basal expression of the $P_{BAD}$-gfp, $P_{prpB}$-gfp, and $P_{trc}$-gfp in *E. coli* BL21(DE3).
Figure 7B:
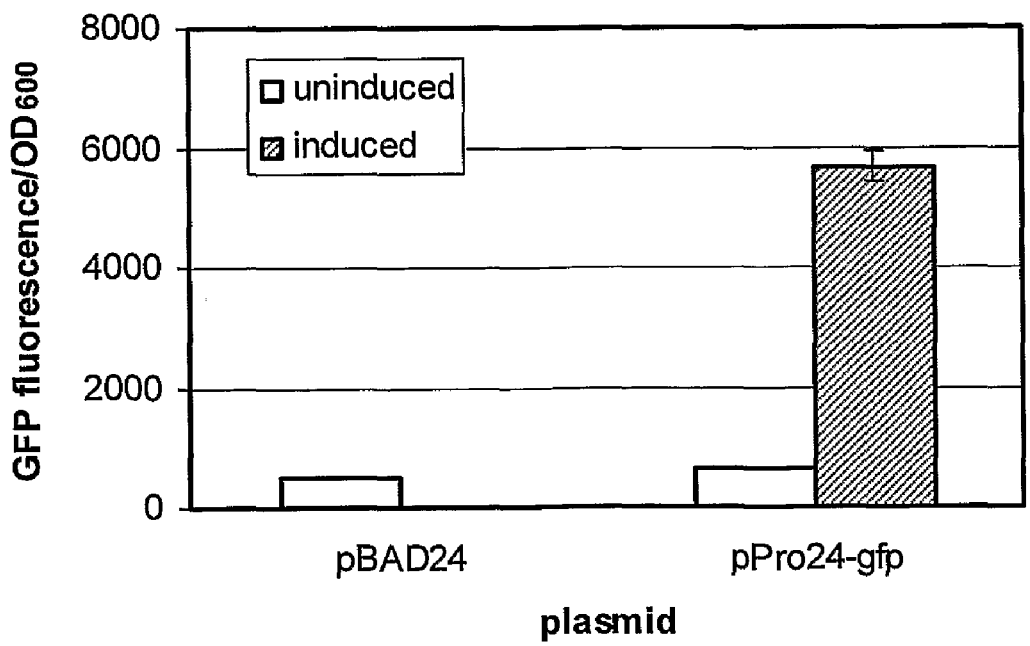

In general, a tightly regulated system is most desirable because many recombinant products can be toxic to the expression host. However, this expression system was found to be "leaky"; background expression of the inserted GFP gene was detected even in the noninduced state (FIGS. 7A and 7B). The sbm-ygfD-ygfG-ygfH-ygfI gene cluster was deleted from *E. coli* BL21(DE3) by a PCR-mediated gene disruption method (Datsenko 2000) creating *E. coli* JSB. The reporter plasmid was transformed into the sbm-ygfD-ygfG-ygfH-ygfI deletion strain (JSB) in order to analyze the effect of mutation on the operon on the basal and maximal expression of prpR-$P_{prpB}$ system. Also, maximal and basal expression of $P_{BAD}$, $P_{trc}$, and $P_{prpB}$ were compared with BL21(DE3) carrying pPro24(E)-gfp.

To test this prediction, cells containing different plasmids were grown overnight in LB at 37° C. and then subcultured (1:100) into fresh LB medium (5 ml) with ampicillin (100 μg/ml) and inducer (arabinose, 15 mM; IPTG, 1 mM; propionate, 50 mM) and grown at 37° C. with shaking. After 20 h of induction, the level of GFP expression was determined with or without induction with exception for pBAD24 without inducer.

As expected, the basal expression of $P_{prpB}$-gfp was 50% lower in JSB [pPro24(E)-gfp] compared to BL21(DE3) [pPro24(E)-gfp]. However, the induced expression level decreased as well (FIGS. 7A and 7B). This finding indicates that propionyl-CoA produced from succinate by the sbm-ygfD-ygfG-ygfH-ygfI gene products contributed partially to the observed background activity. Also, like $P_{BAD}$ or $P_{lac}$, glucose could be used to lower further the levels of repression.

As a result, the background expression of this system was reduced by maintaining expression constructs in a sbm-ygfD-ygfG-ygfH-ygfI deletion strain (FIG. 7B). $P_{prpB}$ exhibited a higher level of inducible GFP expression compared to $P_{BAD}$ and $P_{trc}$ system by 6-fold and 2-fold, respectively. Comparison of culture-average fluorescence (fluorescence per $OD_{600}$ unit) of *E. coli* BL21(DE3) harboring pPro18(S)-gfp (A) or pET31b-gfp (B) after induction in broth culture.

Overnight grown cells in LB at 37° C. were subcultured (1:100) into fresh LB medium (5 ml) with ampicillin (100 μg/ml), grown at 37° C. in a shaking incubator, and then induced with various concentrations of propionate when the $OD_{600}$ reached 0.5. Expression levels of GFP after addition of propionate were determined using a Tecan SpectraFluor plus plate reader after (1:5) dilution with LB broth. Both plasmids have the AAGAAG RBS originating from pET31b vector.

Figure 8:
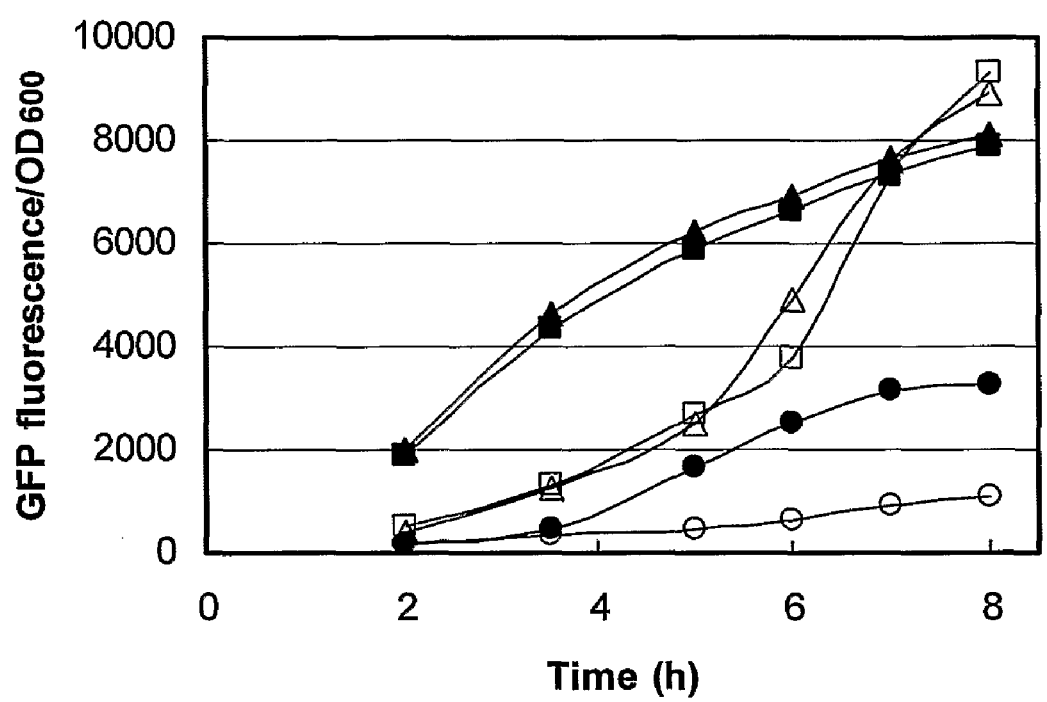
FIG. 8 depicts comparison of culture-average fluorescence (fluorescence per $OD_{600}$ unit) of *E. coli* BL21(DE3) harboring the pPro7(S)-gfp (A) or pET31b-gfp (B) after induction in broth culture.

As a result, over-expression and lower basal expression of cloned genes in *E. coli* BL21(DE3) strain was achieved in a *Salmonella* prpR-$P_{prpB}$ expression system containing the $P_{prpB}$ promoter and the prpR gene of *S. enterica* instead of those from *E. coli*. Compared to the T7 expression system, this system showed higher expression levels after 7 h of induction (FIG. 8).

FIG. 1. Map of pPro18 as a representative of the pPro vectors. All pPro vectors have MCS1 (A) with the exception of pPro24, which has MCS2 (B). All restriction endonuclease sites are unique except for PstI in pPro18, pPro18-Cm, and pPro30; EcoRI in pPro18-Cm and pPro33; and SmaI and XmaI in pPro18-Kan. The −12/−24 regions of the prpBCDE promoter and integrated NheI site are indicated. The ATG start sites for PrpB in prpBCDE or for cloned genes on pPro24 are boxed (C). Abbreviations: rrnBT1, 2, part of the strong ribosomal rrnB terminators; ori, origin of replication; MCS, multicloning site; SD, Shine-Dalgarno box.

FIG. 2. Comparison of culture-average fluorescence (fluorescence per $OD_{600}$ unit) of *E. coli* harboring the pBAD24-gfp (A), pPro24(E)-gfp (B), or pTrc99A-gfp (C). Overnight grown cells carrying the plasmid in LB at 37° C. were subcultured (1:100) into fresh LB medium (5 ml) with ampicillin (100 µg/ml), grown at 37° C. in a shaking incubator until the $OD_{600}$ reached about 0.5, and then exposed to different concentrations of inducer in 96-well plates at 37° C. with shaking in a Tecan SpectraFluor Plus plate reader. The background fluorescence intensity was not removed by using background subtraction. Symbols indicate inducer concentrations. (A) Open circles, 20 mM arabinose; open triangles, 5 mM; open rectangles, 1.25 mM; open diamonds, 0.31 mM; crosses, 0.08 mM; solid circles, 0 mM. (B) Open circles, 50 mM propionate; open triangles, 12.6 mM; open rectangles, 3.2 mM; open diamonds, 0.8 mM; crosses, 0.2 mM; solid circles, 0 mM. (C) Open circles, 1 mM IPTG; open triangles, 0.25 mM; open rectangles, 0.063 mM; open diamonds, 0.016 mM; crosses, 0.004 mM; solid circles, 0 mM.

FIG. 3. Histograms showing the number of cells with a given fluorescence in *E. coli* BL21(DE3) cultures harboring pPro24(E)-gfp induced with the different concentrations of propionate. Cells grown overnight in LB medium at 37° C. were subcultured (1:100) into fresh LB medium (5 ml) with ampicillin (100 µg/ml), grown at 37° C. in a shaking incubator until the $OD_{600}$ reached about 0.5, and then exposed to different concentrations of propionate. *E. coli* harboring pBAD24 was used as a control. The fluorescence in single cells was determined two (A) and six (B) hours after addition of propionate. Different lines indicate different propionate concentrations added to the medium: ▬▬,control; ▬▬,0 mM; ▬▬▬,0.2 mM; ▬ ▬,0.8 mM; ‒ ‒ ‒ ‒ ‒, 3.2 mM; ▬ · ·▬,12.6 mM; ▬ · ·▬,50 mM.

FIG. 4. Comparison of $P_{prpB}$-gfp expression in BL21(DE3) (A) and JSB (B). Cells harboring various plasmids were grown overnight in LB medium at 37° C. and subcultured (1:100) in fresh LB medium (5 ml) containing ampicillin (100 µg/ml) and without or with propionate (Prop) and glucose (Glc). The cells were grown at 37° C. with shaking. After 15 h of cultivation, the GFP expression level was determined. BL21(DE3) or JSB strain harboring pBAD24 empty vector was used as a control. The background fluorescence intensity was not removed by using background subtraction. Error bars show the standard deviation of experiments performed in triplicate.

Figure 5:
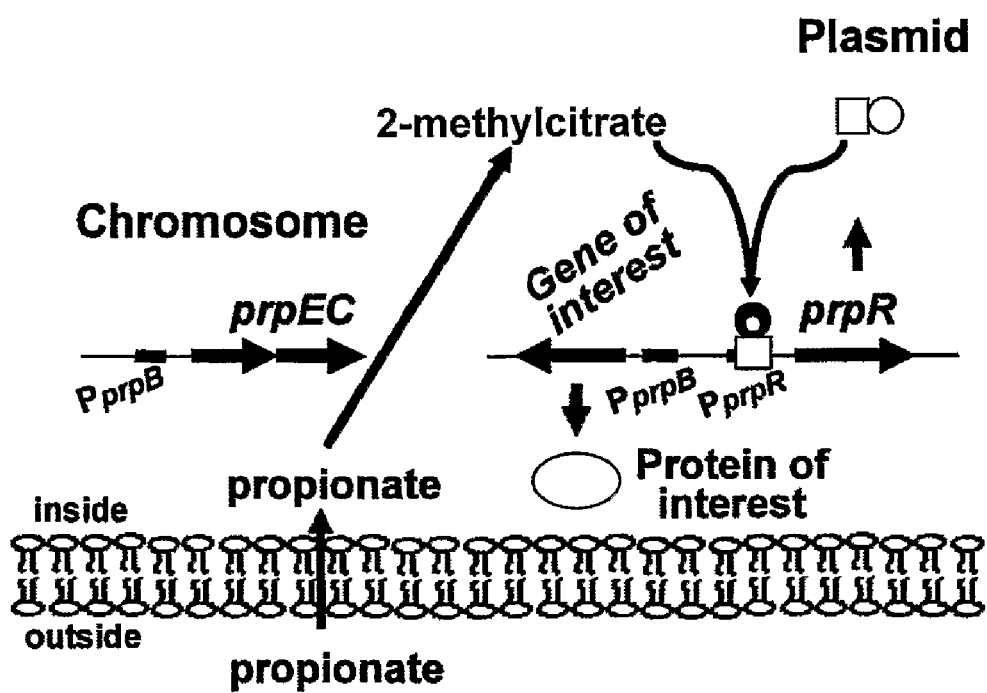
FIG. 5 depicts is a schematic representation of a subject prpR-$P_{prpB}$ gene expression system.

FIG. 5. A diagram showing prpR-$P_{prpB}$ gene expression system. This system is composed of the $P_{prpB}$ promoter and a transcriptional activator gene, prpR, whose protein product activates the expression of cloned genes in the presence of 2-MC. In addition, prpCE gene products are required for the production of 2-MC from propionate through propionyl-CoA.

FIGS. 6A and 6B. Culture-average fluorescence (fluorescence per $OD_{600}$ unit) of *E. coli* BL21(DE3) harboring the pPro24-gfp carrying *E. coli* $P_{prpB}$ and prpR (A) and *S. enterica* $P_{prpB}$ and prpR (B) after induction in broth cultures. Propionate was added into the culture media up to a final concentration of 50 mM.

FIGS. 7A and 7B. Levels of maximal and basal expression of the $P_{BAD}$-gfp, $P_{prpB}$-gfp, and $P_{trc}$-gfp in *E. coli* BL21 (DE3).

FIG. 8 depicts comparison of culture-average fluorescence (fluorescence per $OD_{600}$ unit) of *E. coli* BL21(DE3) harboring the pPro18(S)-gfp (A) or pET31b-gfp (B) after induction in broth culture.

Example 3

Propionate-Regulated High-Yield Protein Production in *Escherichia coli*

Materials and Methods

Bacterial strains and media. The bacterial strains used in this study are listed in Table II. Cultures were grown in Luria-Bertani (LB) medium at 37° C. Cell growth was monitored as the optical density at a wavelength of 600 nm ($OD_{600}$). Media were supplemented with ampicillin (100 µg/ml). Arabinose, IPTG, or sodium propionate (pH 8.0) was used as an inducer.

TABLE II

| Strains or plasmids | Description |
|---|---|
| Strains | |
| *E. coli* | |
| DH10B | F− mcrA Δ(mrr-hsdRMS mcrBC) φ80dlacZΔM15 Δ lacX74 deoR recA1 araΔ139 Δ(ara leu)7697 galU galK λ− rpsL endA1 nupG Str$^r$ |
| BL21 | F− ompT hsdS ($r_B^- m_B^-$) gal dcm |
| BL21(DE3) | F− ompT hsdS($r_B^- m_B^-$) gal dcm λDE3 |
| MG1655 | F− λ− rph-1 |
| W3110 | F− λ− IN(rrnD-rrnE)1 rph-1 |
| *S. enterica* | |
| TR6583 | metE205 ara-9 |
| Plasmids | |
| p70GL | pBAD24 carrying gfpuv and lacZ, pBR322 ori, Ap$^r$ |
| pBAD24-gfp | pBAD24 carrying gfpuv, pBR322 ori, Ap$^r$ |
| pET16b-gfp | pET16b carrying gfpuv, pBR322 ori, Ap$^r$ |
| pET31b-gfp | pET31b carrying gfpuv, pBR322 ori, Ap$^r$ |
| pTrc99A-gfp | pTrc99A carrying gfpuv, pBR322 ori, Ap$^r$ |
| pPro24(E)-gfp | 2-MC inducible, pBR322 ori, Ap$^r$ |
| pPro24(S)-gfp | pPro24 carrying gfpuv, pBR322 ori, Ap$^r$ |
| pPro7-gfp | pPro24(S)-gfp derivative with AAGAAGG RBS |

Ap$^r$, ampicillin resistance; ori, replication origin.

Plasmid construction. All DNA manipulations were performed in *E. coli* DH10B using established protocols. To construct pPro24(S) the araC gene and $P_{BAD}$ promoter of pBAD24 were replaced with the PCR-amplified prpR and $P_{prpB}$ of *S. enterica*. The reporter plasmids, pET16b-gfp, pET31b-g, pPro24(S)-gfp, and pTrc99A-gfp, were constructed by subcloning the PCR-amplified gfpuv gene encoding the UV-excitable green fluorescent protein (GFP) from p70GL into the MCS of pET16b, pET31b, pPro24(S), and pTrc99A, respectively. Plasmid pPro7-gfp was constructed by PCR-amplifying gfp using a 5' primer containing the strong ribosome binding site (RBS) sequence AAGAAGG that originated from the pET vector and by ligating the PCR products into the NheI/SalI-digested pPro24(S).

Determination of in vivo promoter activities. Promoter activities were tested by using GFP for an indirect, quantitative measurement of the transcriptional properties of cloned g. Overnight grown cells in LB medium at 37° C. were subcultured (1:100) into fresh LB medium (5 ml in culture tube and 20 ml in shake flask) containing ampicillin (100 µg/ml), grown at 37° C. in a shaking incubator until the $OD_{600}$ reached about 0.6, and then induced at 37° C. in 96-well plates with shaking in a Tecan SpectraFluor Plus plate reader (Tecan-US, Durham, N.C.) or in a shaking incubator. GFP fluorescence was measured in the Tecan SpectraFluor Plus plate reader with an excitation wavelength of 405 nm and an emission wavelength of 535 nm and expressed as relative fluorescence units (RFU). The background fluorescence intensity was not removed by using background subtraction. For each culture, RFU is defined as the culture fluorescence relative to culture biomass at $OD_{600}$ and plotted against induction time.

Results

Characteristics and construction of vectors. A new prpR-$P_{prpB}$ expression system (*Salmonella* pPro) was constructed comprising an *E. coli* host having the prp operon and an expression vector harboring the prpBCDE promoter and the gene encoding the propionate activator protein (prpR) of *S. enterica*. Like the *E. coli* pPro system, this system can be induced by 2-methylcitrate (2-MC) produced from propionate through propionyl-CoA by the chromosomally-expressed prpCE products. The 2-MC-activated PrpR binds to an enhancer-like element located at a distance 5' of $P_{prpB}$, contacts the $\sigma^{54}$-dependent RNA polymerase by means of DNA loop formation, and activates transcription of the prpBCDE operon. According to DNA sequence analysis, the amino acid sequences of *E. coli* and *Salmonella* PrpR show high homology to each other (approximately 86% similarity) (BLAST search). On the other hand, the regions that include the prpR and prpBCDE promoters in *E. coli* and *S. enterica* (238 bp and 265 bp, respectively) have 148 identical base pairs.

Expression of the *Salmonella*-based prpR-$P_{prpB}$-gfp in *E. coli*. The green fluorescent protein (GFP) has been used to quantitatively analyze promoter strength and protein expression. The GFP gene was expressed under the transcriptional control of $P_{BAD}$, $P_{prpB}$, $P_{trc}$, or $P_{T7}$ in order to monitor leaky and induced expression in *E. coli* BL21(DE3). The expression levels of $P_{BAD}$-gfp, $P_{prpB}$-gfp, $P_{trc}$-gfp, and $P_{T7}$-gfp in the strain at different concentrations of inducers were measured and then compared (FIGS. 12A-D). Like *E. coli*-based pPro system, *Salmonella*-based prpR-$P_{prpB}$ system was regulated over a wide range of inducer concentrations, and GFP expression levels depend on the extracellular propionate concentration (FIG. 12A). On the other hand, the T7 system did not show dose-dependent inducibility with the addition of IPTG (FIG. 12B), probably because the uptake of the inducer IPTG is largely mediated by the proton symport lac permease, which is encoded by the lacY gene. Maximal levels of GFP expression were observed with the addition of 20 mM arabinose for pBAD24-gfp, 50 mM propionate for the two pPro plasmids [pPro24(E)-gfp and pPro24(S)-gfp], 62.5 µM IPTG for pTrc99A-gfp, and 1 mM IPTG for pET31b-gfp (FIG. 12C). Interestingly, the *Salmonella* pPro system containing $P_{prpB}$ and prpR of *S. enterica* showed about 3-fold higher GFP production than the *E. coli* pPro system. The BL21(DE3) strain containing pET31b-gfp exhibited approximately two- and four-fold higher GFP production than two BL21(DE3) strains containing pPro24(S)-gfp and pTrc99A-gfp, respectively. As expected, $P_{BAD}$ is very weak compared to $P_{prpB}$, $P_{T7}$, or $P_{trc}$. This result indicates that *Salmonella* $P_{prpB}$ is approximately two-fold stronger than $P_{trc}$, a promoter that is known to be quite strong. However, the expression levels among $P_{prpB}$, $P_{T7}$, and $P_{trc}$ could not be compared directly, because they have different sequences at the ribosome-binding site (RBS). Compared to the $P_{BAD}$-based vector having the same RBS sequences, $P_{prpB}$ showed much higher expression levels.

The *Salmonella* pPro expression system showed higher un-induced gfp expression than both *E. coli* pPro and $P_{trc}$ expression systems but much lower background expression than the T7 expression system (FIG. 12D and insert). Interestingly, the background and induced expression levels were similar to each other in the T7 system with the exception of a time delay in the background expression (FIG. 12B).

Figure 13A:
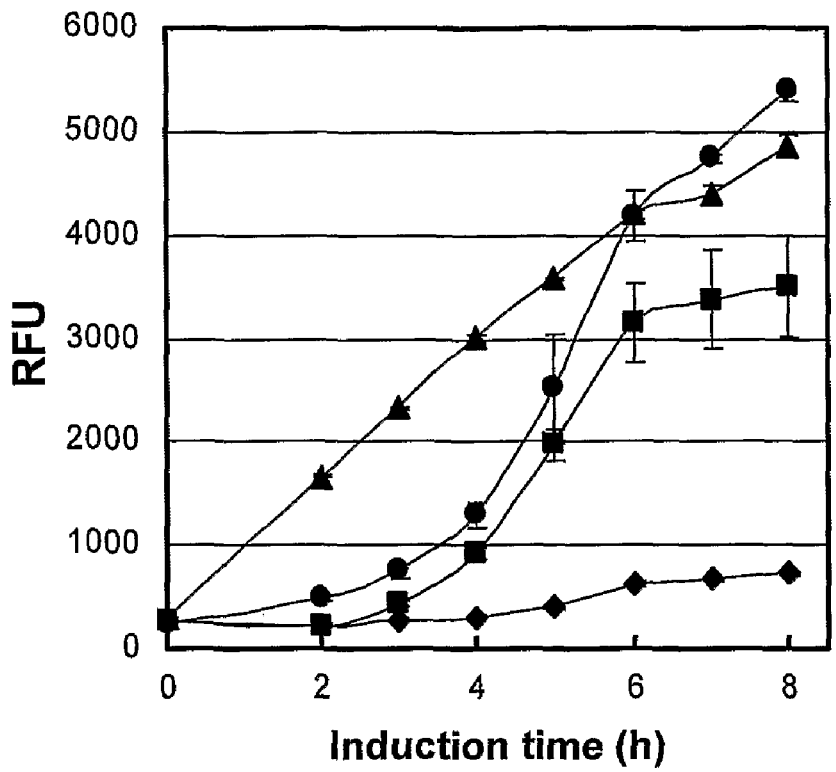
FIGS. 13A and 13B depict a comparison of maximal and un-induced expression levels between the pPro and T7 expression systems in culture tubes and shaking flasks.
Figure 13B:
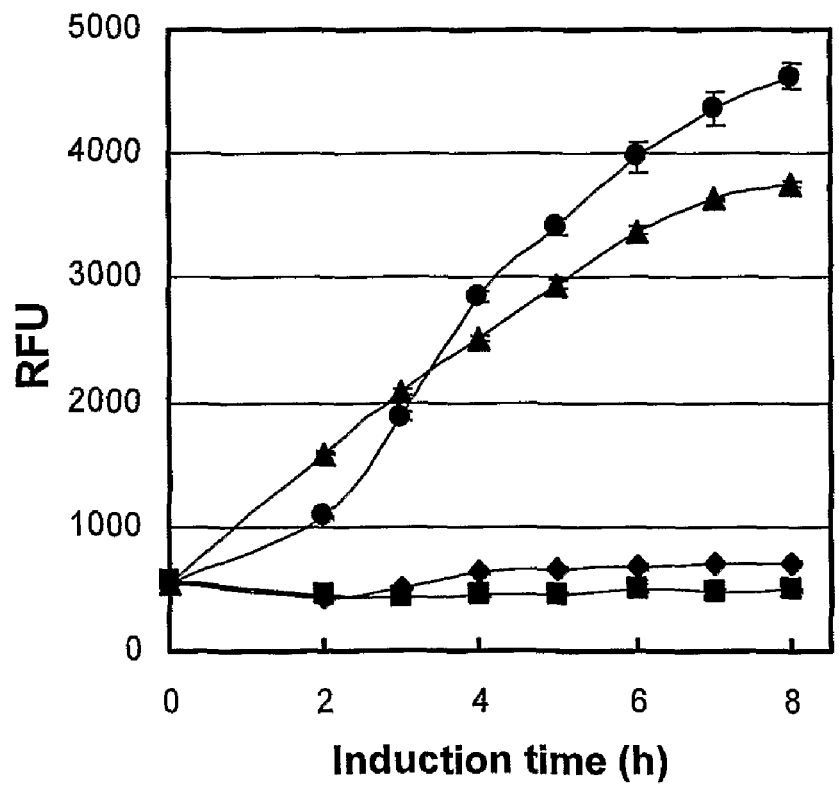

Comparison of GFP production from the *Salmonella*-based prpR-$P_{prpB}$ and the T7 expression systems. To compare the kinetics of GFP production from the *Salmonella* pPro and T7 expression systems under the same conditions, the AGGAG RBS of pPro24(S)-gfp was replaced with AAGAAG RBS originating from the pET vector, creating pPro7-gfp. The absolute levels of expression provided by the optimized pPro system were similar to those by the T7 system (FIG. 13A and FIG. 13B). The conversion of the RBS sequence AGGAG to AAGAAG resulted in an approximately two-fold increase in GFP expression in BL21(DE3) harboring the *Salmonella* pPro system (FIGS. 12C, 13A, 13B). The expression levels of *E. coli* BL21 harboring pPro7-gfp were slightly higher than those of BL21 (DE3) harboring pET16b-gfp after 6 h and 4 h of induction in culture tube and shake flask experiments, respectively (FIGS. 13A and B). In addition, the pPro system showed a high induction rate in the shake flask experiment, while the system had a time delay before high expression of gfp in culture tube experiment.

Like the *E. coli* pPro system (Lee and Keasling 2005a), the *Salmonella* pPro expression system showed almost no un-induced GFP production in the presence of glucose due to the catabolite-repressed prpR and prpBCDE promoters. The basal GFP production from the *Salmonella*-based pPro system in *E. coli* was consistent in different culture systems. In contrast, T7 system showed much different background expression levels in different culture conditions. In particular, T7 system showed no significant background expression in the shake flask experiment, while the background expression was similar to and half of the induced expression in TECAN and culture tube experiments, respectively (FIGS. 12B and 13A).

Expression from the *Salmonella* prpR-$P_{prpB}$ system in different *E. coli* strains. To obtain the highest expression, it is usually worthwhile to test different *E. coli* host strains. The *Salmonella* pPro system was analyzed in *E. coli* strains BL21 (FIG. 14A), MG1655 (FIG. 14B), and W3110 (FIG. 14C) by measuring GFP production at different concentrations of propionate. The *Salmonella* pPro system could be regulated over a wide range of propionate concentrations in these *E. coli* strains. Production of GFP depended on the propionate concentration added to culture medium. In general, the levels of GFP production were regulated by the extracellular propionate concentrations. However, there were some differences: strains BL21 and MG1655 had a slightly faster induction rate than strain W3110, and W3110 showed slightly less GFP production in the absence of propionate than did BL21 and MG1655. In addition, strain W3110 had lower maximal induced expression than strains BL21 and MG1655. Collectively the *Salmonella* prpR-$P_{prpB}$ system exhibited low basal expression and high induced expression in all *E. coli* strains tested. These results also suggest that the *Salmonella* pPro system is useful for the tightly-regulated, high-level production of foreign genes in a variety of *E. coli* strains.

FIGS. 12A-D Induced and un-induced expression in the Salmonella-based $P_{prpB}$-gfp (A) and $P_{T7}$-gfp (B) in E. coli BL21(DE3). Symbols indicate inducer concentrations. (A) Open circles, 50 mM propionate; open triangles, 12.6 mM; open rectangles, 3.2 mM; open diamonds, 0.8 mM; solid circles, 0 mM. (B) Open circles, 1 mM IPTG; open triangles, 0.25 mM; open rectangles, 0.063 mM; open diamonds, 0.016 mM; solid circles, 0 mM. Comparison of the maximal expression levels in the $P_{BAD}$-gfp, $P_{prpB}$-gfp, $P_{trc}$-gfp and $P_{T7}$-gfp in E. coli BL21(DE3) (C). Open circles, pET31b-gfp and 1 mM IPTG; open triangles, pPro24(S)-gfp and 50 mM propionate; open rectangles, pTrc99A-gfp and 62.5 μM IPTG; open diamonds, pPro24(E)-gfp and 50 mM propionate; crosses, pBAD24-gfp and 20 mM arabinose. Cells carrying the plasmid were exposed to different concentrations of inducer in 96-well plates at 37° C. with shaking in a Tecan SpectraFluor Plus plate reader. The data are representative from three independent experiments. RFU, relative fluorescence units.

FIGS. 13A-B. Comparison of maximal and un-induced expression levels between the pPro and T7 expression systems in culture tubes (A) and shaking flasks (B). E. coli BL21(DE3) harboring plasmid pET16b-gfp and E. coli BL21 harboring Ppro7-gfp were exposed to different concentrations of inducer in a shaking incubator. Expression levels of GFP were determined using a Tecan SpectraFluor Plus plate reader after (1:5) dilution into LB medium. Error bars show the standard deviation of experiments performed in triplicate. Symbols indicate plasmid and inducer concentrations. (A) Solid triangles, pET16b-gfp and 0.5 mM IPTG; solid circles, pPro7-gfp and 25 mM propionate; solid rectangles, pET16b- and 0 mM IPTG; solid diamonds, pPro7-gfp and 0 mM propionate. (B) Solid triangles, pET16b-gfp and 0.5 mM IPTG; solid circles, pPro7-gfp and 20 mM propionate; solid rectangles, pET16b-gfp and 0 mM IPTG; solid diamonds, pPro7-gfp and 0 mM propionate. RFU, relative fluorescence units.

Figure 14A:
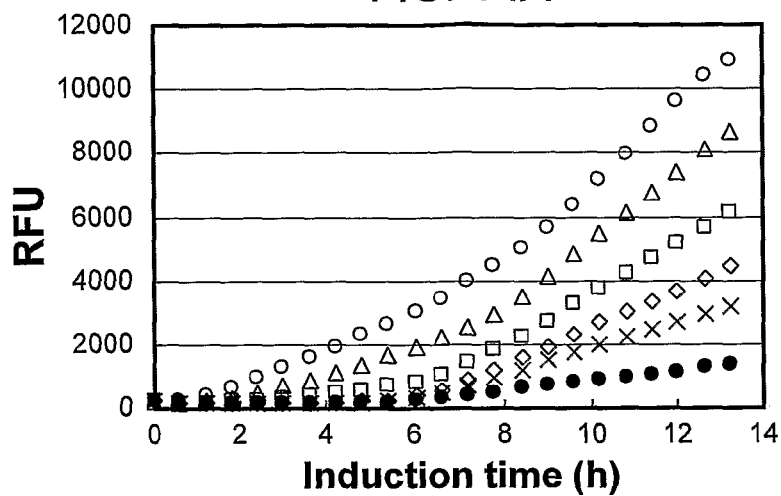
FIGS. 14A-C depict expression in various *E. coli* strains.
Figure 14B:
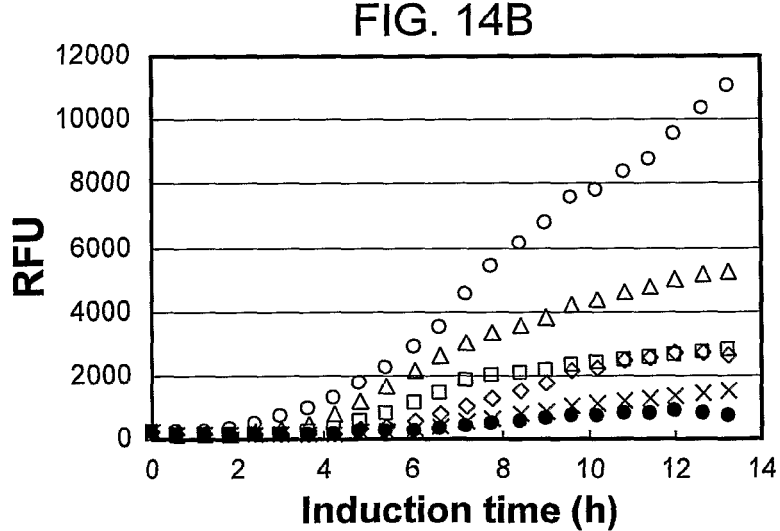
Figure 14C:
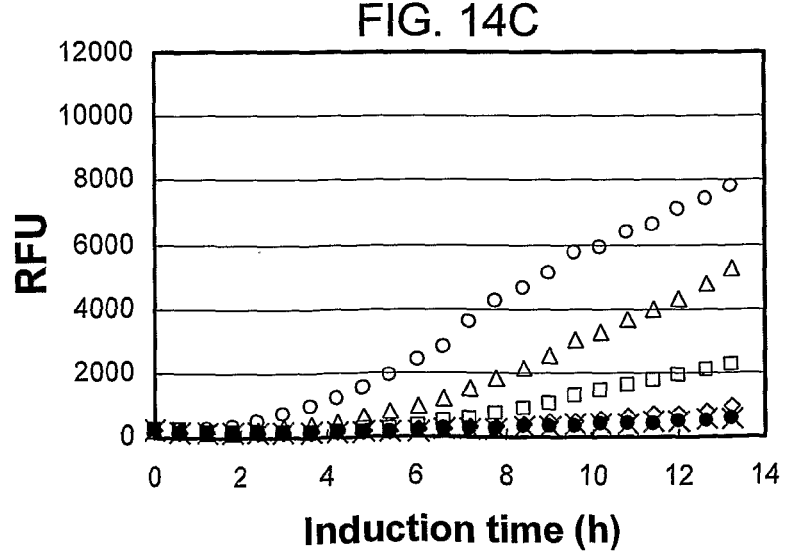

FIGS. 14A-C. The culture-averaged fluorescence in E. coli strains BL21 (A), MG1655 (B), and W3110 (C) strains harboring pPro7-gfp was compared after induction. This experiment was performed using the same culture method as described in FIG. 1. Symbols indicate inducer concentrations. Open circles, 50 mM propionate; open triangles, 12.6 mM; open rectangles, 3.2 mM; open diamonds, 0.8 mM; crosses, 0.2 mM; solid circles, 0 mM. The data are representative of the results observed in duplicate. RFU, relative fluorescence units.

Example 4

Effect of Glucose or Glycerol as the Sole Carbon Source on Gene Expression from the Salmonella prpBCDE Promoter in E. coli Materials and Methods Bacterial Strains and Media. The bacterial strains and plasmids used in this study are listed in Table 3. Cultures were grown in Luria-Bertani (LB) medium or M9 medium with glucose [wt/vol] or glycerol [vol/vol] at 37° C. Cell growth was monitored as the optical density at a wavelength of 600 nm ($OD_{600}$). Media were supplemented with ampicillin (100 μg/mL). Either isopropyl-β-D-thiogalactopyranoside (IPTG) or sodium propionate (pH 8.0) was used as the inducer.

TABLE 3

E. coli strains and plasmids used in this study.

| Strains or plasmids | Description |
|---|---|
| E. coli | |
| BL21 | F ompT hsdS($r_B$ $m_B$) gal dcm |
| BL21(DE3) | BL21/λDE3 |
| JSB | BL21(DE3)/Δ(sbm-ygfDGHI) |
| Plasmids | |
| pBAD24 | Arabinose inducible, pBR322 ori, $Ap^r$ |
| pET16b-gfp | pET16b carrying gfpuv, pBR322 ori, $Ap^r$ |
| pPro7($E^a$)-gfp | pPro24(E)-gfp derivative with AAGAAGG RBS |
| pPro7($S^b$)-gfp | pPro24(S)-gfp derivative with AAGAAGG RBS |

[a]E, E. coli-based pPro system
[b]S, Salmonella-based pPro system

Determination of in vivo Promoter Activities. Promoter activities were tested by using GFP as an indirect, quantitative measurement of the transcriptional properties of gfp. Cells grown overnight in LB medium at 37° C. were inoculated (1:100) into M9 medium with either glucose or glycerol (5 mL in culture tube) and grown at 37° C. in a shaking incubator for about 8 hrs. The cells were than subcultured (1:100) into fresh M9 minimal medium with either glucose or glycerol in shake flasks and grown at 37° C. in a shaking incubator. The cells were induced with either propionate or IPTG when the $OD_{600}$ reached around 0.5. GFP fluorescence was measured in a Tecan SpectraFluor Plus plate reader using an excitation wavelength of 405 nm and an emission wavelength of 535 nm and is expressed here as relative fluorescence units (RFU). For each culture, RFU is defined as the culture fluorescence relative to culture biomass at $OD_{600}$ and plotted against the induction time. The GFP content of individual cells was determined with a Beckman-Coulter EPICS XL flow cytometer (Beckman Instruments).

Results

Figure 15A:
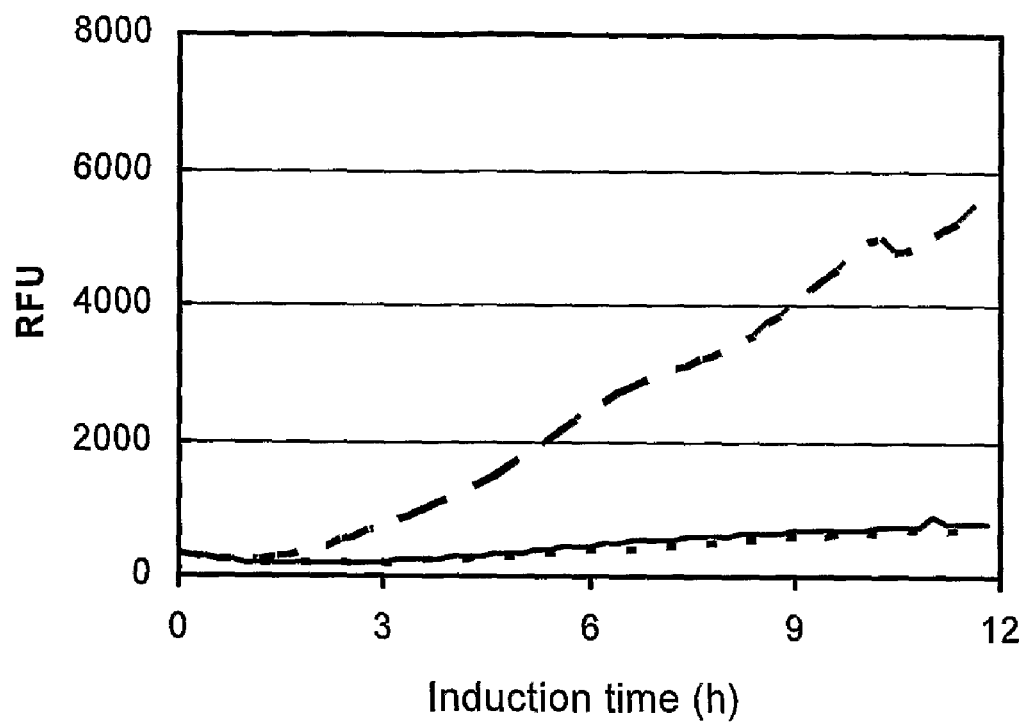
FIGS. 15A and B depict catabolite repression of the pPro system in cells grown in LB medium plus glucose or glycerol.
Figure 15B:
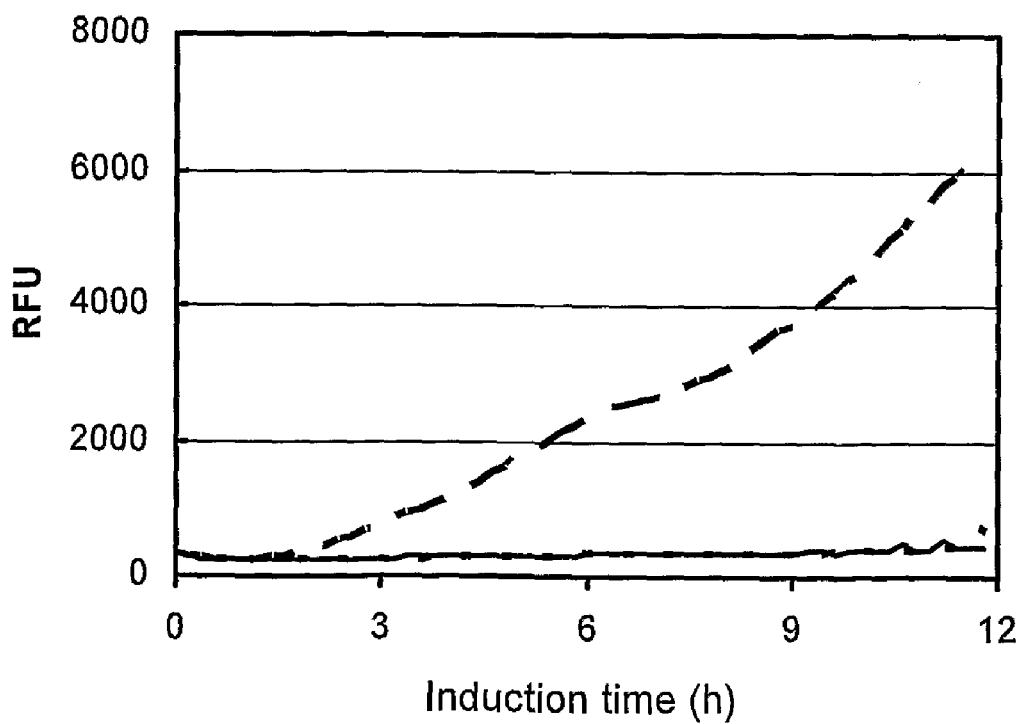

Catabolite Repression by Glucose or Glycerol in Luria-Bertani Medium. It has been reported that both E. coli and Salmonella-based pPro expression systems are negatively affected by the presence of glucose or glycerol in LB medium. To confirm how much these compounds might affect prpB-CDE promoter activity, we measured GFP production in E. coli BL21 harboring pPro7(S)-gfp in LB medium with either glucose or glycerol at concentrations ranging from 0.2 to 2%. The Salmonella $P_{prpB}$ activity, as measured by the $P_{prpBCDE}$-gfp transcriptional fusion, was completely down-regulated even in the presence of 0.2% glucose or glycerol (FIG. 15A and FIG. 15B). These results are consistent with previous reports showing that the expression levels from the Salmonella $P_{prpB}$ promoter decreased to background levels in the presence of glucose in either E. coli or S. enterica). Similar to the E. coli $P_{prpB}$ promoter, the decreased expression level was due to the catabolite-repressed prpR and $P_{prpB}$ promoters, which was mediated by the cAMP-CRP complex.

Modulation of the Salmonella-based pPro expression system in individual E. coli BL21 cells. Flow cytometry was used to examine GFP production from Salmonella $P_{prpB}$-gfp in single cells at different concentrations of propionate. Like the E. coli-based pPro system in LB medium, all cultures grown in M9 minimal medium with either glucose or glycerol were uniformly induced across the population at all propionate concentrations tested (FIGS. 16A and 16B). This result indicates that the *Salmonella*-based pPro system is a controllable expression system in either glucose or glycerol minimal medium. As expected, the culture-averaged fluorescence varied with the amount of propionate added to the culture medium (FIG. 16C). *E. coli* cells harboring pPro7(S)-gfp had higher background expression in glucose minimal medium than in glycerol minimal medium. The maximal expression levels in both carbon sources were obtained at around 5 mM propionate (FIG. 16C), whereas *E. coli* cells harboring pPro7(S)-gfp were fully induced with the addition of 20 mM propionate in LB medium. This finding indicates that the system could be useful for controlling production of proteins at the industrial scale, in part due to the low-cost induction (small amount of inexpensive inducer).

Figure 17A:
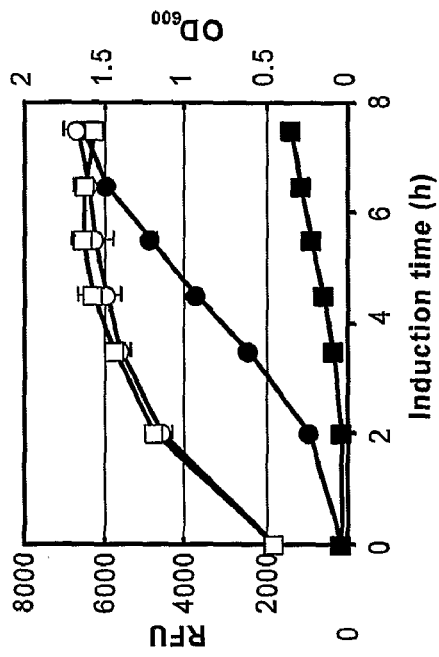
FIGS. 17A-D depict a comparison of cell growth and green fluorescent protein (GFP) expression levels between the pPro and T7 expression systems in shake flask experiments. BL21 (DE3) harboring pET16b-gfp (A), BL21 harboring pPro7(S)-gfp (B) or pPro7(E)-gfp (C), and JSB harboring pPro7(S)-gfp (D) grown in M9 glucose (5 g/L) minimal medium at 37° C. were exposed to IPTG or propionate when the $OD_{600}$ reached ca. 0.5.
Figure 17B:
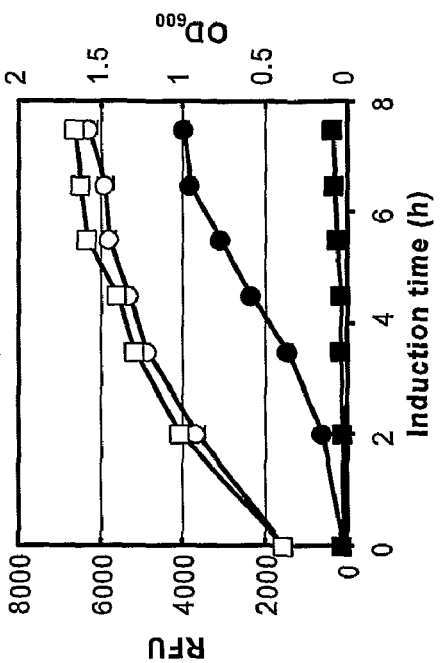
Figure 17C:
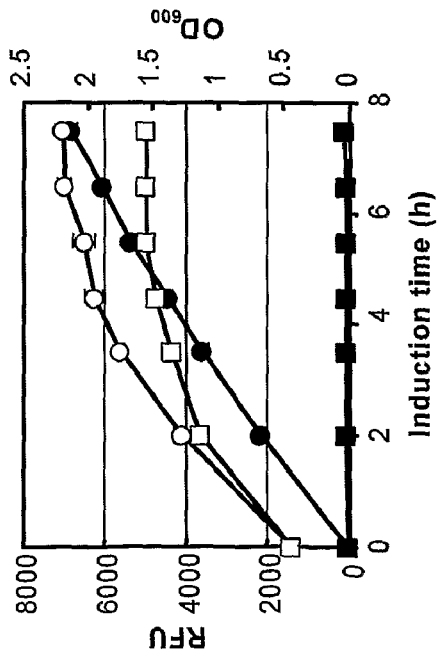
Figure 17D:
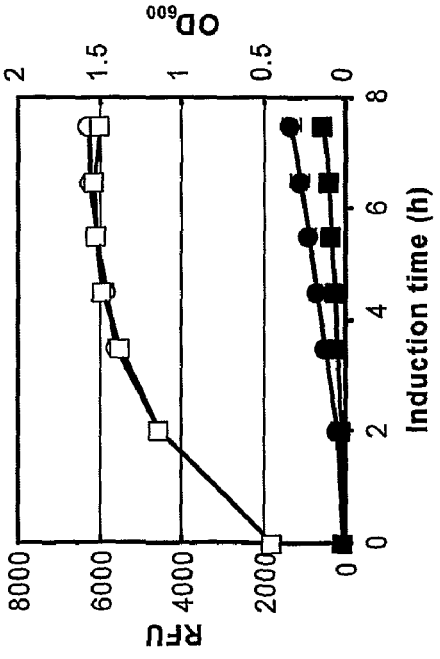

Comparison of GFP production and cell growth from the *Salmonella*-based pPro and the T7 expression systems. The gene encoding GFP was used to compare the expression kinetics of the pPro and T7 systems in *E. coli* BL21 or JSB and BL21 (DE3), respectively. The *Salmonella*-based pPro system exhibited five-fold higher induced expression than the *E. coli*-based pPro system in glucose minimal medium (FIGS. 173B and C). Surprisingly, the expression levels of *E. coli* BL21 harboring pPro7(S)-gfp were similar to those of BL21 (DE3) harboring pET16b-gfp after 6 h of induction in shake flasks (FIGS. 17A and B). However, the *Salmonella*-based pPro system had higher background expression than the T7 expression system (FIGS. 17A and B). To reduce the background expression from the *Salmonella* pPro, *E. coli* JSB was transformed with pPro7(S)-gfp and was tested as a host strain. As a result, the background expression level decreased by ten-fold while the induced expression level was reduced by approximately 35% compared to that of wild-type BL21 harboring pPro7(S)-gfp (FIGS. 17B and D). These results suggest that the *Salmonella*-based pPro system may be comparable to the widely used T7 promoter-driven expression systems.

Figure 18A:
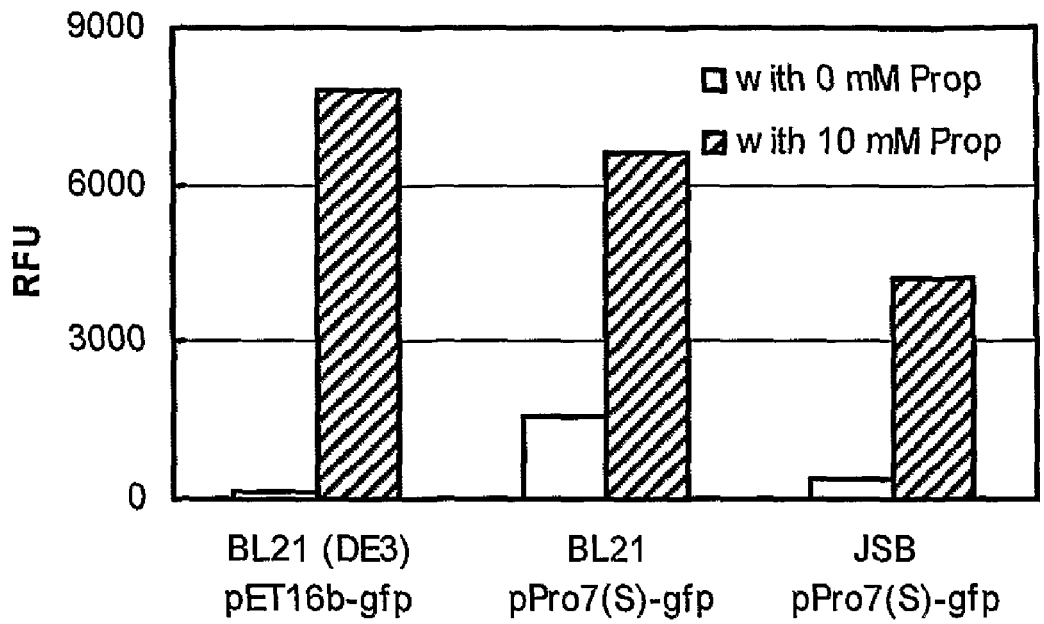
FIGS. 18A and 18B depict a comparison of cell growth and GFP expression levels between the pPro and T7 expression systems in shake flask experiments.

GFP expression from the *Salmonella*-based pPro system in high concentrations of glucose or glycerol. To confirm that this system would be useful for protein production when a high glucose or glycerol concentration is used, expression was tested in minimal medium containing high concentrations of both glucose and glycerol. As was the case using minimal medium with either 0.5% glucose or glycerol as a sole carbon source (FIG. 17A-D), the *Salmonella*-based pPro system showed high induced expression levels in either 1% glucose or glycerol (FIG. 18A,B).

FIGS. 15A and B. Catabolite repression of the pPro system in cells grown in LB medium plus glucose (A) or glycerol (B). Overnight grown *E. coli* BL21 cells harboring pPro7(S)-gfp in LB medium were subcultured (100:1) into fresh LB containing 0.1 M phosphate buffer (pH 7.5). When the $OD_{600}$ reached around 0.4, the culture (180 μL) was inoculated into 96-wells plates containing propionate (6.25 mM) and glucose or glycerol and incubated at 37° C. with shaking in a Tecan SpectraFluor Plus plate reader. GFP fluorescence and $OD_{600}$ were measured. Different lines indicate different glucose or glycerol concentrations added to the medium; 0% (dashed line), 0.2% (solid line), 0.5% (dotted line). The data are representative from three independent experiments. RFU, relative fluorescence units.

FIGS. 16A and B. Histograms showing the number of *E. coli* BL21 cells harboring pPro7(S)-gfp with a given fluorescence (A, B) and culture-averaged fluorescence (C) when grown in M9 glucose (A) or glycerol (B) (5 g/L) minimal medium containing different concentrations of propionate. The fluorescence in single cells or the culture medium was determined after five hours of induction with propionate. Different lines indicate different propionate concentrations added to the medium: control (heavy solid line), 0 mM (medium solid line), 0.02 mM (light solid line), 0.08 mM (dashed line), 0.32 mM (dotted line), 1.25 mM (— - —), and 5.0 mM (— - - —). GFP fluorescence and $OD_{600}$ were measured using a Tecan SpectraFlour Plus plate reader after (1:5) dilution into M9 medium. *E. coli* BL21 harboring pBAD24 (empty vector) is used as a control. Culture-averaged fluorescence was expressed as RFU. Abbreviations are Prop, propionate; Glc, glucose; Gly, glycerol; and C, control.

FIGS. 17A-D. Comparison of cell growth and GFP expression levels between the pPro and T7 expression systems in shake flask experiments. BL21(DE3) harboring pET16b-gfp (A), BL21 harboring pPro7(S)-gfp (B) or pPro7(E)-gfp (C), and JSB harboring pPro7(S)-gfp (D) grown in M9 glucose (5 g/L) minimal medium at 37° C. were exposed to IPTG or propionate when the $OD_{600}$ reached ca. 0.5. Open and filled symbols indicate cell growth and GFP production, respectively. Rectangles indicate GFP production in the presence of 0 mM IPTG (A) or 0 mM propionate (B, C, D); circles, 0.5 mM IPTG (A) or 10 mM propionate (B, C, D). Error bars indicate the standard deviation of experiments performed in triplicate. GFP expression levels and $OD_{600}$ were determined using a Tecan SpectraFluor Plus plate reader after (1:5) dilution into M9 medium.

Figure 18B:
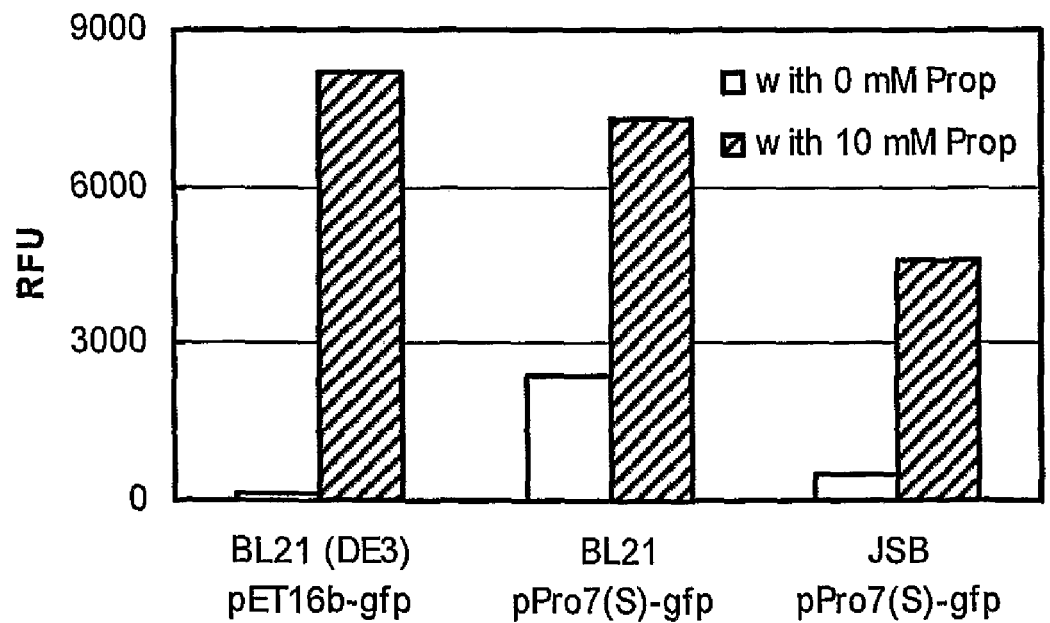

FIGS. 18A and 18B. Comparison of cell growth and GFP expression levels between the pPro and T7 expression systems in shake flask experiments. BL21(DE3) harboring pET16b-p, BL21 harboring pPro7(S)-gfp, and JSB harboring pPro7(S)-gfp in M9 glucose (A) or glycerol (B) (10 g/L) minimal medium at 37° C. were exposed to 0 or 10 mM propionate. GFP expression levels and $OD_{600}$ after 7 h of induction were determined using a Tecan SpectraFluor Plus plate reader after (1:5) dilution into M9 medium.

REFERENCES

1. Amann, E., J. Brosius, and M. Ptashne. 1983. Vectors bearing a hybrid trp-lac promoter useful for regulated expression of cloned genes in *Escherichia coli*. Gene 25:167-178.
2. Baneyx, F. 1999. Recombinant protein expression in *Escherichia coli*. Curr. Opin. Biotechnol. 10:411-421.
3. Barrick, D., K. Villanueba, J. Childs, R. Kalil, T. D. Schneider, C. E. Lawrence, L. Gold, and G. D. Stormo. 1994. Quantitative analysis of ribosome binding sites in *E. coli*. Nucleic Acids Res. 22:1287-1295.
4. Beckwith, J. R. 1978. lac: the genetic system. In *The Operon*; Reznikoff, W. S., ed. Cold Spring Harbor Laboratory Press, Cold Spring Harbor, N.Y.
5. Blank, L., J. Green, and J. R. Guest. 2002. AcnC of *Escherichia coli* is a 2-methylcitrate dehydratase (PrpD) that can use citrate and isocitrate as substrates. Microbiology 148:133-146.
6. Blankenhorn, D., J. Phillips, and J. L. Slonczewski. 1999. Acid- and base-induced proteins during aerobic and anaerobic growth of *Escherichia coli* revealed by two-dimensional gel electrophoresis. J. Bacteriol. 181:2209-2216.
7. Blattner, F. R., G. Plunkett III, C. A. Bloch, N. T. Perna, V. Burland, M. Riley, J. Collado-Vides, J. D. Glasner, C. K. Rode, G. F. Mayhew, J. Gregor, N. W. Davis, H. A. Kirkpatrick, M. A. Goeden, D. J. Rose, B. Mau, and Y. Shao. 1997. The complete genome sequence of *Escherichia coli* K-12. Science 277:1453-1474.

8. Carrier, T. A., and J. D. Keasling. 1999. Investigating autocatalytic gene expression systems through mechanistic modeling. J. Theor. Biol. 201:25-36.
9. Datsenko, K. A., and B. L. Wanner. 2000. One-step inactivation of chromosomal genes in *Escherichia coli* K-12 using PCR products. Proc. Natl. Acad. Sci. USA 97:6640-6645.
10. DeLisa, M. P., J. Li, G. Rao, W. A. Weigand, and W. E. Bentley. 1999. Monitoring GFP-operon fusion protein expression during high cell density cultivation of *Escherichia coli* using an on-line optical sensor. Biotechnol. Bioeng. 65:54-64.
11. Figge, J., C. Wright, C. J. Collins, T. M. Roberts, and D. M. Livingston. 1988. Stringent regulation of stably integrated chloramphenicol acetyl transferase genes by *E. coli* lac repressor in monkey cells. Cell 52:713-722.
12. Guzman, L. M., D. Belin, M. J. Carson, and J. Beckwith. 1995. Tight regulation, modulation, and high-level expression by vectors containing the arabinose $P_{BAD}$ promoter. J. Bacteriol. 177: 4121-4130.
13. Hailer, T., T. Buckel, J. Retey, and J. A. Gerlt. 2000. Discovering new enzymes and metabolic pathways: conversion of succinate to propionate by *Escherichia coli*. Biochemistry 39:4622-4629.
14. Horswill, A. R., and J. C. Escalante-Semerena. 1997. Propionate catabolism in *Salmonella typhimurium* LT2: two divergently transcribed units comprise the prp locus at 8.5 centisomes, prpR encodes a member of the sigma-54 family of activators, and the prpBCDE genes constitute an operon. J. Bacteriol. 179:928-940.
15. Horswill, A. R., and J. C. Escalante-Semerena. 1999a. *Salmonella typhimurium* LT2 catabolizes propionate via the 2-methylcitric acid cycle. J. Bacteriol. 181:5615-5623.
16. Horswill, A. R., and J. C. Escalante-Semerena. 1999b. The prpE gene of *Salmonella typhimurium* LT2 encodes propionyl-CoA synthetase. Microbiology 145:1381-1388.
17. Horswill, A. R., and J. C. Escalante-Semerena. 2001. In vitro conversion of propionate to pyruvate by *Salmonella enterica* enzymes: 2-methylcitrate dehydratase (PrpD) and aconitase enzymes catalyze the conversion of 2-methylcitrate to 2-methylisocitrate. Biochemistry 40:4703-4713.
18. Jensen, P. R., and K. Hammer. 1998. The sequence of spacers between the consensus sequences modulates the strength of prokaryotic promoters. Appl. Environ. Microbiol. 64:82-87.
19. Jensen, P. R., H. V. Westerhoff, and O. Michelsen. 1993. The use of lac-type promoters in control analysis. Eur. J. Biochem. 211:181-191.
20. Khlebnikov, A., and J. D. Keasling. 2002. Effect of lacY expression on homogeneity of induction from the $P_{tac}$ and $P_{trc}$ promoters by natural and synthetic inducers. Biotechnol. Prog. 18:672-674.
21. Khlebnikov, A., K. A. Datsenko, T. Skaug, B. L. Wanner, and J. D. Keasling. 2001. Homogeneous expression of the $P_{BAD}$ promoter in *Escherichia coli* by constitutive expression of the low-affinity high-capacity AraE transporter. Microbiology 147:3241-3247.
22. Khlebnikov, A., O. Risa, T. Skaug, T. A. Carrier, and J. D. Keasling. 2000. Regulatable arabinose-inducible gene expression system with consistent control in all cells of a culture. J. Bacteriol. 182:7029-7034.
23. Lee, S. K., J. D. Newman, and J. D. Keasling. 2005. Catabolite repression of the propionate catabolic genes in *Escherichia coli* and *Salmonella enterica*: evidence for involvement of the cyclic AMP receptor protein. J. Bacteriol. 187:2973-2800.
24. Magasanik, B. 1972. in *The lactose operon*, Cold Spring Harbor Laboratory Press, Cold Spring Harbor, N.Y.
25. Mertens, N., E. Remaut, and W. Fiers. 1995. Tight transcriptional control mechanism ensures stable high-level expression from T7 promoter-based expression plasmids. Biotechnology 13:175-179.
26. Newman, J. R., and C. Fuqua. 1999. Broad-host-range expression vectors that carry the L-arabinose-inducible *Escherichia coli* araBAD promoter and the araC regulator. Gene 227:197-203.
27. Nieboer, M., J. Kingma, and B. Witholt. 1993. The alkane oxidation system of *Pseudomonas oleovorans*: induction of the alk genes in *Escherichia coli* W3110 (pGEc47) affects membrane biogenesis and results in overexpression of alkane hydroxylase in a distinct cytoplasmic membrane subfraction. Mol. Microbiol. 8:1039-1051.
28. Novick, A., and M. Weiner. 1957. Enzyme induction as an all-or-none phenomenon. Proc. Natl. Acad. Sci. USA 43:553-566.
29. Palacios, S., and J. C. Escalante-Semerena. 2000. prpR, ntrA, and ihf functions are required for expression of the prpBCDE operon, encoding enzymes that catabolize propionate in *Salmonella enterica* serovar *typhimurium* LT2. J. Bacteriol. 182:905-910.
30. Palacios, S., and J. C. Escalante-Semerena. 2004. 2-Methylcitrate-dependent activation of the propionate catabolic operon (prpBCDE) of *Salmonella enterica* by the PrpR protein. Microbiology 150:3877-3887.
31. Panke, S., A. Meyer, C. M. Huber, B. Witholt, and M. G. Wubbolts. 1999. An alkane-responsive expression system for the production of fine chemicals. Appl. Environ. Microbiol. 65:2324-2332.
32. Pollock, R., R. Issner, K. Zoller, S, Natesan, V. M. Rivera, and T. Clackson. 2000. Delivery of a stringent dimerizer-regulated gene expression system in a single retroviral vector. Proc. Natl. Acad. Sci. USA 97:13221-13226.
33. Sambrook, J., and D. W. Russel. 2001. Molecular cloning: a laboratory manual, 3rd ed. Cold Spring Harbor Laboratory, Cold Spring Harbor, N.Y.
34. Shine, J., and L. Dalgarno. 1974. The 3'-terminal sequence of *E. coli* 16S ribosomal RNA: complementary to nonsense triplets and ribosome binding sites. Proc. Natl. Acad. Sci. USA 71:1342-1346.
35. Siegele, D. A., and J. C. Hu. 1997. Gene expression from plasmids containing the araBAD promoter at subsaturating inducer concentrations represents mixed populations. Proc. Natl. Acad. Sci. USA 94:8168-8172.
36. Skerra, A. 1994. Use of the tetracycline promoter for the tightly regulated production of a murine antibody fragment in *Escherichia coli*. Gene 151:131-135.
37. Smolke, C. D., T. A. Carrier, and J. D. Keasling. 2000. Coordinated, differential expression of two genes through directed mRNA cleavage and stabilization by secondary structures. Appl. Environ. Microbiol. 66:5399-5405.
38. Su, T. Z., H. Schweizer, and D. L. Oxender. 1990. A novel phosphate-regulated expression vector in *Escherichia coli*. Gene 90:129-133.
39. Textor, S., V. F. Wendisch, A. A. De Graaf, U. Müller, M. I. Linder, D. Linder, and W. Buckel. 1997. Propionate oxidation in *Escherichia coli*: evidence for operation of a methylcitrate cycle in bacteria. Arch. Microbiol. 168:428-436.
40. Zhang, Q., T. R. Tiersch, and R. K. Cooper. 1998. Inducible expression of green fluorescent protein within channel catfish cells by a cecropin gene promoter. Gene 216:207-213.

Bentley et al., "Plasmid-encoded protein: the principal factor in the metabolic burden associated with recombinant bacteria," Biotechnol. Bioeng. 35:668-681 (1990).

Blankenhorn et al., "Acid- and base-induced proteins during aerobic and anaerobic growth of *Escherichia coli* revealed by two-dimensional gel electrophoresis," J. Bacteriol. 181:2209-2216 (1999).

Carrier et al., "Investigating autocatalytic gene expression systems through mechanistic modeling," J. Theor. Biol. 201:25-36 (1999).

Datsenko and Wanner, "One-step inactivation of chromosomal genes in *Escherichia coli* K-12 using PCR products," Proc. Natl. Acad. Sci. USA 97:6640-6645 (2000).

Figge et al., "Stringent regulation of stably integrated chloramphenicol acetyl transferase genes by *E. coli* lac repressor in monkey cells," Cell 52:713-722 (1988).

Guzman et al., "Tight regulation, modulation, and high-level expression by vectors containing the arabinose $P_{BAD}$ promoter," J. Bacteriol. 177: 4121-4130 (1995).

Haller et al., "Discovering new enzymes and metabolic pathways: conversion of succinate to propionate by *Escherichia coli*," Biochemistry 39:4622-4629 (2000).

Hattman et al., "Regulation and expression of the bacteriophage Mu mom gene: mapping of the transactivation (dad) function to the C region," Gene 39:71-76 (1985).

Hoang et al., "Construction and use of low-copy number T7 expression vectors for purification of problem proteins: purification of *Mycobacterium tuberculosis* RmlD and *Pseudomonas aeruginosa* LasI and RhlI proteins, and functional analysis of purified RhlI," Gene 237:361-371 (1999).

Horswill et al., "Propionate catabolism in *Salmonella typhimurium* LT2: two divergently transcribed units comprise the prp locus at 8.5 centisomes, prpR encodes a member of the sigma-54 family of activators, and the prpBCDE genes constitute an operon," J. Bacteriol. 179:928-940 (1997).

Horswill and Escalante-Semerena, "*Salmonella typhimurium* LT2 catabolizes propionate via the 2-methylcitric acid cycle," J. Bacteriol. 181:5615-5623 (1999a).

Horswill and Escalante-Semerena, "The prpE gene of *Salmonella typhimurium* LT2 encodes propionyl-CoA synthetase," Microbiology 145:1381-1388 (1999b).

Horswill and Escalante-Semerena, "In vitro conversion of propionate to pyruvate by *Salmonella enterica* enzymes: 2-methylcitrate dehydratase (PrpD) and aconitase enzymes catalyse the conversion of 2-methylcitrate to 2-methylisocitrate," Biochemistry 40:4703-4713 (2001).

Jeong and Lee, "High-level production of human leptin by fed-batch cultivation of recombinant *Escherichia coli* and its purification," Appl. Environ. Microbiol. 65:3027-3032 (1999).

Khlebnikov and Keasling, "Effect of lacY expression on homogeneity of induction from the $P_{tac}$ and $P_{trc}$ promoters by natural and synthetic inducers," Biotechnol. Prog. 18:672-674 (2002).

Khlebnikov et al., "Homogeneous expression of the $P_{BAD}$ promoter in *Escherichia coli* by constitutive expression of the low-affinity high-capacity AraE transporter," Microbiology 147:3241-3247 (2001).

Khlebnikov et al., "Regulatable arabinose-inducible gene expression system with consistent control in all cells of a culture," J. Bacteriol. 182:7029-7034 (2000).

Kozak, "Comparison of initiation of protein synthesis in prokaryotes, eukaryotes and organelles," Microbiol. Rev. 47:1-45 (1983).

Lee et al., "Catabolite repression of the propionate catabolic genes in *Escherichia coli* and *Salmonella enterica*: evidence for involvement of the cyclic AMP receptor protein," J. Bacteriol. 187:2973-2800 (2005).

Makrides, "Strategies for achieving high-level expression of genes in *Escherichia coli*," Microbiol. Rev. 60:512-538 (1996).

Mertens et al., "Tight transcriptional control mechanism ensures stable high-level expression from T7 promoter-based expression plasmids," Biotechnology 13:175-179 (1995).

Novick and Weiner, "Enzyme induction as an all-or-none phenomenon," Proc. Natl. Acad. Sci. USA 43:553-566 (1957).

Palacios and Escalante-Semerena, "prpR, ntrA, and ihf functions are required for expression of the prpBCDE operon, encoding enzymes that catabolize propionate in *Salmonella enterica* serovar typhimurium LT2," J. Bacteriol. 182:905-910 (2000).

Palacios and Escalante-Semerena, "2-Methylcitrate-dependent activation of the propionate catabolic operon (prpBCDE) of *Salmonella enterica* by the PrpR protein," Microbiology 150:3877-3887 (2004).

Siegele and Hu, Gene expression from plasmids containing the araBAD promoter at subsaturating inducer concentrations represents mixed populations," Proc. Natl. Acad. Sci. USA 94:8168-8172 (1997).

Smolke et al., "Coordinated, differential expression of two genes through directed mRNA cleavage and stabilization by secondary structures," Appl. Environ. Microbiol. 66:5399-5405 (2000).

Spector et al., "The medium/long-chain fatty acyl-CoA dehydrogenase (fadF) gene of *Salmonella typhimurium* is a phase 1 starvation-stress response (SSR) locus," Microbiology 145:15-31 (1999).

Textor et al., "Propionate oxidation in *E. coli*: evidence for operation of a methylcitrate cycle in bacteria," Arch. Microbiol. 168:428-436 (1997).

Williams et al., "Recombinant glycoprotein production in the slime mould *Dictyostelium discoideum*," Curr. Opin. Biotechnol. 6:538-542 (1995).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An expression vector comprising, in order from 5' to 3':
   a) a nucleotide sequence that encodes a transcriptional activator protein, wherein the transcriptional activator protein comprises an amino acid sequence having at least about 95% amino acid sequence identity to the amino acid sequence set forth in SEQ ID NO:3;
   b) a promoter that is inducible by the transcriptional activator protein, wherein the promoter comprises a nucleotide sequence having at least about 95% nucleotide sequence identity to the nucleotide sequence set forth in SEQ ID NO:1 or SEQ ID NO:2; and
   c) a multiple cloning site 3' of and in operable linkage with the transcriptional activator protein-inducible promoter.

2. The vector of claim 1, further comprising a nucleotide sequence encoding a gene product of interest operably linked to the transcriptional activator protein-inducible promoter.

3. The expression vector of claim 1, wherein said vector is functional in a prokaryotic host cell.

4. A composition comprising the vector of claim 1.

5. A host cell comprising the vector of claim 1.

6. The host cell of claim 5, wherein said host cell is a prokaryotic cell.

* * * * *